US012672644B2

(12) United States Patent
McWhirter et al.

(10) Patent No.: US 12,672,644 B2
(45) Date of Patent: Jul. 7, 2026

---

(54) MICE EXPRESSING HUMANIZED Fc α RECEPTORS

(71) Applicant: Regeneron Pharmaceuticals, Inc., Tarrytown, NY (US)

(72) Inventors: John McWhirter, Hastings-On-Hudson, NY (US); Naxin Tu, Pleasantville, NY (US); Andrew J. Murphy, Croton-On-Hudson, NY (US); Lynn MacDonald, Harrison, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 468 days.

(21) Appl. No.: 18/267,340

(22) PCT Filed: Dec. 15, 2021

(86) PCT No.: PCT/US2021/063574
§ 371 (c)(1),
(2) Date: Jun. 14, 2023

(87) PCT Pub. No.: WO2022/132943
PCT Pub. Date: Jun. 23, 2022

(65) Prior Publication Data
US 2024/0065239 A1 Feb. 29, 2024

Related U.S. Application Data

(60) Provisional application No. 63/126,326, filed on Dec. 16, 2020.

(51) Int. Cl.
| | |
|---|---|
| *A01K 67/027* | (2024.01) |
| *A01K 67/0278* | (2024.01) |
| *C07K 14/705* | (2006.01) |
| *C07K 14/735* | (2006.01) |
| *C07K 16/28* | (2006.01) |
| *C12N 15/85* | (2006.01) |

(52) U.S. Cl.
CPC .... *A01K 67/0278* (2013.01); *C07K 14/70535* (2013.01); *C07K 16/2803* (2013.01); *C12N 15/8509* (2013.01); *A01K 2207/15* (2013.01); *A01K 2217/072* (2013.01); *A01K 2227/105* (2013.01); *A01K 2267/03* (2013.01)

(58) Field of Classification Search
None
See application file for complete search history.

(56) References Cited

U.S. PATENT DOCUMENTS

| | | | |
|---|---|---|---|
| 5,633,425 A | 5/1997 | Lonberg et al. | |
| 5,770,429 A | 6/1998 | Lonberg et al. | |
| 5,814,318 A | 9/1998 | Lonberg et al. | |
| 6,075,181 A | 6/2000 | Kucherlapati et al. | |

| | | | |
|---|---|---|---|
| 6,114,598 A | 9/2000 | Kucherlapati et al. | |
| 6,150,584 A | 11/2000 | Kucherlapati et al. | |
| 6,586,251 B2 | 7/2003 | Economides et al. | |
| 6,596,541 B2 | 7/2003 | Murphy et al. | |
| 6,998,514 B2 | 2/2006 | Bruggemann | |
| 7,105,348 B2 | 9/2006 | Murphy et al. | |
| 7,294,754 B2 | 11/2007 | Poueymirou et al. | |
| 7,576,259 B2 | 8/2009 | Poueymirou et al. | |
| 7,659,442 B2 | 2/2010 | Poueymirou et al. | |
| 7,795,494 B2 | 9/2010 | Ghayur | |
| 7,910,798 B2 | 3/2011 | Tanamachi et al. | |
| 8,232,449 B2 | 7/2012 | Tanamachi et al. | |

(Continued)

FOREIGN PATENT DOCUMENTS

| | | |
|---|---|---|
| EP | 2064325 A2 | 6/2009 |
| WO | WO-1999/00010 A2 | 1/1999 |

(Continued)

OTHER PUBLICATIONS

Devoy, et al. (2016) "Genomically humanised mice: technologies and promise", Nature Reviews Genetics, 13(1): 14-20. (Year: 2016).*
Hoelsbrekken, "Killer cell inhibitory receptors and The leukocyte receptor gene complex," retrieved online <https://www.duo.uio.no/bitstream/handle/10852/30393/1/Forskningsoppgaveforskerlinjen1.pdf>: 44 pages (2004).
International Search Report and Written Opinion for International Application No. PCT/US2021/063574 dated Apr. 11, 2022.
Koernig et al., "Topical application of human-derived Ig isotypes for the control of acute respiratory infection evaluated in a human CD89-expressing mouse model," Mucosal Immunology, 12(4): 1013-1024 (2019).

(Continued)

*Primary Examiner* — Robert M Kelly
(74) *Attorney, Agent, or Firm* — Foley Hoag LLP; Brendan T. Jones; Tracy L. Vrablik

(57) ABSTRACT

Provided herein are methods and compositions related to mice that express human or humanized Foot receptors (FcaR) from an FcaR locus positioned in the mouse leukocyte receptor complex (LRC). In certain embodiments, such mice are useful for in vivo testing of therapeutic agents comprising a human IgA Fc (e.g., the testing of the pharmacokinetic and/or pharmacodynamic properties of such therapeutic agents and dosing regimens). Also provided herein are methods of using such mice, cells from such mice, methods of making such mice, and ES cells comprising the same genetic modifications as such mice. Provided herein are methods and compositions related to mice that express human or humanized Foot receptors (FcaR) from an FcaR locus positioned in the mouse leukocyte receptor complex (LRC). In certain embodiments, such mice are useful for in vivo testing of therapeutic agents comprising a human IgA Fc (e.g., the testing of the pharmacokinetic and/or pharmacodynamic properties of such therapeutic agents and dosing regimens). Also provided herein are methods of using such mice, cells from such mice, methods of making such mice, and ES cells comprising the same genetic modifications as such mice.

25 Claims, 6 Drawing Sheets

Specification includes a Sequence Listing.

(56)                    References Cited

U.S. PATENT DOCUMENTS

| | | | |
|---|---|---|---|
| 8,642,835 | B2 | 2/2014 | MacDonald et al. |
| 8,658,154 | B2 | 2/2014 | MacDonald et al. |
| 8,658,853 | B2 | 2/2014 | Macdonald et al. |
| 8,697,940 | B2 | 4/2014 | Macdonald et al. |
| 8,703,485 | B2 | 4/2014 | Buelow |
| 8,754,287 | B2 | 6/2014 | MacDonald et al. |
| 8,883,496 | B2 | 11/2014 | MacDonald et al. |
| 8,907,157 | B2 | 12/2014 | Buelow |
| 9,012,717 | B2 | 4/2015 | Macdonald et al. |
| 9,056,130 | B2 | 6/2015 | Macdonald et al. |
| 9,089,599 | B2 | 7/2015 | Macdonald et al. |
| 9,145,588 | B2 | 9/2015 | Throsby et al. |
| 9,204,624 | B2 | 12/2015 | McWhirter et al. |
| 9,221,894 | B2 | 12/2015 | Macdonald et al. |
| 9,226,484 | B2 | 1/2016 | Macdonald et al. |
| 9,301,510 | B2 | 4/2016 | McWhirter et al. |
| 9,334,334 | B2 | 5/2016 | McWhirter et al. |
| 9,474,255 | B2 | 10/2016 | Murphy et al. |
| 9,516,868 | B2 | 12/2016 | Macdonald et al. |
| 9,546,384 | B2 | 1/2017 | Frendewey et al. |
| 9,686,970 | B2 | 6/2017 | Macdonald et al. |
| 9,706,759 | B2 | 7/2017 | Macdonald et al. |
| 9,738,897 | B2 | 8/2017 | Schoenherr et al. |
| 9,796,788 | B2 | 10/2017 | McWhirter et al. |
| 9,930,871 | B2 | 4/2018 | McWhirter et al. |
| 10,106,820 | B2 | 10/2018 | Auerbach et al. |
| 10,130,081 | B2 | 11/2018 | McWhirter et al. |
| 10,143,186 | B2 | 12/2018 | McWhirter et al. |
| 10,238,093 | B2 | 3/2019 | Macdonald et al. |
| 10,246,509 | B2 | 4/2019 | Macdonald et al. |
| 10,820,582 | B2 | 11/2020 | Guo et al. |
| 11,051,498 | B2 | 7/2021 | Murphy et al. |
| 2002/0088016 | A1 | 7/2002 | Bruggemann |
| 2008/0078000 | A1 | 3/2008 | Poueymirou et al. |
| 2008/0098490 | A1 | 4/2008 | Jakobovits et al. |
| 2009/0053210 | A1 | 2/2009 | Buelow |
| 2010/0146647 | A1 | 6/2010 | Logtenberg et al. |
| 2011/0093963 | A1 | 4/2011 | Buelow |
| 2012/0073004 | A1 | 3/2012 | Macdonald et al. |
| 2012/0167237 | A1 | 6/2012 | Bradley et al. |
| 2012/0207278 | A1 | 8/2012 | Yonekawa |
| 2013/0096287 | A1 | 4/2013 | Macdonald et al. |
| 2013/0111617 | A1 | 5/2013 | Macdonald et al. |
| 2013/0145484 | A1 | 6/2013 | Logtenberg et al. |
| 2013/0167256 | A1 | 6/2013 | Green et al. |
| 2013/0185819 | A1 | 7/2013 | Macdonald et al. |
| 2013/0185821 | A1 | 7/2013 | Babb et al. |
| 2013/0198880 | A1 | 8/2013 | Babb et al. |
| 2013/0212719 | A1 | 8/2013 | Macdonald et al. |
| 2013/0219535 | A1 | 8/2013 | Wabl et al. |
| 2013/0247236 | A1 | 9/2013 | McWhirter et al. |
| 2014/0013456 | A1 | 1/2014 | Mcwhirter et al. |
| 2014/0245468 | A1 | 8/2014 | McWhirter et al. |
| 2014/0309487 | A1 | 10/2014 | Lee et al. |
| 2015/0113668 | A1 | 4/2015 | Bruggemann et al. |
| 2015/0289489 | A1 | 10/2015 | Macdonald et al. |
| 2015/0313195 | A1 | 11/2015 | Macdonald et al. |
| 2017/0086432 | A1 | 3/2017 | Murphy et al. |
| 2017/0347633 | A1 | 12/2017 | Macdonald et al. |
| 2018/0125043 | A1 | 5/2018 | Guo et al. |
| 2019/0223418 | A1 | 7/2019 | Murphy et al. |
| 2019/0261612 | A1 | 8/2019 | Macdonald et al. |
| 2019/0380316 | A1 | 12/2019 | Murphy et al. |
| 2024/0065239 | A1 | 2/2024 | McWhirter et al. |

FOREIGN PATENT DOCUMENTS

| | | | |
|---|---|---|---|
| WO | WO-2006/008548 | A2 | 1/2006 |
| WO | WO-2007/117410 | A2 | 10/2007 |
| WO | WO-2008/027986 | A2 | 3/2008 |
| WO | WO-2008/151081 | A1 | 12/2008 |
| WO | WO-2009/157771 | A2 | 12/2009 |
| WO | WO-2010/039900 | A2 | 4/2010 |
| WO | WO-2010/109165 | A2 | 9/2010 |
| WO | WO-2011/004192 | A1 | 1/2011 |
| WO | WO-2011/123708 | A2 | 10/2011 |
| WO | WO-2011/158009 | A1 | 12/2011 |
| WO | WO-2012/148873 | A2 | 11/2012 |
| WO | WO-2013/041844 | A2 | 3/2013 |
| WO | WO-2013/041846 | A2 | 3/2013 |
| WO | WO-2013/061098 | A2 | 5/2013 |
| WO | WO-2013/079953 | A1 | 6/2013 |
| WO | WO-2013/134263 | A1 | 9/2013 |
| WO | WO-2013/138680 | A1 | 9/2013 |
| WO | WO-2013/138681 | A1 | 9/2013 |
| WO | WO-2013/138712 | A1 | 9/2013 |
| WO | WO-2013/144566 | A2 | 10/2013 |
| WO | WO-2013/144567 | A1 | 10/2013 |
| WO | WO-2013/171505 | A2 | 11/2013 |
| WO | WO-2013/184761 | A1 | 12/2013 |
| WO | WO-2014/093908 | A2 | 6/2014 |
| WO | WO-2014/160179 | A1 | 10/2014 |
| WO | WO-2015/042250 | A1 | 3/2015 |
| WO | WO-2016/062990 | A1 | 4/2016 |
| WO | WO-2016/149678 | A1 | 9/2016 |
| WO | WO-2017/123808 | A1 | 7/2017 |
| WO | WO-2017/214089 | A1 | 12/2017 |
| WO | WO-2018/039180 | A1 | 3/2018 |
| WO | WO-2019/008123 | A2 | 1/2019 |
| WO | WO-2019/190990 | A1 | 10/2019 |
| WO | WO-2020/247623 | A1 | 12/2020 |
| WO | WO-2022/132943 | A1 | 6/2022 |

OTHER PUBLICATIONS

Treffers et al., "IgA-Mediated Killing of Tumor Cells by Neutrophils Is Enhanced by CD47-SIRPα Checkpoint Inhibition," Cancer Immunology Research, 8(1): 120-130 (2019).

Van Tetering et al., "Fc Engineering Strategies to Advance IgA Antibodies as Therapeutic Agents," Antibodies, 9(4): 70 pp. 1-15 (2020).

Zhu et al., "Humanising the mouse genome piece by piece," Nature Communications, 10(1): Article No. 1845 (2019).

Breedveld et al., "IgA and FcaRI: pathological roles and therapeutic opportunities." Frontiers in immunology 10:553 (2019).

Macdonald et al., "Precise and in situ genetic humanization of 6 Mb of mouse immunoglobulin genes." Proc. Natl. Acad. Sci. USA 111(14):5147-52 (2014).

Monteiro et al., "IgA fc receptors." Annu. Rev. Immunol. 21: 177-204 (2003).

Murphy, "VelocImmune: Immunoglobulin Variable Region Humanized Mouse," in Recombinant Antibodies for Immunotherapy, New York, NY, Cambridge University Press, 101-107 (2009).

Poueymirou et al., "FO generation mice fully derived from gene-targeted embryonic stem cells allowing immediate phenotypic analyses." Nature Biotech 25:91-99 (2007).

Valenzuela et al. "High-throughput engineering of the mouse genome coupled with high-resolution expression analysis" Nat. Biotech. 21(6): 652-659 (2003).

Van Egmond et al., "Human Immunoglobulin A Receptor (FcalphaRI, CD89) Function in Transgenic Mice Requires Both FcR ? Chain and CR3 (CD11b/CD18)." Blood 93(12):4387-4394 (1999).

Boross et al., "Ig A EGFR antibodies mediate tumour killing in vivo." EMBO Molecular Medicine 5 (2013): 1213-1226.

Kelley et al., "Comparative genomics of natural killer cell receptor gene clusters." PLoS Genetics 1(2) (2005): e27.

Xu et al., "Critical role of Kupffer cell CD89 expression in experimental IgA nephropathy." PloS One 11 (2016): e0159426.

* cited by examiner

FIG. 3

MICE EXPRESSING HUMANIZED Fc α RECEPTORS

RELATED APPLICATIONS

This application is a 371 National Stage Application of PCT/US2021/063574, filed Dec. 15, 2021, which claims priority to U.S. Provisional Application No. 63/126,326, filed Dec. 16, 2020, which are hereby incorporated by reference in their entirety.

REFERENCE TO A SEQUENCE LISTING

This application contains a Sequence Listing which has been submitted electronically in ASCII format and is hereby incorporated by reference in its entirety. Said ASCII copy, created Mar. 15, 2022, is named RPB-02701_SL, and is 6,904 bytes in size.

BACKGROUND

Mice are an essential in vivo model for preclinical testing of therapeutic agents due to their small size, well-characterized physiology, and relatively inexpensive maintenance compared to larger mammalian models (e.g., primates). Mouse models are often used to assess the toxicity and pharmacokinetics of therapeutic agents prior to proceeding to human clinical studies. Despite these advantages, there are serious drawbacks to in vivo testing of antibodies and Fc fusion proteins as these therapeutic agents can behave differently in mice than they do in humans. This is especially true for testing IgA-based therapeutics in mice as they do not express an Fc receptor for binding IgA antibodies. Thus, mouse models have not been extensively characterized or used for predicting the safety, efficacy, and optimal dosing of IgA-based therapeutic agents. There is a need for new mouse models and methods that allow for precise pre-clinical testing of IgA-based therapeutic agents that are predictive of the properties of such therapeutic agents in human patients.

SUMMARY

Provided herein are methods and compositions related to mice that express a human or humanized Fcα receptor (FcαR) and methods and compositions related to the in vivo testing of therapeutic agents comprising a human IgA Fc in such mice (e.g., the testing of the pharmacokinetic and/or pharmacodynamic properties and dosing regimens of such therapeutic agents). As described herein, mice are convenient animal models for testing therapeutic antibodies and Fc fusion proteins due to their small size, well-characterized physiology, and amenability to genetic modification. Unfortunately, agents comprising a human IgA Fc region (e.g., IgA antibodies and Fcα fusion proteins) often exhibit very different pharmacokinetic and pharmacodynamic properties when administered to wild type mice compared to when administered to humans because such mice lack an FcαR. Thus, the mice provided herein can serve as in vivo systems for the development, screening and testing of human IgA antibodies and Fcα fusion proteins for therapeutic use.

In certain aspects, provided herein is a mouse comprising in its genome an Fc alpha receptor (FcαR) locus positioned in the mouse leukocyte receptor complex (LRC), wherein the FcαR locus (such as human or humanized FcαR locus) comprises a nucleic acid sequence encoding a FcαR polypeptide comprising a human extracellular domain and a human or rodent cytoplasmic domain. In some embodiments, the mouse expresses the FcαR polypeptide on mouse neutrophils, monocytes, macrophages, eosinophils, and dendritic cells (e.g., plasmacytoid dendritic cells). In some embodiment, the neutrophils, monocytes, macrophages, eosinophils, and/or dendritic cells (e.g., plasmacytoid dendritic cells) are from the blood of the mouse. In some embodiment, the neutrophils, monocytes, macrophages, eosinophils, and dendritic cells (e.g., plasmacytoid dendritic cells) are from the spleen of the mouse.

In some aspects, provided herein is a mouse embryonic stem cell (ES cell) comprising in its genome an Fc alpha receptor (FcαR) locus positioned in the leukocyte receptor complex (LRC) of the mouse genome, wherein the FcαR locus comprises a nucleic acid sequence encoding an FcαR polypeptide comprising a human extracellular domain and a human or rodent cytoplasmic domain.

In some embodiments, the FcαR locus is positioned in an intergenic region between the gene loci for the Tthy1 protein and the Rdh13 protein. In some embodiments, the FcαR locus is positioned in an intergenic region between the gene loci for the Lilra5 protein and the Gp6 protein. In some embodiments, the FcαR locus is positioned in an intergenic region between the gene loci for the Pira6 protein and the Gp6 protein. In some embodiments, the FcαR locus is positioned in an intergenic region between the gene loci for the Pira6 protein and the Ncr1 protein. In some embodiments, the FcαR locus is positioned in an intergenic region between the coding nucleic acid sequences for the for the Pira6 protein and the Ncr1 protein. In some embodiments, the intergenic region is the 54 kb region between the Pira6 and Ncr1 loci. In some embodiments, the FcαR locus is positioned between coordinates 4,303,905-4,312,280 on mouse chromosome 7 (+strand, GRCm38 assembly).

In some embodiments, the FcαR locus comprises a nucleic acid sequence encoding a human FcαR polypeptide. In some embodiments, the FcαR locus comprises human exons 1-5 of the human Fc alpha receptor gene. In some embodiments, the FcαR locus comprises a non-coding portion of rodent (non-mouse) FcαR exon 1, a coding portion of human FcαR exons 1 and 2, human FcαR exons 3 and 4, and rodent (non-mouse) FcαR exon 5. In some embodiments, the human or humanized FcαR receptor locus comprises a genomic sequence found between coordinates 54,862,297 and 54,906,185 on human chromosome 19 (+strand, GRCh38 assembly). In some embodiments, the FcαR locus further comprises a nucleic acid sequence present in a human KIR3DL2 gene. In some embodiments, the locus further comprises a nucleic acid sequence present in the 5'UTR of the human NCR1 gene.

In some embodiments, the mouse or mouse ES cell is heterozygous for the FcαR locus. In some embodiments, the mouse or mouse ES cell is homozygous for the FcαR locus.

In some embodiments, the mouse or mouse ES cell of any of the above aspects or embodiments further comprises in its genome a human or humanized Fc gamma receptor (FcγR) locus, a human or humanized IgH locus, a human or humanized Igκ locus, a human or humanized Igλ locus, a human or humanized FcRn locus, a human or humanized β2M locus, and/or a human or humanized FcεR1α locus. In some embodiments, the mouse or mouse ES cell is heterozygous for the human or humanized FcγR locus, the human or humanized IgH locus, the human or humanized Igκ locus, the human or humanized Igλ locus, the human or humanized FcRn locus, the human or humanized β2M locus, and/or the human or humanized FcεR1α locus. In some embodiments, the mouse or mouse ES cell is homozygous for the human or humanized FcγR locus, the human or humanized IgH locus, the human or humanized Igκ locus, the human or humanized Igλ locus, the human or humanized FcRn locus, the human or humanized β2M locus, and/or the human or humanized FcεR1α locus.

In some embodiments, the mouse or mouse ES cell comprising the FcαR locus of the various embodiments described herein comprises in its genome a human or humanized FcγR locus comprising a nucleic acid sequence encoding a human or humanized FcγR. In some embodiments, the human or humanized FcγR locus comprises a nucleic acid sequence encoding one or more low affinity FcγR selected from Fc gamma receptor 2a (FcγR2a), Fc gamma receptor 2b (FcγR2b), Fc gamma receptor 3a (FcγR3a), Fc gamma receptor 3b (FcγR3b), and/or Fc gamma receptor 2c (FcγR2c). In some embodiments, the human or humanized FcγR locus comprises a nucleic acid sequence encoding one or more FcγR selected from a human or humanized Fc gamma receptor 1 alpha (FcγR1a), Fc gamma receptor 2a (FcγR2a), Fc gamma receptor 2b (FcγR2b), Fc gamma receptor 3a (FcγR3a), Fc gamma receptor 3b (FcγR3b), and/or Fc gamma receptor 2c (FcγR2c). In some embodiments, the human or humanized FcγR comprises a human extracellular domain. In some embodiments, the human or humanized FcγR comprises a mouse transmembrane domain. In some embodiments, the human or humanized FcγR comprises a human transmembrane domain. In some embodiments, the human or humanized FcγR comprises a mouse cytoplasmic domain. In some embodiments, the human or humanized FcγR comprises a human cytoplasmic domain. In some embodiments, the human or humanized FcγR locus is positioned at an endogenous mouse FcγR locus. In some embodiments, the nucleic acid sequence encoding the human or humanized FcγR replaces all or part of an endogenous mouse FcγR gene. In some embodiments, the nucleic acid sequence encoding the human or humanized FcγR comprises a nucleic acid sequence encoding a human FcγR extracellular domain that replaces an endogenous nucleic acid sequence encoding a mouse FcγR extracellular domain. In some embodiments, the mouse of any of the above embodiments does not express a mouse FcγR.

In certain aspects, provided herein is a method for testing a human IgA antibody or an Fcα fusion polypeptide comprising administering the IgA antibody or Fcα fusion polypeptide to a mouse of any of the above embodiments.

In some embodiments, the method further comprises measuring one or more pharmacokinetic properties of the administered human IgA antibody or Fcα fusion polypeptide. In some embodiments, the one or more pharmacokinetic properties are selected from one or more of area under the plasma concentration versus time (AUC), in vivo recovery (IVR), clearance rate (CL), mean residence time (MRT), agent half-life (t½), and/or volume of distribution at steady state (Vss). In some embodiments, the method further comprises measuring the therapeutic efficacy of the administered human antibody or Fcα fusion polypeptide. In some embodiments, the method further comprises administering a plurality of doses of the human antibody or Fcα fusion polypeptide and determining a therapeutic efficacy of each dose of the human antibody or Fcα fusion polypeptide. In some embodiments, the method further comprises administering a plurality of doses of the human antibody or Fcα fusion polypeptide and determining the safety of each dose of the human antibody or Fcα fusion polypeptide. In some embodiments, the method further comprises administering a plurality of doses of the human antibody or Fcα fusion polypeptide and determining the tolerability of each dose of the human antibody or Fcα fusion polypeptide. In some embodiments, the method further comprises measuring one or more Fc receptor mediated responses in the mouse. In some embodiments, the one or more Fc receptor mediated responses is an antibody-dependent cell-mediated cytotoxicity (ADCC) response. In some embodiments, the human antibody binds to a target cell in the mouse, and the method further comprises measuring antibody-dependent cell-mediated cytotoxicity (ADCC) of natural killer (NK) cells against the target cell and comparing the amount of ADCC to a control, wherein increased target cell killing indicates the agent has increased ability to mediate ADCC. In some embodiments, the method further comprises measuring the immune response generated by the mouse against the human antibody.

In certain aspects, provided herein is a method of making a mouse comprising a Fc alpha receptor (FcαR) locus, the method comprising: generating a mouse ES cell comprising in its genome an Fc alpha receptor (FcαR) locus positioned in the leukocyte receptor complex (LRC) of the mouse genome as provided herein; and generating a mouse from said ES cell.

In certain aspects, provided herein is a method of modifying a mouse genome, the method comprising inserting an Fc alpha receptor (FcαR) locus into the leukocyte receptor complex (LRC) of a mouse genome, thereby modifying the mouse genome, wherein the FcαR locus comprises a nucleic acid sequence encoding an FcαR polypeptide comprising a human extracellular domain and a human or rodent cytoplasmic domain. In some embodiments, the FcαR locus comprises a nucleic acid sequence encoding a human or humanized FcαR polypeptide. In certain embodiments, the FcαR locus is positioned in an intergenic region between the gene loci for the Tthy1 protein and the Rdh13 protein. In some embodiments, the FcαR locus is positioned in an intergenic region between the gene loci for the Lilra5 protein and the Gp6 protein. In some embodiments, the FcαR locus is positioned in an intergenic region between the gene loci for the Pira6 protein and the Gp6 protein. In some embodiments, the FcαR locus is positioned in an intergenic region between the gene loci for the Pira6 protein and the Ncr1 protein. In some embodiments, the intergenic region is the 54 kb region between the Pira6 and Ncr1 loci. In certain embodiments, the FcαR locus is between coordinates 4,303,905-4,312,280 on mouse chromosome 7 (+strand, GRCm38 assembly).

BRIEF DESCRIPTION OF THE DRAWINGS

Unless specifically indicated, the figures use empty boxes for human gene sequences, closed boxes for mouse gene sequences, single line for mouse intergenic sequences and double line for human intergenic sequences, empty boxes with text therein (e.g., Lox, CM) for the selection cassettes.

FIG. 3 is a diagram (not to scale) of a humanized low affinity FcγR locus, comprising human FcγR2B, FcγR3B, FcγR2C, FcγR3A, and FcγR2A genes on mouse chromosome 1. Detailed steps of humanization of this locus are described in U.S. Pat. No. 8,658,154, incorporated herein by reference.

DETAILED DESCRIPTION

General

Figure 1A:
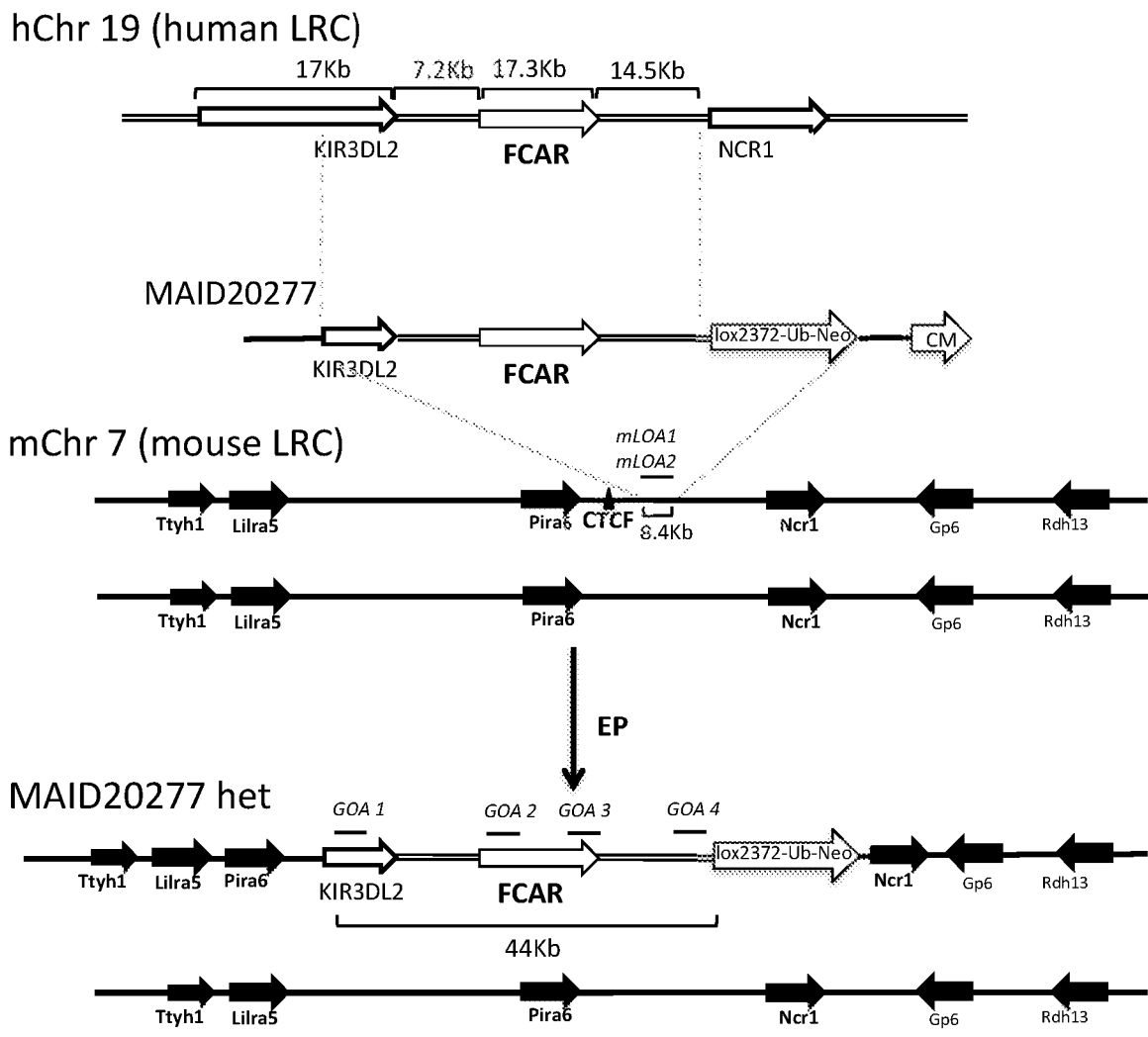
FIG. 1A is a diagram (not to scale) illustrating the insertion of the MAID20277 cassette into a mouse genome to generate heterozygous mice that can be bred to homozygosity. "LRC" denotes leukocyte receptor complex and "EP" denotes electroporation. The names and locations of the primers and probes used in a modification of allele (MOA) assay (described in the Examples) are indicated as short lines above the diagram.

Provided herein are methods and compositions related to mice that express a human, humanized, or partially-humanized Fcα receptor (FcαR) and methods and compositions related to the in vivo testing of therapeutic agents comprising a human IgA Fc in such mice (e.g., the testing of the pharmacokinetic and/or pharmacodynamic properties and dosing regimens of such therapeutic agents). Specifically, various embodiments described herein relate to mice, ES cells, and methods comprising a gene encoding and/or expressing a completely human or partially human FcαR1/CD89 gene/receptor (referred to herein as "FcαR"). The genetically modified mice comprise in their genome a nucleic acid sequence encoding a human or humanized Fc alpha receptor (FcαR) protein. In some embodiments, the sequence encoding a human or humanized Fc alpha receptor (FcαR) protein is positioned in the leukocyte receptor complex (LRC) on mouse chromosome 7. In some embodiments, the nucleic acid sequence encoding the FcαR is positioned in an intergenic region between the gene loci for the Tthy1 protein and the Rdh13 protein, the Lilra5 polypeptide and the Gp6 polypeptide, and/or the Pira6 protein and the Ncr1 protein (e.g., between the coding nucleic acid sequences for the Pira6 protein and the Ncr1 protein). In some embodiments, the intergenic region is the 54 kb region between the Pira6 and Ncr1 loci. In some embodiments, the mice provided herein express human FcαR from a locus positioned between coordinates chr7:4,303,905-4,312,280 in the mouse genome (+strand, GRCm38 assembly). In some embodiments, the FcαR comprises a human extracellular domain. The transmembrane and/or cytoplasmic domains of such receptors can be human or non-human (e.g., rat).

Therapeutic agents comprising a human IgA Fc, such as therapeutic human antibodies and human Fcα fusion proteins, are typically tested in non-human species before they are administered to humans. While such agents are often tested in non-human primates or other relatively large mammals, such testing is expensive and places a significant financial burden on drug developers. Moreover, non-human primates and other relatively large mammals are often not amenable to genetic modification, which limits the disease models available in such organisms.

In contrast, mice are convenient animal models for testing therapeutic antibodies and Fc fusion proteins due to their small size, well-characterized physiology, and amenability to genetic modification. Unfortunately, agents comprising a human IgA Fc region often exhibit very different pharmacokinetic and pharmacodynamic properties when administered to prior art mice compared to when administered to humans because wild type mice lack an FcαR. Thus, the mice provided herein can serve as in vivo systems for the development, screening and testing of human IgA antibodies and Fcα fusion proteins for therapeutic use.

The position of a transgene within the genome of a mouse can have a significant effect on its expression. For example, mice comprising a human FcαR transgene have been reported to express FcαR on neutrophils, but only on a subpopulation of monocytes. For example, macrophages isolated from the peritoneal cavity and nonmyeloid cells, such as lymphocytes, endothelial cells, and hepatocytes showed no FcαR expression in such mice. van Egmond et al., *Blood* 93(12):4387-4394 (1999). In contrast, in humans, FcαR is typically expressed on neutrophils, monocytes, macrophages (e.g., Kupffer cells), eosinophils, and dendritic cells. Thus, in certain embodiments the mice provided herein express human FcαR from a position in the mouse genome that corresponds to the position of human endogenous FcαR locus or a position in their genome that corresponds to loci located near the position of human endogenous FcαR locus in the human genome. Specifically, in certain embodiments, the sequence encoding a human or humanized Fc alpha receptor (FcαR) protein is positioned in the leukocyte receptor complex (LRC) on mouse chromosome 7. In some embodiments, the mice provided herein express human FcαR from a locus positioned in an intergenic region between the gene loci for the Tthy1 protein and the Rdh13 protein, the Lilra5 polypeptide and the Gp6 polypeptide, and/or the Pira6 protein and the Ncr1 protein (e.g., between the coding nucleic acid sequences for the Pira6 protein and the Ncr1 protein). In some embodiments, the intergenic region is the 54 kb region between the Pira6 and Ncr1 loci. In some embodiments, the mice provided herein express human FcαR from a locus positioned between coordinates chr7:4,303,905-4,312,280 in the mouse genome (+strand, GRCm38 assembly). In some embodiments provided herein, mice described herein express FcαR on cell surface of their neutrophils, monocytes/macrophages (e.g., blood monocytes/macrophages), eosinophils and dendritic cells (e.g., plasmacytoid dendritic cells).

In various embodiments of mice, ES cells and methods provided herein, the genome comprises and/or the mouse expresses the human or humanized FcαR as described herein in association with a wild type mouse FcR γ chain. Thus, in some embodiments, the human or humanized FcαR is expressed on a surface of a mouse cell in association with endogenous mouse FcR γ chain.

In some embodiments, the mice provided herein further comprise a reduced mouse-anti-human immune response following administration of a therapeutic agent comprising a human Fcα. This can be accomplished through the use of mice that have been genetically modified such that they express a human Fc that matches the Fc present in the administered antibody or Fc fusion protein. Such mice can be made, for example, through the insertion of a nucleic acid sequence that encodes a human immunoglobulin heavy chain constant region, in whole or in part, in the place of a sequence that encodes the corresponding portions of an endogenous non-human immunoglobulin heavy chain constant region gene segment. Such animals recognize the human Fc as a "self" protein and are therefore less likely to develop an immune response against the administered human Fc-containing therapeutic.

In addition, in some embodiments, the mice provided herein express Fcα receptors (FcαRs) that are able interact with human Fcα similarly to the FcαRs expressed by a human patient. For example, in certain embodiments the genetically modified mice provided herein express an FcαR having at least human extracellular domains (e.g., the transmembrane and cytoplasmic domains can be either human or rat). In certain embodiments, in addition to expressing a human or partially human FcαR, the mice provided herein express a human or partially human β2M, a human or partially human FcεR1α, a human or partially human FcγR1α, a human or partially human FcγR2a, a human or partially human FcγR2b, a human or partially human FcγR3a, a human or partially human FcγR3b, and/or a human or partially human FcγR2c. Such mice are therefore able to more accurately mimic the human Fc responses of human patients compared to mice with fully non-human Fc receptors.

Thus, in certain embodiments, mice provided herein are a novel in vivo system for the development, selection and testing of therapeutic human IgA antibodies and Fc fusion proteins based not merely on specificity and/or affinity for antigen, but on the relevant whole biological function of the selected antibody through evaluation of effector functions of the immune system. In this way, human therapeutic candidates can be developed and selected based on therapeutic potential evaluated on a whole molecule level with relevant biological responses (e.g., cellular responses) rather than predictions based solely on individual components evaluated separately. Thus, the mice disclosed herein specifically provide a suitable system for predicting and characterizing human therapeutic antibody function in vivo.

The transgenic mice expressing a human FcαR disclosed herein can be used in studying the functional role the receptor has in immune responses at reduced costs relative to larger animal models or to humans. Moreover, mice are a more suitable model for ascertaining basic biological functions that can then be confirmed in larger animals or humans. For example, mice expressing a human FcαR have been previously used to study the receptor's role in antibody-dependent cellular toxicity (ADCT) and to identify other components necessary for the FcαR-mediated response. See van Egmond et al. (1999) Blood, 93(12): 4387-94.

IgA antibodies play important roles in the development and progression of certain diseases. Breedveld and van Egmond discuss several diseases and conditions in which IgA antibodies play a role ((2019) Frontiers in Immunology, 10:553). For example, several autoimmune diseases are characterized by an increased abundance of IgA antibodies (e.g., rheumatoid arthritis and IgA Nephropathy). In inflammatory bowel disease, bacteria opsonized with IgA can result in cross-linking of FcαRs and activation of neutrophils that results in tissue damage. Low IgA levels are also associated with certain diseases. A potential link has been found between low IgA levels and the severity of allergic asthma, but at the same time high levels are found in subjects with allergic rhinitis. The mice described herein can be used to identify the role of the FcαR on the severity of the disease or the impact FcαR inhibitors have on muting symptoms.

A lack of IgA can result in increased susceptibility to infection, especially mucosal infections. Administration of excessive amounts of IgA can result in enhanced activation of the FcαR, which can result in unintended complications. Thus, the mice described herein can be used to ascertain suitable dosing regimens that suitably overcome an IgA deficiency without initiating side effects. The mice described herein can also be used to assess the efficacy of FcαR inhibitors for the treatment of inflammation, which can be IgA-mediated.

In some embodiments, the mice described herein can be treated with anti-tumor (or pathogen) candidate IgA therapeutics or IgA Fc fusion proteins, or bispecific antibodies directed to FcαR and tumor antigens. In other words, the mice described herein may be used for preclinical evaluation of therapies that implicate IgA and/or FcαR.

Definitions

The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof, amino acid analogs having variant side chains; and all stereoisomers of any of any of the foregoing.

As used herein, the term "antibody" may refer to both an intact antibody and an antigen binding fragment thereof. Intact antibodies are glycoproteins that include at least two heavy (H) chains and two light (L) chains inter-connected by disulfide bonds. Each heavy chain includes a heavy chain variable domain and a heavy chain constant domain. Each light chain includes a light chain variable domain and a light chain constant domain. The heavy chain variable domains and light chain variable domains can be further subdivided into domains of hypervariability, termed complementarity determining regions (CDR), interspersed with regions that are more conserved, termed framework regions (FR). Each heavy chain variable domain and light chain variable domain is composed of three CDRs and four FRs, arranged from amino-terminus to carboxy-terminus in the following order: FR1, CDR1, FR2, CDR2, FR3, CDR3, FR4. The variable domains of the heavy and light chains contain a binding domain that interacts with an antigen.

The terms "antigen binding fragment" and "antigen-binding portion" of an antibody, as used herein, refers to one or more fragments of an antibody that retain the ability to bind to an antigen. Examples of binding fragments encompassed within the term "antigen-binding fragment" of an antibody include Fab, Fab', F(ab')$_2$, Fv, scFv, disulfide linked Fv, Fd, single-chain antibodies, isolated CDRH3, and other antibody fragments that retain at least a portion of the variable domain of an intact antibody. These antibody fragments can be obtained using conventional recombinant and/or enzymatic techniques and can be screened for antigen binding in the same manner as intact antibodies.

As used herein the term "area under the plasma concentration versus time curve" or "AUC" refers to the rate and extent of elimination of a therapeutic agent following administration. In some embodiments, AUC is determined over a specified time period, such as 12, 18, 24, 36, 48, or 72 hours, or for infinity using extrapolation based on the slope of the curve. Unless otherwise specified herein, AUC is determined for infinity (AUC$_{INF}$). AUC may also be calculated on a per dose basis. As with many of the other PK parameters, the determination of AUC may be carried out in a single animal, or in a population of animals for which the average is calculated.

As used herein, the term "clearance rate" or "CL" refers to a measure of the body's ability to eliminate a drug, and is expressed as the volume of plasma cleared of drug over time.

The phrase "derived from" when used concerning a rearranged variable region gene "derived from" an unrearranged variable region and/or unrearranged variable region gene segments refers to the ability to trace the sequence of the rearranged variable region gene back to a set of unrearranged variable region gene segments that were rearranged to form a gene that expresses the variable domain (accounting for, where applicable, splice differences and somatic mutations). For example, a rearranged variable region gene that has undergone somatic mutation is still derived from the unrearranged variable region gene segments. In some embodiments, where the endogenous locus is replaced with a universal light chain or heavy chain locus, the term "derived from" indicates the ability to trace origin of the sequence to said rearranged locus even though the sequence may have undergone somatic mutations.

As used herein, the phrase "endogenous gene" or "endogenous gene segment" refers to a gene or gene segment found in a parent or reference organism prior to introduction of a disruption, deletion, replacement, alteration, or modification as described herein. In some embodiments, a reference organism is a wild-type organism. In some embodiments, a reference organism is an engineered organism. In some embodiments, a reference organism is a laboratory-bred organism (whether wild-type or engineered).

The term "in vivo recovery" or "IVR" refers to the incremental recovery (K-value), which is the observed peak activity minus predose level and then divided by the dose. IVR may also be calculated on a percentage basis. The mean IVR can be determined in an animal population, or the individual IVR can be determined in a single animal.

As used herein, the term "locus" refers to a location on a chromosome. In some embodiments, a locus contains a set of related genetic elements (e.g., genes, gene segments, regulatory elements). For example, the human leukocyte receptor complex (LRC) locus is located on chromosome 19 and comprises genes including KIR, FcαR, NCRI, NLRP, GP6, and Rdh13, among others. A murine locus homologous to the human LRC locus is on mouse chromosome 7 and comprises several homologous genes to those in the human LRC (e.g., Ncr1, Gp6, and Rdh13 genes). A locus can be endogenous or non-endogenous. The term "endogenous locus" refers to a location on a chromosome at which a particular genetic element is naturally found. In some embodiments, an endogenous locus has a sequence found in nature. In some embodiments, an endogenous locus is a wild-type locus. In some embodiments, an endogenous locus is an engineered locus.

The terms "polynucleotide" and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

As used herein, the term "volume of distribution at steady state" or "Vss" refers to the apparent space (volume) into which a drug distributes. More particularly, Vss represents the amount of drug in an animal's body divided by the plasma concentration at steady state.

As used herein, the term "CH gene segment" (e.g., Cγ1 gene segment, Cᵞ2a gene segment, Cᵞ2c gene segment, Cμ gene segment, Cᵞ2b gene segment, Cᵞ3 gene segment, Cδ gene segment, Cε gene segment, Cα gene segment, etc.) refers to a segment of DNA sequence that encodes the immunoglobulin heavy chain constant region and may be used interchangeably with $C_H$ gene (e.g., Cγ gene, $C_{\gamma 2a}$ gene, $C_{\gamma 2c}$ gene, $C_{\gamma 3}$ gene, $C_{\gamma 2b}$ gene, Cμ gene, $C_\delta$ gene, Cε gene, $C_\alpha$ gene, etc.). For example, Cγ1 gene segment or Cγ1 gene refers to a segment of DNA sequence that encodes the IgG1 constant region. The term "$C_H$ gene segment locus" refers to a location on a chromosome at which the $C_H$ gene segment or $C_H$ gene is naturally found.

Genetically Modified Loci

In some aspects, the genetically mice and cells (e.g., ES cells) described herein that are useful for in vivo testing of therapeutic agents comprise a human IgA antibody or Fcα fusion protein (e.g., the testing of the pharmacokinetic and/or pharmacodynamic properties of such a therapeutic agent). The genetically modified mice disclosed herein comprise at least one locus in their genome that comprises a nucleic acid sequence encoding a human or humanized FcαR and that corresponds to the position of human endogenous FcαR locus or a position in the mouse genome that corresponds to loci located near the position of human endogenous FcαR locus in the human genome. For example, in certain embodiments, the sequence encoding a human or humanized Fc alpha receptor (FcαR) protein is positioned in the leukocyte receptor complex (LRC) on mouse chromosome 7. In some embodiments, sequence encoding a human or humanized Fc alpha receptor (FcαR) protein is positioned in an intergenic region between the gene loci for the Tthy1 protein and the Rdh13 protein, the Lilra5 polypeptide and the Gp6 polypeptide, the Pira6 protein and the Gp6 protein, and/or the Pira6 protein and the Ncr1 protein. In some embodiments, the sequence encoding a human or humanized Fc alpha receptor (FcαR) protein is positioned between coordinates chr7:4,303,905-4,312,280 in the mouse genome (+strand, GRCm38 assembly). In some embodiments, the intergenic region is the 54 kb region between the Pira6 and Ncr1 loci. In some embodiments, the nucleic acid sequence that encodes the FcαR further comprises a nucleic acid sequence that encodes all or part of the human KIR3DL2 gene, and/or further comprises a nucleic acid sequence of all or part of the human NCR1 gene, e.g., a nucleic acid sequence present in the 5'UTR of human NCR1 gene.

In some embodiments, the genetically modified mice comprise genetically modified loci that encode antibody heavy chains comprising a human Fc (e.g., a human IgA1 Fc, a human IgA2 Fc). Such loci are disclosed in WO2019/190990, the contents of which are incorporated by reference in their entirety. In some embodiments, the mice and/or ES cells comprise genetically modified loci that encode fully or partially human light chains (e.g., that encode λ light chains or κ light chains). Such loci are disclosed in WO2019/190990 and U.S. Pat. No. 10,820,582, the contents of which are incorporated by reference in their entirety. In some embodiments, the genetically modified mice and ES cells further comprise one or more loci that encode Fc receptors with a human extracellular domain (e.g., a Neonatal Fc Receptor (FcRn) α-chain, a β-2-microglobulin polypeptide (β2M), an Fc ε receptor 1α (FcεR1α) α-chain, an Fc γ receptor 1 alpha (FcγR1α) α-chain, an Fc gamma receptor 2a (FcγR2a) α-chain, an Fc gamma receptor 2b (FcγR2b) α-chain, an Fc gamma receptor 3a (FcγR3a) α-chain, an Fc gamma receptor 3b (FcγR3b) α-chain, an Fc gamma receptor 2c (FcγR2c) α-chain). In some embodiments, the transmembrane and cytoplasmic domain encoded by such loci can be human or non-human (e.g., rodent, such as mouse). Such loci are disclosed in WO2019/190990, and U.S. Pat. Nos. 9,474,255, and 8,658,154, the contents of each of which are incorporated by reference in their entirety.

Humanized Fc Alpha Receptor

The mice or embryonic stem (ES) cells provided herein express and/or comprise in their genome a humanized or human Fc alpha receptor 1 (FcαR1). Mice do not have an FcαR homolog. Thus, in some embodiments, the mice or ES cells comprise at least one locus in their genome that comprises a nucleic acid sequence encoding a human or humanized FcαR and that corresponds to the position of human endogenous FcαR locus or a position in the mouse genome that corresponds to loci located near the position of human endogenous FcαR locus in the human genome. For example, in certain embodiments, the sequence encoding a human or humanized Fc alpha receptor (FcαR) protein is positioned in the leukocyte receptor complex (LRC) on mouse chromosome 7. In some embodiments, sequence encoding a human or humanized Fc alpha receptor (FcαR) protein is positioned in an intergenic region between the gene loci for the Tthy1 protein and the Rdh13 protein, the Lilra5 polypeptide and the Gp6 polypeptide, and/or the Pira6 protein and the Ncr1 protein. In some embodiments, the sequence encoding a human or humanized Fc alpha receptor (FcαR) protein is positioned between coordinates chr7:4,303,905-4,312,280 in the mouse genome (+strand, GRCm38 assembly). In some embodiments, the intergenic region is the 54 kb region between the Pira6 and Ncr1 loci. In some embodiments, the nucleic acid sequence that encodes the FcαR further comprises a nucleic acid sequence that encodes all or part of the human KIR3DL2 gene, and/or further comprises a nucleic acid sequence of all or part of human NCR1 gene, e.g., a nucleic acid sequence present in the 5'UTR of human NCR1 gene. In certain embodiments, the mice provided herein express FcαR on neutrophils, monocytes, macrophages (e.g., induced macrophages), eosinophils, and/or dendritic cells. In some embodiments the neutrophils, monocytes, macrophages (e.g., induced macrophages), eosinophils, and/or dendritic cells are blood neutrophils, monocytes, macrophages (e.g., induced macrophages), eosinophils, and/or dendritic cells. In some embodiments the neutrophils, monocytes, macrophages (e.g., induced macrophages), eosinophils, and/or dendritic cells are spleen neutrophils, monocytes, macrophages (e.g., induced macrophages), eosinophils, and/or dendritic cells.

FcαR is an activating receptor that complexes with the human FcR γ chain, and has a medium affinity ($K_a\sim5\times10^6$ $M^{-1}$) for human IgA1, IgA2, and secretory IgA and high avidity ($K_a\sim5\times10^6$ $M^{-1}$) for complexed IgA. FcαR binding to IgA coated particles triggers release of inflammatory mediators, phagocytosis, and antibody-dependent cell-mediated cytotoxicity. Tumor cells can be effectively lysed using IgA anti-tumor therapy by directing neutrophils to tumor cells. In addition to the full-length receptor, neutrophils and eosinophils express an alternatively spliced form of the receptor, which can bind secretory IgA. In vivo, two FcαR molecules dimerize and interact an IgA monomer.

In some embodiments, the FcαR locus comprises a nucleic acid sequence encoding an FcαR polypeptide comprising a human extracellular domain, a rodent (that is not a mouse, e.g., rat) transmembrane domain and a rodent (that is not a mouse, e.g., rat) cytoplasmic domain. In some embodiments, the FcαR locus comprises a nucleic acid sequence encoding an FcαR polypeptide comprising a human extracellular domain, a human transmembrane domain and a rodent (that is not a mouse, e.g., rat) cytoplasmic domain. In some embodiments, the FcαR locus comprises a nucleic acid sequence encoding an FcαR polypeptide comprising a human extracellular domain, a human transmembrane domain and a human cytoplasmic domain.

In some embodiments, the FcαR gene locus comprises non-human regulatory elements (e.g., non-human promoters and/or enhancers). In some embodiments, the non-human regulatory elements are rodent regulatory elements (e.g., rat or mouse promoters or enhancers). In other embodiments, the FcαR gene locus comprises human regulatory elements (e.g., human promoters and/or enhancers).

As is described in the art (see, e.g., Monteiro and van de Winkel, (2003) Annu. Rev. Immunol. 21:177-204), the human FcαR gene consists of 5 exons: exon 1 including the 5' UTR, ATG translation initiation codon and part of the leader peptide encoding sequence; exon 2 encoding the remainder of the leader peptide; exons 3 and 4 encoding two extracellular domains, EC1 and EC2, of FcαR, with EC1 being the domain that binds to an IgA Fc; and exon 5 encoding the cytoplasmic and transmembrane domains of the protein.

In some embodiments, a nucleic acid encoding a human or humanized FcαR polypeptide provided herein encodes a fully human FcαR polypeptide. In certain embodiments, such a nucleic acid comprises a humanized exon 1 (e.g., comprising a rodent (non-mouse, e.g., rat) 5' UTR and a human coding sequence), human coding exons 2-5 through the stop codon, and a human or rodent (non-mouse, e.g., rat) 3'UTR and polyA. In some embodiments, the nucleic acid encoding human or humanized FcαR polypeptide comprises exons 1-5 of the human FcαR gene.

In some embodiments, the nucleic acid is used to generate a targeting vector for insertion into the mouse ES cell genome. In some embodiments, the nucleic acid encoding the human or humanized FcαR polypeptide comprises ~44 kb of human genomic sequence including the FCAR gene. In some embodiments, the human genomic sequence is the genomic sequence located on human chromosome 19, with coordinates chr19: 54,862,297-54,906,185 (+strand, assembly GRCh38), which includes the 3' end of the KIR3DL2 gene, and the entire human FCAR gene.

In some embodiments, a nucleic acid encoding a FcαR polypeptide is a chimeric rodent (non-mouse, e.g., rat)/human sequence. In some embodiments, the chimeric rodent (non-mouse, e.g., rat)/human sequence comprises a human, rat or chimeric rat/human exon 1 (such that the nucleic acid sequence encoding the leader sequence is either human or rat); a human or rat exon 2, human exons 3-4; and rat exon 5. In these embodiments, the nucleic acid encodes a FcαR polypeptide comprising human FcαR extracellular domain and rat transmembrane and cytoplasmic domains. In some embodiments, the regulatory regions (e.g., promoters and UTRs) are rodent (e.g., rat) regulatory regions.

NCBI Reference Sequence Number NW_016107304.1 is a representative source sequence of a human FcαR gene. NCBI Reference Sequence Numbers NM_002000.4 and NP_001991.1, NM_133269.4 and NP_579803.1, NM_133271.4 and NP_579805.1, NM_133272.4 and NP 579806.1, NM_133273.4 and NP 579807.1, NM_133274.4 and NP_579808.1, NM 133277.4 and NP_579811.1, NM 133278.4 and NP_579812.1, XM_011526625.3 and XP_011524927.1, XM_017026473.1 and XP_016881962.1, XM_017026474.2 and XP_016881963.1, provide representative source sequences of human FcαR cDNA and polypeptides from which a desired human portion may be obtained.

NCBI Reference Sequence Number NC_005100.4 provides a representative source sequence of a *Rattus norvegicus* FcαR gene and NCBI Reference Sequence Numbers NM_201992.1→NP_973721.1 provide representative source sequences of *Rattus norvegicus* FcαR cDNA and polypeptides from which a desired *Rattus norvegicus* portion may be obtained and/or which can be used in the design of targeting vector homology arms.

In some embodiments, the mouse is heterozygous for the genetically modified FcαR locus. In some embodiments, the mouse is homozygous for the genetically modified FcαR locus.

In various embodiments, the human or humanized FcαR polypeptide described herein is expressed on cell surface in association with a wild type mouse FcR γ chain. In various embodiments, the human or humanized FcαR polypeptide described herein is expressed on cell surface in association with an endogenous mouse FcR γ chain.

Humanized Low Affinity Fc Gamma Receptors

In some embodiments, the mice and ES cells genetically modified to comprise in their genome a humanized or human FcαR1 locus further comprise a locus encoding human low affinity Fc gamma receptor (FcγR) polypeptide (e.g., a human FcγRIIa, FcγRIIb, FcγRIIc, FcγRIIIa or FcγRIIIb polypeptide; see, for example, U.S. Pat. No. 8,658,154, the contents of which are incorporated herein by reference in their entirety).

In some embodiments, the low affinity FcγR locus comprises a nucleic acid sequence encoding a human FcγRIIa polypeptide. In some embodiments, the nucleic acid sequence encoding the human FcγRIIa polypeptide is positioned at an endogenous mouse low affinity FcγR locus. In some embodiments, the nucleic acid sequence encoding the FcγRIIa polypeptide replaces all or part of an endogenous mouse low affinity FcγR locus. In some embodiments, the human FcγRIIa gene comprises a polymorphism, wherein the polymorphism is selected from a 131His low responder polymorphism and a 131Arg high responder polymorphism. In some embodiments, the FcγRIIa polymorphism is the 131His low responder polymorphism. In some embodiments, the mouse does not express a mouse low affinity FcγR polypeptide (e.g., does not express a mouse FcγRIIb, FcγRIV and/or FcγRIII polypeptide, or does not express functional mouse FcγRIIb, FcγRIV and/or FcγRIII polypeptide). In some embodiments, the FcγRIIa gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, the low affinity FcγR locus comprises a nucleic acid sequence encoding a human FcγRIIb polypeptide. In some embodiments, the nucleic acid sequence encoding the human FcγRIIb polypeptide is positioned at an endogenous mouse low affinity FcγR locus. In some embodiments, the nucleic acid sequence encoding the FcγRIIb polypeptide replaces all or part of an endogenous mouse low affinity FcγR locus. In some embodiments, the human FcγRIIb gene comprises an amino acid substitution, wherein the substitution is selected from an 187Ile or a 187Thr substitution. In some embodiments, the mouse does not express a mouse low affinity FcγR polypeptide (e.g., does not express a mouse FcγRIIb, FcγRIV and/or FcγRIII polypeptide, or does not express functional mouse FcγRIIb, FcγRIV and/or FcγRIII polypeptide). In some embodiments, the FcγRIIb gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, the low affinity FcγR locus comprises a nucleic acid sequence encoding a human FcγRIIc polypeptide. In some embodiments, the nucleic acid sequence encoding the human FcγRIIc polypeptide is positioned at an endogenous mouse low affinity FcγR locus. In some embodiments, the nucleic acid sequence encoding the FcγRIIc polypeptide replaces all or part of an endogenous mouse low affinity FcγR locus. In one embodiment, the FcγRIIc gene is a specific allelic variant, wherein the allelic variant is selected from a 57Stop variant and a 57Q variant. In some embodiments, the mouse does not express a mouse low affinity FcγR polypeptide (e.g., does not express a mouse FcγRIIB, FcγRIV and/or FcγRIII polypeptide). In some embodiments, the FcγRIIc gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, the low affinity FcγR locus comprises a nucleic acid sequence encoding a human FcγRIIIa polypeptide. In some embodiments, the nucleic acid sequence encoding the human FcγRIIIa polypeptide is positioned at an endogenous mouse low affinity FcγR locus. In some embodiments, the nucleic acid sequence encoding the FcγRIIIa polypeptide replaces all or part of an endogenous mouse low affinity FcγR locus. In some embodiments, the mouse does not express a mouse low affinity FcγR polypeptide (e.g., does not express a mouse FcγRIIb, FcγRIV and/or FcγRIII polypeptide, or does not express functional mouse FcγRIIb, FcγRIV and/or FcγRIII polypeptide). In one embodiment, the FcγRIIIa gene is a specific allelic variant, wherein the allelic variant is selected from a 176Val variant and a 176Phe variant. In some embodiments, the FcγRIIIa allelic variant is the 176Val variant. In some embodiments, the FcγRIIIa gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, the low affinity FcγR locus comprises a nucleic acid sequence encoding a human FcγRIIIb polypeptide. In some embodiments, the nucleic acid sequence encoding the human FcγRIIIb polypeptide is positioned at an endogenous mouse low affinity FcγR locus. In some embodiments, the nucleic acid sequence encoding the FcγRIIIb polypeptide replaces all or part of an endogenous mouse low affinity FcγR locus. In some embodiments, the FcγRIIIb gene is a specific allelic variant, wherein the allelic variant is selected from a NA1 variant and a NA2 variant. In another specific embodiment, the FcγRIIIb allelic variant is a NA2 variant. In some embodiments, the mouse does not express a mouse low affinity FcγR polypeptide (e.g., does not express a mouse FcγRIIb, FcγRIV and/or FcγRIII poly-peptide, or does not express functional mouse FcγRIIb, FcγRIV and/or FcγRIII polypeptide). In some embodiments, the FcγRIIIb gene locus comprises non-human regulatory elements (e.g., non-human promoters and/or enhancers). In some embodiments, the non-human regulatory elements are mouse regulatory elements (e.g., rat or mouse promoters or enhancers).

In some embodiments, a mouse provided herein com-prises one or more human low affinity FcγR genes as described in U.S. Pat. Nos. 9,221,894, 9,056,130, 9,089,599, 8,658,154, 8,883,496 or 8,658,853, incorporated by refer-ence herein. In some embodiments, a mouse provided herein comprises at least two low affinity human FcγR genes and an endogenous mouse Fc γ-chain gene, wherein the low affinity human FcγR genes are selected from the group consisting of human FcγRIIa, FcγRIIb, FcγRIIc, FcγRIIIa and FcγRIIIb. In some certain embodiments, a mouse provided herein comprises a human FcγRIIa and FcγRIIIb, and an endog-enous mouse Fc γ-chain gene. In some certain embodiments, a mouse provided herein comprises FcγRIIa, FcγRIIIa, FcγRIIb, FcγRIIc and FcγRIIId genes, and an endogenous mouse Fc γ-chain gene. In various embodiments, a mouse comprising one or more human FcγRs further comprises a homozygous disruption in endogenous mouse FcγRIIB, FcγRIV and FcγRIII genes (i.e., endogenous mouse FcγRIIb, FcγRIV and FcγRIII α-chain encoding sequences). In vari-ous embodiments, a mouse comprising one or more human low affinity FcγRs as described herein does not detectably express an endogenous mouse low affinity FcγR polypeptide (e.g., an endogenous low affinity FcγR α-chain polypeptide).

In some embodiments, the mouse is heterozygous for the genetically modified low affinity FcγR locus. In some embodiments, the mouse is homozygous for the genetically modified low affinity FcγR locus.

Humanized Neonatal Fc Receptor Loci

In some embodiments, the mice and ES cells genetically modified to comprise in their genome a humanized or human FcαR1 locus, and in some embodiments a human or human-ized FcγR locus (as described above), further comprise a humanized or human neonatal Fc receptor (FcRn) locus. FcRn, also known as the Brambell receptor, is a protein that is expressed by endothelial cells and associates with beta-2-microglobulin (β2M) and binds to both the Fc domains of IgG antibodies and serum albumin. FcRn extends the half-life of IgG and serum albumin. Specifically, by binding IgG and serum albumin in a pH dependent manner, FcRn is able to rescue these serum proteins from lysosomal degradation by endothelial cells, thereby increasing the serum half-life of such proteins.

In some embodiments, the FcRn locus comprises a nucleic acid sequence encoding an FcRn polypeptide com-prising a human extracellular domain, a rodent (e.g., mouse or rat) transmembrane domain and a rodent (e.g., mouse or rat) cytoplasmic domain. In some embodiments, the FcRn locus comprises a nucleic acid sequence encoding an FcRn polypeptide comprising a human extracellular domain, a human (e.g., mouse or rat) transmembrane domain and a rodent (e.g., mouse or rat) cytoplasmic domain. In some embodiments, the FcRn locus comprises a nucleic acid sequence encoding an FcRn polypeptide comprising a human extracellular domain, a human (e.g., mouse or rat) transmembrane domain and a human (e.g., mouse or rat) cytoplasmic domain.

In some embodiments, the nucleic acid sequence encod-ing the FcRn polypeptide is positioned at an endogenous mouse FcRn locus. In certain embodiments, the nucleic acid sequence encoding the FcRn polypeptide replaces all or part of an endogenous mouse FcRn gene. For example, in some embodiments, the nucleic acid sequence encoding the extra-cellular domain of an endogenous FcRn at an endogenous FcRn locus is replaced with a nucleic acid sequence encod-ing the extracellular domain of a human FcRn such that a mouse comprising such a locus expresses an FcRn with a human extracellular domain and a rodent (e.g., rat or mouse) transmembrane and cytoplasmic domain. In some embodi-ments, the mouse does not express a mouse FcRn, or does not express a functional mouse FcRn. In some embodiments, the FcRn gene locus comprises non-human regulatory ele-ments (e.g., non-human promoters and/or enhancers). In some embodiments, the non-human regulatory elements are rodent regulatory elements (e.g., rat or mouse promoters or enhancers).

In certain embodiments, the mouse exons encoding alpha 1, alpha 2, and alpha 3 domains (exons 3, 4, and 5, which are the first three coding exons) of the mouse FcRn gene are replaced with human exons encoding alpha 1, alpha 2, and alpha 3 domains (exons 3, 4, and 5) of the human FcRn gene. In some embodiments, the FcRn gene comprises mouse exon 1 (non-coding exon), mouse exon 2 (comprising nucleic acid sequence encoding the signal peptide), and human exons 3-6, mouse exons 6 and 7 (encoding trans-membrane and cytoplasmic domains). Exemplary human-ized FcRn locus is described in WO2019/190990 (e.g., in FIG. 4), incorporated herein by reference.

GenBank accession nos. NC_000019.10 (49512279-49526428), NM_001136019.1, and NP_001129491.1 pro-vide representative source sequences of a human FcRn gene, cDNA and polypeptide from which a desired human portion may be obtained. GenBank accession nos. NC_000073.6 (45092992-45103846), NM_010189.1, and NP_034319.1 provide representative source sequences of a mouse FcRn gene, cDNA and polypeptide from which a desired mouse portion may be obtained and/or which can be used in the design of targeting vector homology arms.

In some embodiments, the mouse is heterozygous for the genetically modified FcRn locus. In some embodiments, the mouse is homozygous for the genetically modified FcRn locus.

Humanized Fc Epsilon Receptor 1 Alpha

In some embodiments, the mice and ES cells genetically modified to comprise in their genome a humanized or human FcαR1 locus, and in some embodiments a human or human-ized FcγR locus (as described above), further comprise a humanized or human Fc epsilon receptor 1 alpha (FcεR1α) locus. FcεR1a associates with FcεR1β and FcεR1γ to form FcεR1, a high-affinity receptor for IgE that is expressed on epidermal Langerhans cells, eosinophils, mast cells and basophils. The IgE binding site of FcεR1 is found in the FcεR1α subunit.

In some embodiments, the FcεR1α locus comprises a nucleic acid sequence encoding an FcεR1α polypeptide comprising a human extracellular domain, a rodent (e.g., mouse or rat) transmembrane domain and a rodent (e.g., mouse or rat) cytoplasmic domain. In some embodiments, the FcεR1α locus comprises a nucleic acid sequence encod-ing an FcεR1α polypeptide comprising a human extracel-lular domain, a human transmembrane domain and a rodent (e.g., mouse or rat) cytoplasmic domain. In some embodi-ments, the FcεR1α locus comprises a nucleic acid sequence encoding an FcεR1α polypeptide comprising a human extra-cellular domain, a human transmembrane domain and a human cytoplasmic domain. An exemplary embodiment of an engineered FcεR1α locus is described in WO2019/190990, incorporated herein by reference.

In some embodiments, the nucleic acid sequence encoding the FcεR1α polypeptide is positioned at an endogenous mouse FcεR1α locus. In certain embodiments, the nucleic acid sequence encoding the FcεR1α polypeptide replaces all or part of an endogenous mouse FcεR1α gene. For example, in some embodiments, the nucleic acid sequence encoding the extracellular domain of an endogenous FcεR1α at an endogenous FcεR1α locus is replaced with a nucleic acid sequence encoding the extracellular domain of a human FcεR1α such that a mouse comprising such a locus expresses a FcεR1α with a human extracellular domain and a rodent (e.g., rat or mouse) transmembrane and cytoplasmic domain. In some embodiments, the nucleic acid sequence encoding an FcεR1α polypeptide comprising a human extracellular domain, a human transmembrane domain, and a human cytoplasmic domain is positioned at an endogenous mouse FcεR1α locus. In some embodiments, the nucleic acid sequence encoding a FcεR1α polypeptide comprising a human extracellular domain, a human transmembrane domain, and a human cytoplasmic domain replaces all or part of an endogenous mouse FcεR1α gene. In some embodiments, the mouse does not express a mouse FcεR1α, or does not express a functional mouse FcεR1α. In some embodiments, the FcεR1α gene locus comprises non-human regulatory elements (e.g., non-human promoters and/or enhancers). In some embodiments, the non-human regulatory elements are rodent regulatory elements (e.g., rat or mouse promoters or enhancers).

In certain embodiments, part of mouse coding exon 1, coding exon 2, coding exon 3, coding exon 4, and coding exon 5 of the mouse FcεR1α are replaced by part of human coding exon 1, coding exon 2, coding exon 3, coding exon 4, and coding exon 5 of the human FcεR1α gene. In some embodiments, the FcεR1α gene comprises chimeric mouse/human exon 1 (comprising mouse promoter and 5' UTR), human coding exons 2-5 through the stop codon, human 3'UTR and polyA, followed by the mouse 3'UTR and polyA. In some embodiments, chimeric gene exons 1 (partial) and 2 encode the signal peptide, exon 3 and 4 encode the two Ig-like domains of FcεR1α that are believed to interact with IgE, and exon 5 encodes the cytoplasmic and transmembrane domains of the protein (see FIG. 9 of WO2019/190990).

GenBank accession nos. NC_000001.11 (159283888-159308224), NM_002001.3, and NP_001992.1 provide representative source sequences of a human FcεR1α gene, cDNA and polypeptide from which a desired human portion may be obtained. GenBank accession nos. NC_000067.6 (173221269-173227232), NM_010184.1, and NP_034314.1 provide representative source sequences of a mouse FcεR1α gene, cDNA and polypeptide from which a desired mouse portion may be obtained and/or which can be used in the design of targeting vector homology arms.

In some embodiments, the mouse is heterozygous for the genetically modified FcεR1α locus. In some embodiments, the mouse is homozygous for the genetically modified FcεR1α locus.

Humanized Fc Gamma Receptor 1a

In some embodiments, the mice and ES cells genetically modified to comprise in their genome a humanized or human FcαR1 locus further comprise a humanized or human Fc gamma receptor 1a (FcγR1a) locus. FcγR1a is a high affinity FcγR protein expressed on monocytes that binds to the Fc portion of IgG and causes activation of the host cell.

In some embodiments, the FcγR1a locus comprises a nucleic acid sequence encoding a FcγR1a polypeptide comprising a human extracellular domain, a rodent (e.g., mouse or rat) transmembrane domain and a rodent (e.g., mouse or rat) cytoplasmic domain. In some embodiments, the FcγR1a locus comprises a nucleic acid sequence encoding a FcγR1a polypeptide comprising a human extracellular domain, a human (e.g., mouse or rat) transmembrane domain and a rodent (e.g., mouse or rat) cytoplasmic domain. In some embodiments, the FcγR1a locus comprises a nucleic acid sequence encoding a FcγR1a polypeptide comprising a human extracellular domain, a human (e.g., mouse or rat) transmembrane domain and a human (e.g., mouse or rat) cytoplasmic domain.

In some embodiments, the nucleic acid sequence encoding the FcγR1a polypeptide is positioned at an endogenous mouse FcγR1a locus. In certain embodiments, the nucleic acid sequence encoding the FcγR1a polypeptide replaces all or part of an endogenous mouse FcγR1a gene. For example, in some embodiments, the nucleic acid sequence encoding the extracellular domain of an endogenous FcγR1a at an endogenous FcγR1a locus is replaced with a nucleic acid sequence encoding the extracellular domain of a human FcγR1a such that a mouse comprising such a locus expresses a FcγR1a with a human extracellular domain and a rodent (e.g., rat or mouse) transmembrane and cytoplasmic domain. In some embodiments, the mouse does not express a mouse FcγR1a, or does not express a functional mouse FcγR1a. In some embodiments, the FcγR1a gene locus comprises non-human regulatory elements (e.g., non-human promoters and/or enhancers). In some embodiments, the non-human regulatory elements are rodent regulatory elements (e.g., rat or mouse promoters or enhancers).

Humanized FcγR1a polypeptides, loci encoding humanized FcγR1a polypeptides and mice expressing humanized FcγR1a polypeptides are described in U.S. Pat. No. 9,474,255 and U.S. Pat. Pub. No. 2017/0086432, each of which is incorporated by reference herein.

In some embodiments, the mouse is heterozygous for the genetically modified FcγR1a locus. In some embodiments, the mouse is homozygous for the genetically modified FcγR1a locus.

Humanized Immunoglobulin Heavy Chain Loci

As discussed herein above, in certain embodiments the mice provided herein that express a human FcαR are used to test agents comprising a human Fc (e.g., agents comprising a human Fcα, such as therapeutic human IgA antibodies and human Fcα fusion proteins). However, when therapeutic agents with human Fc regions are administered to wild type mice, the human sequences in the Fc regions are often identified as foreign by the mouse immune system. As a consequence, the mouse may mount an immune response against the administered therapeutic agents (known as mouse anti-human response or MAHA), which affects the pharmacokinetic and pharmacodynamic properties of the administered agents. As disclosed in WO2019/190990, which is hereby incorporated by reference in its entirety, testing therapeutic agents comprising a human Fc in mice having human immunoglobulin locus regions can reduce or eliminate MAHA responses because the human Fc is less likely to be identified by foreign in such mice.

In some embodiments, the mice and ES cells genetically modified to comprise in their genome a humanized or human FcαR1 locus, and optionally, a human or humanized FcγR locus, a human or humanized Igκ locus, a human or humanized Igλ locus, a human or humanized FcRn locus, a human or humanized β2M locus, and/or a human or humanized FcεR1α locus, further comprise a genetically modified immunoglobulin (Ig) heavy chain loci. Such loci generally comprise a variable region and a constant region. The variable region includes Ig heavy chain variable region gene segments (e.g., at least a $V_H$ gene segment, a $D_H$ gene segment and a $J_H$ gene segment). The constant region locus includes one or more Ig heavy chain constant region gene segments ($C_H$). In certain embodiments the immunoglobulin heavy chain variable region is operably linked to the immunoglobulin heavy chain constant region such that the mouse produces antibodies comprising variable domains derived from the $V_H$ gene segment, the $D_H$ gene segment and the $J_H$ gene segment and heavy chain constant domains derived from the $C_H$ gene segment.

The ability to generate antibodies has been harnessed in genetically modified animals to generate therapeutic antibodies against human targets. Exemplary genetically modified mice, comprising human V(D)J gene segments, for generation of therapeutic antibodies are those described in U.S. Pat. Nos. 5,633,425, 5,770,429, 5,814,318, 6,075,181, 6,114,598, 6,150,584, 6,998,514, 7,795,494, 7,910,798, 8,232,449, 8,703,485, 8,907,157, and 9,145,588, each of which is hereby incorporated by reference in its entirety, as well as in U.S. Pat. Pub. Nos. 2008/0098490, 2010/0146647, 2013/0145484, 2012/0167237, 2013/0167256, 2013/0219535, 2012/0207278, and 2015/0113668, each of which is hereby incorporated by reference in its entirety, and in PCT Pub. Nos. WO2007117410, WO2008151081, WO2009157771, WO2010039900, WO2011004192, WO2011123708, WO2014093908, WO2014093908, WO2006008548, WO2010109165, WO2016062990, WO2018039180, WO2011158009, WO2013041844, WO2013041846, WO2013079953, WO2013061098, WO2013144567, WO2013144566, WO2013171505, and WO2019008123, each of which are hereby incorporated by reference in its entirety. Other exemplary genetically modified mice, comprising human V(D)J gene segments, for generation of therapeutic antibodies are those described in U.S. Pat. Nos. 6,596,541, 6,586,251, 8,642,835, 9,706,759, 10,238,093, 8,754,287, 10,143,186, 9,796,788, 10,130,081, 9,226,484, 9,012,717, 10,246,509, 9,204,624, and 9,686,970, and each of which is hereby incorporated by reference in its entirety, as well as in U.S. Pat. Pub. Nos. 2013/0212719, 2015/0289489, 2017/0347633, 2019/0223418, 2018/0125043, 2019/0261612, and 2019/0380316, each of which is hereby incorporated by reference in its entirety, in PCT Pub. Nos. WO2013138680, WO2013138712, WO2013138681, WO2015042250, WO2012148873, WO2013134263, WO2013184761, WO2014160179, WO2017214089, WO2016149678, and WO2017123808, and Murphy, A., "VelocImmune: Immunoglobulin Variable Region Humanized Mouse," in *Recombinant Antibodies for Immunotherapy*, New York, NY, Cambridge University Press, 101-107 (2009), each of which are hereby incorporated by reference in its entirety.

In certain embodiments, the Ig heavy chain variable region locus contains unrearranged human Ig heavy chain variable region gene segments. In some embodiments, the unrearranged human Ig variable region gene segments comprise one or more human $V_H$ segments, one or more human $D_H$ segments and one or more human $J_H$ segments. In some embodiments, the unrearranged human Ig variable region gene segments comprise at least 3 $V_H$ gene segments, at least 18 $V_H$ gene segments, at least 20 $V_H$ gene segments, at least 30 $V_H$ gene segments, at least 40 $V_H$ gene segments, at least 50 $V_H$ gene segments, at least 60 $V_H$ gene segments, at least 70 $V_H$ gene segments, or at least 80 $V_H$ gene segments. In some certain embodiments, an engineered IgH locus (or allele) comprises all or substantially all the functional human $V_H$ gene segments found between human $V_H3$-74 and human $V_H6$-1 gene segments, inclusive, of a human IgH locus that appears in nature. In some certain embodiments, an engineered IgH locus (or allele) comprises at least human $V_H$ gene segments $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2 and $V_H6$-1. In some embodiments, the mice provided herein have a restricted immunoglobulin heavy chain locus characterized by a single polymorphic human $V_H$ gene segment, a plurality of $D_H$ gene segments and a plurality of $J_H$ gene segments (e.g., as described in U.S. Pat. Pub. No. 2013/0096287, which is hereby incorporated by reference). In some embodiments, the $V_H$ gene segment is $V_H1$-2 or $V_H1$-69. In some embodiments, the mice provided herein have a rearranged heavy chain variable region (a universal heavy chain variable region or a common heavy chain encoding sequence, e.g., as described in U.S. Patent Pub. No. 20140245468 and U.S. Pat. Nos. 9,204,624 and 9,930,871, each of which is hereby incorporated by reference herein in its entirety). In some embodiments, the mice provided herein comprise human unrearranged immunoglobulin light chain, e.g., κ, gene segments operably linked to a heavy chain constant region gene at the immunoglobulin heavy chain locus (e.g., U.S. Pat. No. 9,516,868, incorporated herein by reference in its entirety).

In yet other embodiments, the mouse may comprise in its germline and/or genome a heavy chain immunoglobulin locus that includes insertions and/or replacements of histidine codons designed to introduce pH-dependent binding properties to the antibodies generated in such mice. In some of such embodiments, the histidine codons are inserted and/or replaced in the nucleic acid sequences encoding CDR3. Various such heavy immunoglobulin loci are provided in U.S. Pat. Nos. 9,301,510, 9,334,334, U.S. Patent Application Publication Nos. 2013/0247236, 20140013456, incorporated herein by reference.

In some embodiments, an engineered IgH locus (or allele) comprises 5, 10, 15, 20, 25 or more (e.g., 26, 27, etc.) human $D_H$ gene segments. In some certain embodiments, an engineered IgH locus (or allele) comprises all or substantially all of the functional human $D_H$ gene segments found between a human $D_H1$-1 and human $D_H7$-27 gene segment, inclusive, of a human IgH locus that appears in nature. In some certain embodiments, an engineered IgH locus (or allele) comprises at least human $D_H$ gene segments $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26 and $D_H7$-27. In some embodiments, the unrearranged human Ig gene segments include all of the human $D_H$ gene segments.

In some embodiments, an engineered IgH locus (or allele) comprises 1, 2, 3, 4, 5, 6 or more functional human $J_H$ gene segments. In some certain embodiments, an engineered IgH locus (or allele) comprises all or substantially all the functional human $J_H$ gene segments found between human $J_H1$ and human $J_H6$ gene segments, inclusive, of a human IgH locus that appears in nature. In some certain embodiments, an engineered IgH locus (or allele) comprises at least human $J_H$ gene segments $J_H1$, $J_H2$, $J_H3$, $J_H4$, $J_H5$ and $J_H6$. In some embodiments, the unrearranged human Ig gene segments include all of the human $J_H$ gene segments.

In some embodiments, an engineered IgH locus as described herein does not contain an endogenous Adam6 gene. In some embodiments, an engineered IgH locus as described herein does not contain an endogenous Adam6 gene (or Adam6-encoding sequence) in the same germline genomic position as found in a germline genome of a wild-type non-human animal of the same species. In some embodiments, an engineered IgH locus as described herein does not contain a human Adam6 pseudogene. In some embodiments, an engineered IgH locus as described herein comprises insertion of at least one nucleotide sequence that encodes one or more non-human (e.g., mouse) Adam6 polypeptides. Said insertion may be outside of an engineered immunoglobulin heavy chain locus as described herein (e.g., upstream of a 5' most $V_H$ gene segment), within an engineered IgH locus or elsewhere in the germline genome of a non-human animal (e.g., a randomly introduced non-human Adam6-encoding sequence), cell or tissue.

In some embodiments, an engineered endogenous immunoglobulin heavy chain locus lacks a functional endogenous mouse Adam6 gene. In some embodiments, a germline genome of a mouse comprising the engineered heavy chain locus includes one or more nucleotide sequences encoding one or more mouse ADAM6 polypeptides, functional orthologs, functional homologs, or functional fragments thereof. In some embodiments, one or more mouse ADAM6 polypeptides, functional orthologs, functional homologs, or functional fragments thereof are expressed (e.g., in a cell of the male reproductive system, e.g., a testes cell).

In some embodiments, one or more nucleotide sequences encoding one or more mouse ADAM6 polypeptides, functional orthologs, functional homologs, or functional fragments thereof are included on the same chromosome as the engineered endogenous immunoglobulin heavy chain locus. In some embodiments, one or more nucleotide sequences encoding one or more mouse ADAM6 polypeptides, functional orthologs, functional homologs, or functional fragments thereof are included in the engineered endogenous immunoglobulin heavy chain locus. In some embodiments, one or more nucleotide sequences encoding one or more mouse ADAM6 polypeptides, functional orthologs, functional homologs, or functional fragments thereof are between a first human $V_H$ gene segment and a second human $V_H$ gene segment. In some embodiments, a first human $V_H$ gene segment is $V_H$1-2 and a second human $V_H$ gene segment is $V_H$6-1. In some embodiments, one or more nucleotide sequences encoding one or more mouse ADAM6 polypeptides, functional orthologs, functional homologs, or functional fragments thereof are in place of a human Adam6 pseudogene. In some embodiments, one or more nucleotide sequences encoding one or more mouse ADAM6 polypeptides, functional orthologs, functional homologs, or functional fragments thereof replace a human Adam6 pseudogene. In some embodiments, one or more nucleotide sequences encoding one or more mouse ADAM6 polypeptides, functional orthologs, functional homologs, or functional fragments thereof are between a human $V_H$ gene segment and a human $D_H$ gene segment.

Exemplary Ig variable regions comprising Ig heavy chain gene segments are provided, for example, in Macdonald et al., *Proc. Natl. Acad. Sci. USA* 111:5147-52 and supplemental information, which is hereby incorporated by reference. Such mice are described, e.g., U.S. Pat. Nos. 8,642,835 and 8,697,940, incorporated herein by reference.

In some embodiments, the Ig heavy chain variable gene locus comprising unrearranged human Ig heavy chain variable region gene segments also includes human Ig heavy chain variable region intergenic sequences. In some embodiments, the Ig heavy chain variable gene locus includes non-human (e.g., rodent, rat, mouse) Ig heavy chain variable region intergenic sequences. In some embodiments, the IgH locus comprises non-human regulatory elements (e.g., non-human promoters and/or enhancers). In some embodiments, the non-human regulatory elements are rodent regulatory elements (e.g., rat or mouse promoters or enhancers). In some embodiments, the IgH locus comprises an IgM enhancer (Eμ). In some embodiments, the IgM enhancer is a non-human Eμ (e.g., a rodent Eμ, such as a mouse or rat Eμ).

In some embodiments, the Ig heavy chain variable region is a rearranged variable region comprising an Ig heavy chain variable region gene (a universal heavy chain variable region). In some embodiments, the rearranged Ig heavy chain variable region gene is a human rearranged Ig heavy chain variable region gene. Exemplary rearranged Ig heavy chain variable regions are provided in U.S. Patent Pub. No. 2014/0245468, which is hereby incorporated by reference.

In certain embodiments, the mice provided herein comprise a human immunoglobulin constant region (e.g., a human Cc constant region) such that they express antibodies comprising a human Fc (e.g., a human Fax). Mice comprising human immunoglobulin constant regions are disclosed, for example, in WO2019/190990, which is hereby incorporated by reference in its entirety.

In certain embodiments, the immunoglobulin constant region comprises a $C_H$ gene segment encoding an IgG constant domain comprising a human $C_H$1 domain, a human hinge region, a human $C_H$2 domain, a human $C_H$3 domain, an IgG transmembrane domain and an IgG cytoplasmic domain. In some embodiments, the IgG transmembrane domain is a rodent IgG transmembrane domain (e.g., a mouse or rat transmembrane domain). In certain embodiments, transmembrane domain is a human IgG transmembrane domain. In some embodiments, the IgG cytoplasmic domain is a rodent IgG cytoplasmic domain (e.g., a mouse or rat cytoplasmic domain). In some embodiments, the IgG cytoplasmic domain is a human IgG cytoplasmic domain. In some embodiments, the IgG connecting region is a rodent IgG connecting region (e.g., a mouse or rat connecting domain). In certain embodiments, IgG connecting region is a human IgG connecting region.

In certain embodiments, the human $C_H$1 domain, the human hinge region, the human $C_H$2 domain and the human $C_H$3 domain are IgG1 domains. In some embodiments, such an IgG1 domain is encoded by an allele selected from IGHG1*01, IGHG1*02, IGHG1*03, IGHG1*04 and IGHG1*05.

In certain embodiments, the human $C_H$1 domain, the human hinge region, the human $C_H$2 domain and the human $C_H$3 domain are IgG2 domains. In some embodiments, such an IgG2 domain is encoded by an allele selected from IGHG2*01, IGHG2*02, IGHG2*03, IGHG2*04, IGHG2*05 and IGHG2*06.

In certain embodiments, the human $C_H$1 domain, the human hinge region, the human $C_H$2 domain and the human $C_H$3 domain are IgG3 domains. In some embodiments, such an IgG3 domain is encoded by an allele selected from IGHG3*01, IGHG3*02, IGHG3*03, IGHG3*04, IGHG3*05, IGHG3*06, IGHG3*07, IGHG3*08, IGHG3*09, IGHG3*10, IGHG3*11, IGHG3*12, IGHG3*13, IGHG3*14, IGHG3*15, IGHG3*16, IGHG3*17, IGHG3*18 and IGHG3*19.

In certain embodiments, the human $C_H$1 domain, the human hinge region, the human $C_H$2 domain and the human $C_H3$ domain are IgG4 domains. In some embodiments, such an IgG4 domain is encoded by an allele selected from IGHG4*01, IGHG4*02, IGHG4*03 and IGHG4*04.

In some embodiments, the $C_H$ gene segment encodes variant human immunoglobulin heavy chain constant region sequence (i.e., a human immunoglobulin heavy chain constant region sequence that includes one or more additions, deletions, and/or substitutions relative to an appropriate reference human immunoglobulin heavy chain constant region sequence) that is characterized in that effector function and/or affinity for an FcR is enhanced or diminished relative to a reference human immunoglobulin heavy chain constant region.

In some embodiments, the $C_H$ gene segment encodes a human immunoglobulin heavy chain constant region characterized by an altered affinity for activating and/or inhibitory receptors. In some embodiments, the $C_H$ gene segment encodes a human immunoglobulin heavy chain constant region characterized by enhanced or diminished binding to an FcRn receptor, e.g., at acidic pH as compared to neutral pH. In some embodiments, the $C_H$ gene segment encodes a human immunoglobulin heavy chain constant region, in whole or in part, encodes a human immunoglobulin heavy chain constant region having one or more amino acid modifications. Exemplary amino acid modifications include, but are not limited to, a substitution at position 297 (e.g., N297A), position 250 (e.g., 250E or 250Q), position 252 (e.g., 252L, 252Y, 252F, 252W or 252T), position 254 (e.g., 254S or 254T), position 256 (e.g., 256S, 256R, 256Q, 256E, 256D, or 256T), position 307 (e.g., 307P or 307A), position 308 (e.g., 308F or 308V), position 428 (e.g., 428L or 428F), position 433 (e.g., 433H, 433Lm, 433R, 433S, 433P, 433Q or 433K), position 434 (e.g., 434A, 434W, 434H, 434F or 434Y), and combinations thereof. In some embodiments, the $C_H$ gene segment encodes a human immunoglobulin heavy chain constant region having one or more pairs or groups of amino acid modifications selected from the group consisting of 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F).

In some embodiments, the $C_H$ gene segment encodes a chimeric immunoglobulin heavy chain constant domain that includes segments or portions derived from (or that appear in) more than one human immunoglobulin isotypes. For example, such a chimeric $C_H$ region may comprise a $C_H2$ domain derived from a human IgG1, human IgG2 or human IgG4 molecule, combined with a $C_H3$ domain derived from a human IgG1, human IgG2 or human IgG4 molecule. In some certain embodiments, the chimeric $C_H$ region further comprises a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. In some certain embodiments, a chimeric hinge region comprises amino acid residues derived from a human IgG1 or a human IgG4 upper hinge and amino acid residues derived from a human IgG2 lower hinge.

In certain embodiments, the modified $C_H$ gene segment is located at an endogenous $C_H$ gene segment locus. In certain embodiments, the modified $C_H$ gene segment is located at an endogenous $C_{\gamma1}$ gene segment locus, an endogenous $C_{\gamma2a}$ gene segment locus, an endogenous $C_{\gamma2b}$ gene segment locus, an endogenous $C_{\gamma2c}$ gene segment locus or an endogenous $C_{\gamma3}$ gene segment locus.

In some embodiments, the modified $C_H$ gene segment is a human $C_{\gamma1}$ gene segment (or at least the portion of the human $CC_{\gamma1}$ gene segment encoding the $C_H1$ domain, the hinge region, the $C_H2$ domain and the $C_H3$ domain of the IgG1 constant domain) and it is positioned at an endogenous $C_{\gamma2a}$ gene segment locus. In some embodiments, the portion of the human $C_{\gamma1}$ gene segment encoding the $C_H1$ domain, the hinge region, the $C_H2$ domain and the $C_H3$ domain of the IgG1 constant domain is operably linked to the portion of the endogenous mouse $C_{\gamma2a}$ gene segment encoding the IgG2a transmembrane and/or cytoplasmic domain.

In some embodiments, the modified $C_H$ gene segment is a human $C_{\gamma1}$ gene segment (or at least the portion of the human $C_{\gamma1}$ gene segment encoding the $C_H1$ domain, the hinge region, the $C_H2$ domain and the $C_H3$ domain of the IgG1 constant domain) and it is positioned at an endogenous $C_{\gamma2c}$ gene segment locus. In some embodiments, the portion of the human $C_{\gamma1}$ gene segment encoding the CHI domain, the hinge region, the $C_H2$ domain and the $C_H3$ domain of the IgG1 constant domain is operably linked to the portion of the endogenous mouse $C_{\gamma2c}$ gene segment encoding the IgG2c transmembrane and/or cytoplasmic domain.

In some embodiments, the modified $C_H$ gene segment is a human $C_{\gamma4}$ gene segment (or at least the portion of the human $C_{\gamma4}$ gene segment encoding the $C_H1$ domain, the hinge region, the $C_H2$ domain and the $C_H3$ domain of the IgG4 constant domain) and it is positioned at an endogenous $C_{\gamma1}$ gene segment locus. In some embodiments, the portion of the human $C_{\gamma4}$ gene segment encoding the $C_H1$ domain, the hinge region, the $C_H2$ domain and the $C_H3$ domain of the IgG4 constant domain is operably linked to the portion of the endogenous mouse $C_{\gamma1}$ gene segment encoding the IgG1 transmembrane and/or cytoplasmic domain.

In certain embodiments, the modified $C_H$ gene segment replaces all or part of an endogenous $C_H$ gene segment. In certain embodiments, the modified $C_H$ gene segment replaces all or part of an endogenous $C_{\gamma1}$ gene segment, an endogenous $C_{\gamma2a}$ gene segment, an endogenous $C_{\gamma2b}$ gene segment, an endogenous $C_{\gamma2c}$ gene segment, or an endogenous $C_{\gamma3}$ gene segment.

In some embodiments, the modified $C_H$ gene segment is a human $C_{\gamma1}$ gene segment (or at least the portion of the human $C_{\gamma1}$ gene segment encoding the CHI domain, the hinge region, the $C_H2$ domain and the $C_H3$ domain of the IgG1 constant domain) and it replaces all or part of an endogenous $C_{\gamma2a}$ gene segment locus. In some embodiments, the portion of the human $C_{\gamma1}$ gene segment encoding the $C_H1$ domain, the hinge region, the $C_H2$ domain and the $C_H3$ domain of the IgG1 constant domain replaces the portion of the endogenous mouse $C_{\gamma2a}$ gene segment encoding the $C_H1$ domain, the hinge region, the $C_H2$ domain and the $C_H3$ domain of the IgG2a constant domain such that the portion of the human $C_{\gamma1}$ gene segment encoding the $C_H1$ domain, the hinge region, the $C_H2$ domain and the $C_H3$ domain of the IgG1 constant domain is operably linked to the portion of the endogenous mouse $C_{\gamma2a}$ gene segment encoding the IgG2a transmembrane and/or cytoplasmic domain.

In some embodiments, the modified $C_H$ gene segment is a human $C_{\gamma4}$ gene segment (or at least the portion of the human $C_{\gamma4}$ gene segment encoding the $C_H1$ domain, the hinge region, the $C_H2$ domain and the $C_H3$ domain of the IgG4 constant domain) and it replaces all or part of an endogenous $C_{\gamma 1}$ gene segment locus. In some embodiments, the portion of the human $C_{\gamma 4}$ gene segment encoding the $C_H1$ domain, the hinge region, the $C_H2$ domain and the $C_H3$ domain of the IgG4 constant domain replaces the portion of the endogenous mouse $C_{\gamma 1}$ gene segment encoding the $C_H1$ domain, the hinge region, the $C_H2$ domain and the $C_H3$ domain of the IgG1 constant domain such that the portion of the human $C_{\gamma 4}$ gene segment encoding the $C_H1$ domain, the hinge region, the $C_H2$ domain and the $C_H3$ domain of the IgG4 constant domain is operably linked to the portion of the endogenous mouse $C_{\gamma 1}$ gene segment encoding the IgG1 transmembrane and/or cytoplasmic domain.

In certain embodiments the Ig heavy chain constant region includes one or more rodent (e.g., rat or mouse) $C_H$ gene segments. In some embodiments, the Ig constant region includes a rodent (e.g., rat or mouse) $C_\mu$ gene segment. In some embodiments, the Ig constant region includes a rodent (e.g., rat or mouse) $C_\delta$ gene segment. In some embodiments, the Ig constant region includes a rodent (e.g., rat or mouse) $C_{\gamma 1}$ gene segment. In some embodiments, the Ig constant region includes a rodent (e.g., rat or mouse) $C_{\gamma 2a}$ gene segment. In some embodiments, the Ig constant region includes a rodent (e.g., rat or mouse) $C_{\gamma 2b}$ gene segment. In some embodiments, the Ig constant region includes a rodent (e.g., rat or mouse) $C_{\gamma 2c}$ gene segment. In some embodiments, the Ig constant region includes a rodent (e.g., mouse) $C_{\gamma 3}$ gene segment. In some embodiments, the Ig constant region includes a rodent (e.g., rat or mouse) $C_\varepsilon$ gene segment. In some embodiments, the Ig constant region includes a rodent (e.g., rat or mouse) $C_\varepsilon$ gene segment. In some embodiments, the one or more rodent constant region gene segments are endogenous constant region gene segments. In some embodiments, the modified $C_H$ gene segment described above is the only modified $C_H$ gene segment in the Ig heavy chain constant region. In some embodiments, the modified $C_H$ gene segment described above is one of a plurality of modified $C_H$ gene segments in the Ig heavy chain constant region (e.g., one of 2, 3, 4, 5, 6, 7 or 8 modified gene segments that are partially or fully humanized in the Ig heavy chain constant region). In some embodiments, the Ig heavy chain constant region includes a human or partially human $C_\mu$ gene segment. In some embodiments, the Ig heavy chain constant region includes a human or partially human $C_\delta$ gene segment. In some embodiments, the Ig heavy chain constant region includes a human or partially human $C_{\gamma 1}$ gene segment. In some embodiments, the Ig heavy chain constant region includes a human or partially human $C_{\gamma 2}$ gene segment. In some embodiments, the Ig heavy chain constant region includes a human or partially human $C_{\gamma 3}$ gene segment. In some embodiments, the Ig heavy chain constant region includes a human or partially human $C_{\gamma 4}$ gene segment. In some embodiments, the Ig heavy chain constant region includes a human or partially human $C_\varepsilon$ gene segment. In some embodiments, the Ig heavy chain constant region includes a human or partially human $C_\alpha$ gene segment. In some embodiments, the Ig heavy chain constant region comprises a human $C_\mu$ gene segment, a human $C_\delta$ gene segment, a human $C_{\gamma 1}$ gene segment and a human $C_{\gamma 3}$ gene segment. In some embodiments, the Ig heavy chain constant region further comprises a human $C_{\gamma 2}$ gene segment and a human $C_{\gamma 4}$ gene segment. In some embodiments, the Ig heavy chain constant region further comprises a human $C_\alpha$ gene segment. In some embodiments, the Ig heavy chain constant region further comprises a human $C_\varepsilon$ gene segment.

In some embodiments, the IgH locus comprises human or rodent (e.g., rat or mouse) regulatory elements. In some embodiments, the regulatory element is an endogenous regulatory element. In certain embodiments, the IgH locus comprises a rodent (e.g., rat or mouse) or human intronic enhancer ($E_i$). In some embodiments, the IgH locus comprises a rodent (e.g., rat or mouse) or human 3' regulatory region (3' RR).

In some embodiments, the modified immunoglobulin heavy chain locus is positioned at an endogenous immunoglobulin heavy chain locus. In some embodiments, the immunoglobulin heavy chain locus replaces all or part of the endogenous immunoglobulin heavy chain locus. In certain embodiments, the modified IgH locus is located on a transgene positioned outside of the endogenous locus. In some embodiments, the endogenous IgH locus is inactivated (e.g., through the deletion, relocation and/or inversion of all or part of the endogenous Ig heavy chain locus).

Thus, in some embodiments, one or more immunoglobulin heavy chain constant regions (or portion thereof) of an immunoglobulin heavy chain locus are not deleted (i.e., intact). In some embodiments, one or more $C_H$ gene segments of an immunoglobulin heavy chain locus are altered, disrupted, deleted or replaced with, among other things, an immunoglobulin heavy chain constant region sequence as described herein (e.g., a sequence encoding a human IgG $C_H1$-H-$C_H2$-$C_H3$ polypeptide) operably linked to a transmembrane and cytoplasmic encoding sequence(s) of a non-human immunoglobulin heavy chain IgG constant region gene (e.g., an M1 and/or M2 encoding sequence) and, in some embodiments, an immunoglobulin heavy chain constant region sequence (e.g., a sequence encoding a human IgE $C_H1$-$C_H2$-$C_H3$-$C_H4$ polypeptide) operably linked to a transmembrane and cytoplasmic encoding sequence(s) an IgE constant region gene. In some embodiments, all or substantially all of an immunoglobulin heavy chain constant region is replaced with a heterologous immunoglobulin heavy chain constant region. In some embodiments, a heterologous immunoglobulin heavy chain constant region sequence is operably linked to a transmembrane and cytoplasmic encoding sequence (e.g., M1 and M2 exons) of one or more IgG constant region gene. In some embodiments, a heterologous immunoglobulin heavy chain constant region sequence is operably linked to a transmembrane and cytoplasmic encoding sequence (e.g., M1 and M2 exons) of an IgE constant region gene. In some embodiments, a heterologous immunoglobulin heavy chain constant region sequence is operably linked to a transmembrane and cytoplasmic encoding sequence (e.g., an M exon[s]) of an IgA constant region gene. In some certain embodiments, one or more $C_H$ gene segments (e.g., $C_\mu$, $C_\delta$, etc.) are not deleted or replaced in an immunoglobulin heavy chain constant region that includes a heterologous immunoglobulin heavy chain constant region sequence operably linked to a transmembrane and cytoplasmic encoding sequence of one or more constant region genes as described herein. In some embodiments, a heterologous immunoglobulin heavy chain constant region sequence is a human immunoglobulin heavy chain constant region sequence. In some embodiments, an immunoglobulin heavy chain constant region that is altered, disrupted, deleted, replaced or engineered with one or more heterologous immunoglobulin heavy chain constant region sequences is a murine immunoglobulin heavy chain constant region. In some embodiments, a heterologous immunoglobulin heavy chain constant region sequence is inserted into one copy (i.e., allele) of an IgG constant region gene (e.g., $C_{\gamma 1}$, $C_{\gamma 2a}$, $C_{\gamma 2b}$, $C_{\gamma 2c}$ or $C_{\gamma 3}$) of the two copies of said IgG constant region gene of an immunoglobulin heavy chain constant region, giving rise to a mouse that is heterozygous with respect to the heterologous immunoglobulin heavy chain constant region sequence. In some embodiments, a mouse is provided that is homozygous for an immunoglobulin heavy chain constant region that includes a heterologous immunoglobulin heavy chain constant region sequence as described herein.

In some embodiments, an engineered immunoglobulin heavy chain constant region as described herein comprises one or more IgG encoding $C_H$ gene segments that each comprise a human extracellular domain encoding sequence (e.g., a human IgG $C_H1$-H-$C_H2$-$C_H3$) operably linked to a non-human transmembrane and cytoplasmic domain encoding sequence (e.g., a non-human IgG M1-M2) of the same or different IgG subclasses.

In some embodiments, an engineered immunoglobulin heavy chain constant region as described herein comprises one or more engineered IgG encoding $C_H$ gene segments as described herein and further comprises a wild-type (e.g., unmodified non-human such as rat or mouse) $C_\mu$ constant region gene.

In some embodiments, an engineered immunoglobulin heavy chain constant region as described herein comprises one or more engineered IgG encoding $C_H$ gene segments as described herein and further comprises wild-type (e.g., unmodified non-human such as rat or mouse) $C_\mu$ and $C_\delta$ constant region genes.

In various embodiments, an engineered IgG encoding $C_H$ gene segment comprising a human immunoglobulin heavy chain constant region sequence as described herein is an engineered IgG encoding $C_H$ gene segment of IgG subclass selected from $C_{\gamma 1}$, $C_{\gamma 2a}$, $C_{\gamma 2b}$, $C_{\gamma 2c}$, or $C_{\gamma 3}$.

In some certain embodiments, an engineered immunoglobulin heavy chain constant region as described herein comprises an engineered $C_{\gamma 2a}$ gene segment comprising a sequence encoding human IgG1 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 2a}$ gene segment.

In some certain embodiments, an engineered immunoglobulin heavy chain constant region as described herein comprises an engineered $C_{\gamma 2a}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 2a}$ gene segment.

In some certain embodiments, an engineered immunoglobulin heavy chain constant region as described herein comprises an engineered $C_{\gamma 2c}$ gene segment comprising a sequence encoding human IgG1 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 2c}$ gene segment.

In some certain embodiments, an engineered immunoglobulin heavy chain constant region as described herein comprises an engineered $C_{\gamma 2c}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 2c}$ gene segment.

In some certain embodiments, an engineered immunoglobulin heavy chain constant region as described herein comprises an engineered $C_{\gamma 1}$ gene segment comprising a sequence encoding human IgG4 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 1}$ gene segment.

In some certain embodiments, an engineered immunoglobulin heavy chain constant region as described herein comprises an engineered $C_{\gamma 1}$ gene segment comprising a sequence encoding human IgG4 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 1}$ gene segment.

In some certain embodiments, an engineered immunoglobulin heavy chain constant region as described herein comprises an engineered $C_{\gamma 2a}$ gene segment comprising a sequence encoding human IgG1 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 2a}$ gene segment, and an engineered $C_{\gamma 1}$ gene segment comprising a sequence encoding human IgG4 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 1}$ gene segment.

In some certain embodiments, an engineered immunoglobulin heavy chain constant region as described herein comprises an engineered $C_{\gamma 2a}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 2a}$ gene segment, and an engineered $C_{\gamma 1}$ gene segment comprising a sequence encoding human IgG4 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 1}$ gene segment.

In some certain embodiments, an engineered immunoglobulin heavy chain constant region as described herein comprises an engineered $C_{\gamma 2c}$ gene segment comprising a sequence encoding human IgG1 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 2c}$ gene segment, and an engineered $C_{\gamma 1}$ gene segment comprising a sequence encoding human IgG4 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 1}$ gene segment.

In some certain embodiments, an engineered immunoglobulin heavy chain constant region as described herein comprises an engineered $C_{\gamma 2c}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 2c}$ gene segment, and an engineered $C_{\gamma 1}$ gene segment comprising a sequence encoding human IgG4 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 1}$ gene segment.

In various embodiments, an engineered immunoglobulin heavy chain constant region as described herein comprises one or more further modifications including rendering constant region genes (i.e., isotypes) other than one or more IgG constant regions that comprise a sequence encoding human IgG $C_H1$-H-$C_H2$-$C_H3$ or human IgG $C_H1$-H-$C_H2$-$C_H3$-M1-M2 (e.g., IgG1 and/or IgG2a) to be nonfunctional, e.g., via deletion in whole or in part, alteration in whole or in part, disruption in whole or in part, replacement in whole or in part of one or more immunoglobulin constant region genes encoding IgD, IgE, IgA and an IgG that does not itself contain a sequence encoding human IgG $C_H1$-H-$C_H2$-$C_H3$ or human IgG $C_H1$-H-$C_H2$-$C_H3$-M1-M2 as described herein (e.g., IgG2b and/or IgG3). Engineered non-human embryos, cells and targeting vectors for making such mice, embryos and cells are also provided.

In some certain embodiments, an engineered immunoglobulin heavy chain constant region provided herein comprises a wild-type (e.g., unmodified non-human such as rat or mouse) $C_\mu$ gene segment, a $C_{\gamma 1}$ gene segment comprising a sequence encoding human IgG4 $C_H1$-H-$C_H2$-$C_H3$ in the place of $C_H1$-H-$C_H2$-$C_H3$ exons and operably linked to M1-M2 exons of said $C_{\gamma 1}$ gene segment, and a deletion of the $C_\delta$, $C_{\gamma 2a}$, $C_{\gamma 2c}$, $C_{\gamma 2b}$, $C_{\gamma 3}$, $C_\varepsilon$ and $C_\alpha$ gene segments.

In some certain embodiments, an engineered immunoglobulin heavy chain constant region provided herein comprises a wild-type (e.g., unmodified non-human such as rat or mouse) $C_\mu$ gene segment, a $C_{\gamma 1}$ gene segment comprising a sequence encoding human IgG4 $C_H1$-H-$C_H2$-$C_H3$-M1-M2 in the place of $C_H1$-H-$C_H2$-$C_H3$-M1-M2 exons and operably linked to the switch region of said $C_{\gamma 1}$ gene segment, and a deletion of the $C_\delta$, $C_{\gamma 2a}$, $C_{\delta 2c}$, $C_{\delta 2b}$, $C_{\gamma 3}$, $C_\varepsilon$ and $C_\alpha$ gene segments.

In some certain embodiments, an engineered immunoglobulin heavy chain constant region provided herein comprises a wild-type (e.g., unmodified non-human such as rat or mouse) $C_\mu$ gene segment, a $C_{\gamma 2a}$ gene segment comprising a sequence encoding human IgG1 $C_H1$-H-$C_H2$-$C_H3$ in the place of $C_H1$-H-$C_H2$-$C_H3$ exons and operably linked to M1-M2 exons of said $C_{\gamma 2a}$ gene segment, and a deletion of the $C_\delta$, $C_{\gamma 1}$, $C_{\gamma 2b}$, $C_{\gamma 2c}$, $C_{\gamma 3}$, $C_\varepsilon$ and Cα gene segments.

In some certain embodiments, an engineered immunoglobulin heavy chain constant region provided herein comprises a wild-type (e.g., unmodified non-human such as rat or mouse) $C_\mu$ gene segment, a $C_{\gamma 2a}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of said a $C_{\gamma 2a}$ gene segment, and a deletion of the $C_\delta$, $C_{\gamma 1}$, $C_{\gamma 2b}$, $C_{\gamma 2c}$, $C_{\gamma 3}$, $C_\varepsilon$ and $C_\alpha$ gene segments.

In some certain embodiments, an engineered immunoglobulin heavy chain constant region provided herein comprises a wild-type (e.g., unmodified non-human such as rat or mouse) $C_\mu$ gene segment, a $C_{\gamma 2c}$ gene segment comprising a sequence encoding human IgG1 $C_H1$-H-$C_H2$-$C_H3$ in the place of $C_H1$-H-$C_H2$-$C_H3$ exons and operably linked to M1-M2 exons of said $C_{\gamma 2c}$ gene segment, and a deletion of the $C_\delta$, $C_{\gamma 1}$, $C_{\gamma 2a}$, $C_{\gamma 2b}$, $C_{\gamma 3}$, $C_\varepsilon$ and Cα gene segments.

In some certain embodiments, an engineered immunoglobulin heavy chain constant region provided herein comprises a wild-type (e.g., unmodified non-human such as rat or mouse) $C_\mu$ gene segment, a $C_{\gamma 2c}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of said a $C_{\gamma 2c}$ gene segment, and a deletion of the $C_\delta$, $C_{\gamma 1}$, $C_{\gamma 2a}$, $C_{\gamma 2b}$, $C_{\gamma 3}$, $C_\varepsilon$ and G gene segments.

In various embodiments, an engineered immunoglobulin heavy chain constant region as described herein comprises one or more further modifications including engineering constant region genes (i.e., isotypes) other than one or more IgG constant regions that comprise a sequence encoding human IgG $C_H1$-H-$C_H2$-$C_H3$ or human IgG $C_H1$-H-$C_H2$-$C_H3$-M1-M2 (e.g., IgG1 and/or IgG2a) to be altered, modified, replaced, engineered, etc. via insertion of a human immunoglobulin heavy chain constant region sequence as described herein into one or more immunoglobulin constant region genes for IgD, IgE, IgA and an IgG that does not itself contain a sequence encoding human IgG $C_H1$-H-$C_H2$-$C_H3$ or human IgG $C_H1$-H-$C_H2$-$C_H3$-M1-M2 as described herein (e.g., IgG2b and/or IgG3).

Engineered mouse embryos, cells and targeting vectors for making mice, embryos and cells comprising immunoglobulin loci with engineered constant regions described herein are also provided.

In some certain embodiments, an engineered immunoglobulin heavy chain constant region provided herein comprises a wild-type $C_\mu$ gene segment, a wild-type $C_\delta$ gene segment, a $C_{\gamma 3}$ gene segment comprising a sequence encoding human IgG3 $C_H1$-H-$C_H2$-$C_H3$ in the place of $C_H1$-H-$C_H2$-$C_H3$ exons and operably linked to M1-M2 exons of said $C_{\gamma 3}$ gene segment, a $C_{\gamma 1}$ gene segment comprising a sequence encoding human IgG4 $C_H1$-H-$C_H2$-$C_H3$ in the place of $C_H1$-H-$C_H2$-$C_H3$ exons and operably linked to M1-M2 exons of said $C_{\gamma 1}$ gene segment, a $C_{\gamma 2b}$ gene segment comprising a sequence encoding human IgG2 $C_H1$-H-$C_H2$-$C_H3$ in the place of $C_H1$-H-$C_H2$-$C_H3$ exons and operably linked to M1-M2 exons of said $C_{\gamma 2b}$ gene segment, a $C_{\gamma 2a}$ gene segment comprising a sequence encoding human IgG1 $C_H1$-H-$C_H2$-$C_H3$ in the place of $C_H1$-H-$C_H2$-$C_H3$ exons and operably linked to M1-M2 exons of said $C_{\gamma 2a}$ gene segment (and/or a $C_{\gamma 2c}$ gene segment comprising a sequence encoding human IgG1 $C_H1$-H-$C_H2$-$C_H3$ in the place of $C_H1$-H-$C_H2$-$C_H3$ exons and operably linked to M1-M2 exons of said $C_{\gamma 2c}$ gene segment), a $C_\varepsilon$ gene segment comprising a sequence encoding human IgE $C_H1$-$C_H2$-$C_H3$-$C_H4$ in the place of $C_H1$-$C_H2$-$C_H3$-$C_H4$ exons and operably linked to M1-M2 exons of said an $C_\varepsilon$ gene segment, and a $C_\alpha$ gene segment comprising a sequence encoding human IgA1 or IgA2 $C_H1$-H-$C_H2$-$C_H3$ in the place of $C_H1$-H-$C_H2$-$C_H3$ exons and operably linked to M exon(s) of said $C_\alpha$ gene segment.

In some certain embodiments, an engineered immunoglobulin heavy chain constant region provided herein comprises a wild-type $C_\mu$ gene segment, a wild-type $C_\delta$ gene segment, a $C_{\gamma 3}$ gene segment comprising a sequence encoding human IgG3 $C_H1$-H-$C_H2$-$C_H3$-M1-M2 in the place of $C_H1$-H-$C_H2$-$C_H3$-M1-M2 exons and operably linked to the switch region of said $C_{\gamma 3}$ gene segment, a $C_{\gamma 1}$ gene segment comprising a sequence encoding human IgG4 $C_H1$-H-$C_H2$-$C_H3$-M1-M2 in the place of $C_H1$-H-$C_H2$-$C_H3$-M1-M2 exons and operably linked to the switch region of said a $C_{\gamma 1}$ gene segment, a $C_{\gamma 2b}$ gene segment comprising a sequence encoding human IgG2 $C_H1$-H-$C_H2$-$C_H3$-M1-M2 in the place of $C_H1$-H-$C_H2$-$C_H3$-M1-M2 exons and operably linked to the switch region of said $C_{\gamma 2b}$ gene segment, a $C_{\gamma 2a}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of said $C_{\gamma 2a}$ gene segment (and/or a $C_{\gamma 2c}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of said $C_{\gamma 2c}$ gene segment), a $C_\varepsilon$ gene segment comprising a sequence encoding human IgE $C_H1$-$C_H2$-$C_H3$-$C_H4$ in the place of $C_H1$-$C_H2$-$C_H3$-$C_H4$ exons and operably linked to M1-M2 exons of said an $C_\varepsilon$ gene segment, and a $C_\alpha$ gene segment comprising a sequence encoding human IgA1 or IgA2 $C_H1$-H-$C_H2$-$C_H3$ in the place of $C_H1$-H-$C_H2$-$C_H3$ exons and operably linked to M exon(s) of said $C_\alpha$ gene segment.

In some embodiments, the mouse is heterozygous for the modified immunoglobulin heavy chain locus described herein. In certain embodiments, the mouse is homozygous for the modified immunoglobulin heavy chain locus described herein.

Therapeutic agents comprising a human Fc (e.g., agents comprising a human Fcα, such as therapeutic human IgA antibodies) are typically tested in non-human species (e.g., mice) before they are administered to humans. Unfortunately, agents comprising a human Fc region often exhibit very different pharmacokinetic and pharmacodynamic properties when administered to prior art mice compared to when administered to humans. For example, when therapeutic agents with human Fc regions are administered to conventional mice, the human sequences in the Fc regions are often identified as foreign by the mouse immune system. As a consequence, the mouse may mount an immune response against the administered therapeutic agents (known as mouse anti-human response or MAHA), which affects the pharmacokinetic and pharmacodynamic properties of the administered agents. Thus, conventional mouse models are often poor predictors of human therapeutic responses to therapeutic agents comprising a human Fc. In certain embodiments, the mice provided herein have a reduced MAHA response following administration of a therapeutic agent comprising a human Fc. Thus, mice disclosed herein having human immunoglobulin locus regions are helpful in reducing or eliminating MAHA responses.

Thus, the various mice provided herein expressing human or humanized FcαR and comprising human constant regions (e.g., human $C_\alpha$ constant regions) can be used to test MAHA responses to administration of agents comprising a human Fc (e.g., agents comprising a human Fcα, such as therapeutic human IgA antibodies), for example, as disclosed in WO2019/190990, which is hereby incorporated by reference in its entirety.

Humanized Immunoglobulin Kappa Loci

In some embodiments, the mice provided herein further comprise a humanized Igκ chain locus. As disclosed in WO2019/190990, which is hereby incorporated by reference in its entirety, testing therapeutic agents comprising a human κ chain in mice having humanized Igκ chain locus can reduce or eliminate MAHA responses because the human κ chain is less likely to be identified by foreign in such mice.

In some embodiments, the mice and ES cells genetically modified to comprise in their genome a humanized or human FcαR1 locus further comprise a genetically modified Igκ chain loci. Such loci comprise a κ variable region and a κ constant region. The κ variable region includes Igκ chain variable region gene segments (i.e., at least a $V_K$ gene segment and a $J_K$ gene segment). The constant region includes an Igκ chain constant region ($C_K$) gene segment. In certain embodiments, the immunoglobulin κ chain variable region such as human Igκ variable region is operably linked to the immunoglobulin κ chain constant region such that the mouse produces antibodies comprising light chain variable domains derived from the human $V_K$ gene segment and the human $J_K$ gene segment and light chain constant domains derived from the $C_K$ gene segment. In some embodiments, the Igκ variable region will be an unrearranged Igκ variable region and will therefore contain unrearranged Igκ variable region gene segments. In some embodiments, the Igκ variable region will be a rearranged Igκ variable region and will therefore contain a rearranged Igκ variable region gene. In certain embodiments, the Igκ variable region gene segments are human Igκ variable region gene segments. In certain embodiments, the Igκ variable region gene segments are rodent Igκ variable region gene segments (e.g., rat or mouse variable region gene segments). In some embodiments, the Igκ constant region locus comprises an Igκ constant region gene segment that is partially or completely human. In some embodiments, the Igκ chain loci described herein are located at an endogenous Igκ chain locus.

In certain embodiments, the Igκ variable region contains unrearranged human Igκ variable region gene segments. In some certain embodiments, an engineered Igκ light chain locus (or allele) comprises at least human $V_K$ gene segments that appear in the distal variable cluster (or distal arm, or distal duplication) of a human Igκ light chain locus that appears in nature. In some certain embodiments, an engineered Igκ light chain locus (or allele) comprises at least human $V_K$ gene segments that appear in the proximal variable cluster (or proximal arm, or proximal duplication) of a human Igκ light chain locus that appears in nature. In some certain embodiments, an engineered Igκ light chain locus (or allele) comprises human $V_K$ gene segments that appear in the distal and proximal variable clusters of a human Igκ light chain locus that appears in nature. In some certain embodiments, an engineered Igκ light chain locus (or allele) comprises all or substantially all the functional human $V_K$ gene segments found between human $V_K$ 2-40 (or $V_K$ 3D-7) and human $V_K$ 4-1 gene segments, inclusive, of a human Igκ light chain locus that appears in nature.

In some embodiments, the unrearranged human immunoglobulin variable region gene segments comprise a plurality of human $V_K$ segments and one or more human $J_K$ segments. In some embodiments, the immunoglobulin variable region gene segments comprise four functional $V_K$ segments and all human $J_K$ segments. In some embodiments, the immunoglobulin variable region gene segments comprise 16 functional $V_K$ segments and all human $J_K$ segments. In some embodiments, the unrearranged human immunoglobulin variable region gene segments comprise all of the human $V_K$ segments and all human $J_K$ segments.

In some certain embodiments, an engineered Igκ light chain locus (or allele) comprises 1, 2, 3, 4, 5, 6, 7, 8, 9, 10, 15, 20, 25, 30, 35 or more (e.g., 36, 37, 38, 39, 40 etc.) human $V_K$ gene segments. In some certain embodiments, an engineered Igκ light chain locus (or allele) comprises human $V_K$ gene segments $V_K$ 3D-7, $V_K$ 1D-8, $V_K$ 1D-43, $V_K$ 3D-11, $V_K$ 1D-12, $V_K$ 1D-13, $V_K$ 3D-15, $V_K$ 1D-16, $V_K$ 1D-17, $V_K$ 3D-20, $V_K$ 6D-21, $V_K$ 2D-26, $V_K$ 2D-28, $V_K$ 2D-29, $V_K$ 2D-30, $V_K$ 1D-33, $V_K$ 1D-39, $V_K$ 2D-40, $V_K$ 2-40, $V_K$ 1-39, $V_K$ 1-33, $V_K$ 2-30, $V_K$ 2-28, $V_K$ 1-27, $V_K$ 2-24, $V_K$ 6-21, $V_K$ 3-20, $V_K$ 1-17, $V_K$ 1-16, $V_K$ 3-15, $V_K$ 1-12, $V_K$ 3-11, $V_K$ 1-9, $V_K$ 1-8, $V_K$ 1-6, $V_K$ 1-5, $V_K$ 5-2 and $V_K$ 4-1. In some certain embodiments, an engineered Igκ light chain locus (or allele) comprises at least human V gene segments $V_K$ 3D-7, $V_K$ 1D-8, $V_K$ 1D-43, $V_K$ 3D-11, $V_K$ 1D-12, $V_K$ 1D-13, $V_K$ 3D-15, $V_K$ 1D-16, $V_K$ 1D-17, V 3D-20, $V_K$ 6D-21, $V_K$ 2D-26, $V_K$ 2D-28, $V_K$ 2D-29, $V_K$ 2D-30, $V_K$ 1D-33, $V_K$ 1D- 39 and V 2D-40. In some certain embodiments, an engineered Igκ light chain locus (or allele) comprises at least human $V_K$ gene segments $V_K$ 2-40, $V_K$ 1-39, $V_K$ 1-33, $V_K$ 2-30, $V_K$ 2-28, $V_K$ 1-27, $V_K$ 2-24, $V_K$ 6-21, $V_K$ 3-20, $V_K$ 1-17, $V_K$ 1-16, $V_K$ 3-15, $V_K$ 1-12, $V_K$ 3-11, $V_K$ 1-9, $V_K$ 1-8, $V_K$ 1-6, $V_K$ 1-5, $V_K$ 5-2 and $V_K$ 4-1.

In some embodiments, the mice provided herein have a restricted immunoglobulin light chain locus characterized by no more than two human $V_L$ gene segments and a plurality of $J_L$ gene segments (e.g., dual light chain mice, or DLC, as described in U.S. Pat. Pub. No. 2013/0198880, which is hereby incorporated by reference). In some embodiments, the $V_L$ gene segments are $V_K$ gene segments. In some embodiments, the $V_L$ gene segments are $V_\lambda$ gene segments. In some embodiments, the $V_K$ gene segments are $V_K$3-20 and $V_K$ 1-39.

In some embodiments, an engineered Igκ light chain locus (or allele) comprises 1, 2, 3, 4, 5 or more functional human $J_\kappa$ gene segments. In some certain embodiments, an engineered Igκ light chain locus (or allele) comprises all or substantially all the functional human $J_\kappa$ gene segments found between human $J_\kappa 1$ and human $J_\kappa 5$ gene segments, inclusive, of a human Igκ light chain locus that appears in nature. In some certain embodiments, an engineered Igκ light chain locus (or allele) comprises at least human $J_\kappa$ gene segments $J_\kappa 1$, $J_\kappa 2$, $J_\kappa 3$, $J_\kappa 4$ and $J_\kappa 5$.

In yet other embodiments, the non-human organism may comprise in its germline and/or genome a light chain immunoglobulin locus that includes insertions and/or replacements of histidine codons designed to introduce pH-dependent binding properties to the antibodies generated in such non-human organism. In some of such embodiments, the histidine codons are inserted and/or replaced in the nucleic acid sequences encoding CDR3. Various such light chain immunoglobulin loci are provided in U.S. Pat. Nos. 9,301, 510, 9,334,334, U.S. Patent Application Publication Nos. 2013/0247236, 2014/0013456, incorporated herein by reference.

Exemplary variable regions comprising Igκ gene segments are provided, for example, in Macdonald et al., *Proc. Natl. Acad. Sci. USA* 111:5147-52 and supplemental information, which is hereby incorporated by reference. In some embodiments, the unrearranged human immunoglobulin variable region gene segments comprise all of the human $J_\kappa$ segments.

In some embodiments, the Igκ variable gene locus containing unrearranged human Igκ variable region gene segments also includes human Igκ variable region intergenic sequences. In some embodiments, the Igκ variable gene locus includes non-human (e.g., rodent, rat, mouse) Igκ variable region intergenic sequences. In some embodiments, the Igκ gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, the Igκ variable region locus is a rearranged variable region locus comprising an Igκ variable region gene (a universal light chain variable region). In some embodiments, the rearranged Igκ variable region gene is a human rearranged Igκ variable region gene (e.g., human rearranged Igκ variable region comprising human Vκ1-39$J_\kappa$ or human $V_\kappa$3-20$J_\kappa$ sequence, such as human $V_\kappa$1-39$J_\kappa$5 or human $V_\lambda$3-20$J_\kappa$1 sequence). Use of universal light chain variable regions facilitate the generation of bispecific antibodies. Exemplary rearranged Ig light chain variable regions are provided in U.S. Patent Pub. No. 2013/0185821, which is hereby incorporated by reference.

In some embodiments, the Igκ chain locus comprises human or rodent (e.g., rat or mouse) regulatory elements. In some embodiments, the regulatory element is an endogenous regulatory element. In certain embodiments, the Igκ chain locus comprises a rodent (e.g., rat or mouse) or human intronic K enhancer ($E_{\kappa i}$). In some embodiments, the IgH locus comprises a rodent (e.g., rat or mouse) or human 3' K enhancer ($E_{\kappa 3'}$).

In some embodiments, the modified immunoglobulin κ chain locus in the genetically modified rodent comprises one or more unrearranged human Vλ gene segments and one or more unrearranged human Jλ gene segments upstream of (e.g., operably linked to) a C gene. Rodents including such genetically modified immunoglobulin κ chain locus are exemplified in, e.g., U.S. Pat. No. 11,051,498, which is incorporated by reference in its entirety. In some embodiments, the modified immunoglobulin κ chain locus in the genetically modified rodent comprises a limited human λ light chain variable region repertoire, wherein the limited human λ light chain variable region repertoire comprises a single rearranged human immunoglobulin λ light chain variable region (Vλ/Jλ). A single rearranged human λ light chain variable region comprises a human Vλ gene segment joined to a human JD gene segment, operably linked to a Cκ or Cλ gene segment (e.g., rodent Cκ or Cλ gene segment (e.g., a mouse Cλ1 gene segment)). Rodents including such genetically modified immunoglobulin κ chain locus are exemplified in WO2020/247623, which is incorporated by reference in its entirety.

In some embodiments, the modified immunoglobulin κ chain locus is positioned at an endogenous immunoglobulin κ chain locus. In some embodiments, the immunoglobulin κ chain locus replaces all or part of the endogenous immunoglobulin κ chain locus. In certain embodiments, the modified Igκ chain locus is located on a transgene positioned outside of the endogenous locus. In some embodiments, the endogenous Igκ chain locus is inactivated (e.g., through the deletion, relocation and/or inversion of all or part of the endogenous Igκ chain locus).

In some embodiments, the mouse is heterozygous for the modified immunoglobulin κ chain locus described herein. In certain embodiments, the mouse is homozygous for modified the immunoglobulin κ chain locus described herein.

Thus, the various mice provided herein expressing human or humanized FcαR and comprising human light chain constant regions (and in some embodiments also a human $C_\alpha$ constant regions) can be used to test MAHA responses to administration of agents comprising a human Fc (e.g., agents comprising a human Fcα, such as therapeutic human IgA antibodies), for example, as disclosed in WO2019/190990, which is hereby incorporated by reference in its entirety.

Humanized Immunoglobulin Lambda Loci

In some embodiments, the mice provided herein further comprise a humanized Igλ chain locus. As disclosed in WO2019/190990, which is hereby incorporated by reference in its entirety, testing therapeutic agents comprising a human κ chain in mice having humanized Igλ chain locus can reduce or eliminate MAHA responses because the human λ chain is less likely to be identified by foreign in such mice.

In some embodiments, the mice and ES cells genetically modified to comprise in their genome a humanized or human FcαR1 locus further comprise genetically modified Igλ chain loci. Such loci comprise Igλ chain variable region gene segments (i.e., at least a $V_\lambda$ gene segment and a $J_\lambda$ gene segment). The modified λ locus further includes at least one Igλ chain constant region ($C_\lambda$) gene segment. In certain embodiments, the $V_\lambda$ gene segment and $J_\lambda$ gene segment such as human $V_\lambda$ gene segment and human $J_\lambda$ gene segment are operably linked to the $C_\lambda$ such that the mouse produces antibodies comprising light chain variable domains derived from the human $V_\lambda$ gene segment and the human $J_\lambda$ gene segment and light chain constant domains derived from the $C_\lambda$ gene segment. In some embodiments, the $V_\lambda$ gene segment and $J_\lambda$ gene segment will be unrearranged $V_\lambda$ and $J_\lambda$ gene segments. In some embodiments, the $V_\lambda$ gene segment and $J_\lambda$ gene segment will be a rearranged $V_\lambda$ and $J_\lambda$ gene segments and will therefore be in the form of a rearranged variable region gene. In certain embodiments, the $Ig_\lambda$ variable region gene segments are human variable region gene segments. In certain embodiments, the $Ig_\lambda$ variable region gene segments are rodent variable region gene segments (e.g., rat or mouse variable region gene segments). In some embodiments, the $Ig_\lambda$ constant region locus comprises a $\lambda$ constant region gene segment that is partially or completely human. In some embodiments, the $Ig\lambda$ chain loci described herein are located at an endogenous $Ig\lambda$ chain locus. Exemplary variable regions comprising $Ig\lambda$ gene segments are provided, for example, U.S. Pat. Pub. Nos. 2012/0073004 and 2002/0088016, and U.S. patent application Ser. No. 15/803,513 (filed Nov. 3, 2017; published as US2018/0125043), each of which is hereby incorporated by reference.

In some embodiments, the $Ig\lambda$ variable gene locus containing unrearranged human $Ig\lambda$ variable region gene segments also includes human $Ig\lambda$ variable region intergenic sequences. In some embodiments, the $Ig\lambda$ variable gene locus includes non-human (e.g., rodent, rat, mouse) $Ig\lambda$ variable region intergenic sequences. In some embodiments, the $Ig\lambda$ gene locus comprises non-human regulatory elements (e.g., non-human promoters and/or enhancers). In some embodiments, the non-human regulatory elements are rodent regulatory elements (e.g., rat or mouse promoters or enhancers).

A human $Ig\lambda$ light chain locus, in some embodiments, comprises genetic material from a human $Ig\lambda$ light chain locus. In some embodiments, a human $Ig\lambda$ light chain locus as described herein comprises at least one human $V_\lambda$ gene segment at least one human $J_\lambda$ gene segment, at least one human $C_\lambda$ gene segment, and one or more sequences necessary to promote rearrangement (e.g., recombination signal sequence[s]) of said at least one human $V_\lambda$ gene segment with said at least one human $J_\lambda$ gene segment to form a functional rearranged human $V_\lambda$-$J_\lambda$ sequence that encodes a human $V_\lambda$ domain. In many embodiments, a human $Ig\lambda$ light chain sequence comprises a plurality of human $V_\lambda$ gene segments and one or more sequences necessary to promote rearrangement of said human $V_\lambda$ gene segments with at least one human $J_\lambda$ gene segment. In some embodiments, a human $Ig\lambda$ light chain sequence as described herein is a genomic sequence of a human $Ig\lambda$ light chain locus (e.g., isolated and/or cloned from a bacterial artificial chromosome) and contains a plurality of human $V_\lambda$ gene segments in germline configuration. In some embodiments, a human $Ig\lambda$ light chain sequence comprises human $V_\lambda$, $J_\lambda$ and $C_\lambda$ sequences in germline configuration (i.e., as said human $V_\lambda$, $J_\lambda$ and $C_\lambda$ sequences appear in an $Ig\lambda$ light chain locus in a human cell; in other words, $J_\lambda$ and $C_\lambda$ sequences appear as $J_\lambda$ $C_\lambda$ clusters). In some embodiments, a human $Ig\lambda$ light chain sequence encodes an $Ig\lambda$ light chain polypeptide, in whole or in part, which $Ig\lambda$ light chain polypeptide appears in an immunoglobulin, in particular, an immunoglobulin that is expressed by a human B cell. Mice, embryos, cells and targeting constructs for making mice, non-human embryos, and cells containing said human $Ig\lambda$ light chain sequence in the place of a corresponding non-human $Ig\lambda$ light chain sequence (e.g., an endogenous mouse $Ig\lambda$ light chain locus) are also provided.

In some embodiments, a human $Ig\lambda$ light chain sequence is inserted in the place of a corresponding non-human $Ig\lambda$ light chain sequence within the germline genome of a non-human animal. In some embodiments, a human $Ig\lambda$ light chain sequence is inserted upstream of a non-human $Ig\lambda$ light chain sequence (e.g., a non-human $Ig\lambda$ light chain constant region sequence). In some embodiments, a human $Ig\lambda$ light chain sequence is inserted in the midst of one or more non-human $Ig\lambda$ light chain sequences so that said human $Ig\lambda$ light chain sequence is juxtaposed by non-human $Ig\lambda$ light chain sequences.

In certain embodiments, the $Ig\lambda$ chain locus comprises at least 2, 3, 4, 5, 6, 7, 8, 10, 20, 30 or 40 functional $V_\lambda$ gene segments. In some embodiments, the locus comprises human $V_\lambda$ gene segments $V_\lambda 3$-10, $V_\lambda 3$-9, $V_\lambda 2$-8, $V_\lambda 4$-3 and $V_\lambda 3$-1. In some embodiments, the locus comprises $V_\lambda 2$-11, $V_\lambda 3$-12, $V_\lambda 2$-14, $V_\lambda 3$-16, $V_\lambda 3$-19, $V_\lambda 3$-21, $V_\lambda 3$-22, $V_\lambda 2$-23, $V_\lambda 3$-25 and $V_\lambda 3$-27. In some embodiments, the locus comprises $V_\lambda 3$-27, $V_\lambda 1$-36, $V_\lambda 5$-37, $V_\lambda 5$-39, $V_\lambda 1$-40, $V_\lambda 7$-43, $V_\lambda 1$-44, $V_\lambda 5$-45, $V_\lambda 7$-46, $V_\lambda 1$-47, $V_\lambda 9$-49, $V_\lambda 1$-51 and $V_\lambda 5$-52. In certain embodiments, the locus comprises $V_\lambda 10$-54, $V_\lambda 6$-57, $V_\lambda 4$-60, $V_\lambda 8$-61 and $V_\lambda 4$-69. In some embodiments, the $Ig\lambda$ chain locus comprises one or more human $J_\lambda$-$C_\lambda$ pairs. For example, in certain embodiments, the $Ig\lambda$ chain locus comprises human $J_\lambda 1$-$C_\lambda 1$, $J_\lambda 2$-$C_\lambda 2$, $J_\lambda 3$-$C_\lambda 3$, $J_\lambda 6$-$C_\lambda 6$ and/or $J_\lambda 7$-$C_\lambda 7$ downstream of the human $V_\lambda$ gene segments. In some embodiments, the $Ig_\lambda$ chain locus comprises human $J_\lambda 1$-$C_\lambda 1$, $J_\lambda 2$-$C_\lambda 2$, $J_\lambda 3$-$C_\lambda 3$, $J_\lambda 6$-$C_\lambda 6$, human $J_\lambda 7$ and mouse $C_\lambda 1$ downstream of the human $V_\lambda$ gene segments.

In some embodiments, the $Ig\lambda$ locus is a rearranged locus comprising a $Ig\lambda$ variable region gene (a universal light chain variable region). In some embodiments, the rearranged $Ig\lambda$ variable region gene is a human rearranged $Ig\lambda$ variable region gene. Use of universal light chain variable regions facilitate the generation of bispecific antibodies in which at least one antigen-binding domain has binding. Exemplary rearranged Ig light chain variable regions are provided in U.S. Patent Pub. No. 2013/0185821, which is hereby incorporated by reference.

In some embodiments, the $Ig\lambda$ chain locus comprises human or rodent (e.g., rat or mouse) regulatory elements. In some embodiments, the regulatory element is an endogenous regulatory element. In certain embodiments, the $Ig\lambda$ chain locus comprises a rodent (e.g., rat or mouse) $\lambda$ enhancer 2.4. In some embodiments, the $Ig\lambda$ chain locus comprises a human or rodent (e.g., rat or mouse) 3'$\lambda$ enhancer. In some embodiments, the $Ig\lambda$ chain locus comprises a rodent (e.g., rat or mouse) $\lambda$ enhancer 3.1.

In some embodiments, the modified immunoglobulin $\lambda$ chain locus is positioned at an endogenous immunoglobulin $\lambda$ chain locus. In some embodiments, the immunoglobulin $\lambda$ chain locus replaces all or part of the endogenous immunoglobulin $\lambda$ chain locus. In certain embodiments, the modified $Ig\lambda$ chain locus is located on a transgene positioned outside of the endogenous locus. In certain embodiments, the modified $Ig\lambda$ chain locus is located at an endogenous immunoglobulin $\kappa$ chain locus. In some embodiments, the endogenous $Ig\lambda$ chain locus is inactivated (e.g., through the deletion, relocation and/or inversion of all or part of the endogenous $Ig\lambda$ chain locus).

In some embodiments, the mouse is heterozygous for the modified immunoglobulin $\lambda$ chain locus. In certain embodiments, the mouse is homozygous for modified the immunoglobulin $\lambda$ chain locus.

In some embodiments, the mouse comprises in its germline and/or genome a light chain immunoglobulin locus comprising a limited repertoire of light chain variable gene segments (e.g., a dual light chain variable region comprising two light chain variable gene segments). In some embodiments, the light chain variable gene segments in the limited repertoire of light chain gene segments are a human light chain gene segments. Exemplary dual light chain variable regions are provided in U.S. Patent Pub. No. 2013/0198880, which is hereby incorporated by reference. In some embodiments, the mouse comprising a dual light chain variable region is used to produce bispecific antibodies.

Thus, the various mice provided herein expressing human or humanized FcαR and comprising human light chain constant regions (and in some embodiments also a human $C_\alpha$ constant regions) can be used to test MAHA responses to administration of agents comprising a human Fc (e.g., agents comprising a human Fcα, such as therapeutic human IgA antibodies), for example, as disclosed in WO2019/190990, which is hereby incorporated by reference in its entirety.

Humanized CD79a and CD79b Loci

In some embodiments, the mice and ES cells genetically modified to comprise in their genome a humanized or human FcαR1 locus further comprise a human or humanized B-cell antigen receptor complex-associated protein alpha chain (CD79a or Igα) and/or B-cell antigen receptor complex-associated protein beta chain (CD79b or Igβ) loci. Mice that contain human or humanized CD79a and CD79b genes express human or humanized CD79a and CD79b polypeptides as heterodimers on the surface of B cells, which associate with membrane-expressed immunoglobulins in a noncovalent manner to form the B cell receptor (BCR). The BCR associates with antigen and functions in signal transduction and internalization after engagement with antigen. In some embodiments, mice described herein comprise human or humanized CD79a and CD79b genes. In some certain embodiments, mice as described herein further comprise a CD79a gene that comprises a rodent CD79a portion and a human CD79a portion, and a CD79b gene that comprises a rodent CD79b portion and a human CD79b portion, wherein the human CD79a portion encodes substantially all of the extracellular domain of a human CD79a polypeptide (e.g., amino acids corresponding to residues 33-143 of a human CD79a polypeptide) and the human CD79b portion encodes substantially all of the extracellular domain of a human CD79b polypeptide (e.g., amino acids corresponding to residues 29-159 of a human CD79b polypeptide). In some embodiments, rodent CD79a and CD79b portions each encode at least the intracellular domain of endogenous CD79a and CD79b polypeptides, respectively; in some certain embodiments the transmembrane and intracellular domains of endogenous CD79a and CD79b polypeptides, respectively. In some embodiments, human and endogenous portions are operably linked to endogenous CD79a or CD79b promoters, respectively.

In some embodiments, mice as described herein further comprise a chimeric CD79a gene that comprises a rodent CD79a portion and a human CD79a portion, wherein the human CD79a portion encodes the sequence comprising amino acids corresponding to residues 33-116 of a human CD79a polypeptide, in one embodiment it encodes the sequence comprising amino acids 33-119 of a human CD79a polypeptide, in one embodiment it encodes the sequence comprising amino acids 33-143 of a human CD79a polypeptide, in one embodiment, it encodes the sequence comprising amino acids 33-165 of a human CD79a polypeptide. In some embodiments, the chimeric CD79a polypeptide comprises a human Ig C2-like domain; in some embodiments, the chimeric CD79a polypeptide also comprises a human stalk region; in some embodiment, the chimeric CD79a polypeptide also comprises a human transmembrane domain; and in some embodiments, the chimeric CD79a polypeptide further comprises a rodent (e.g., mouse) cytoplasmic domain. In some embodiments, the mouse comprises a chimeric CD79a gene comprising a human region portion described herein and a sequence encoding a human or rodent (e.g., mouse) CD79a signal peptide; in one embodiment, the sequence encoding the signal peptide is a mouse CD79a sequence encoding amino acids 1-28 of the mouse CD79a.

In some embodiments, mice as described herein further comprise a chimeric CD79b gene that comprises a rodent CD79b portion and a human CD79b portion, wherein the human CD79b portion encodes the sequence comprising amino acids corresponding to residues 29-135 of a human CD79b polypeptide, in one embodiment it encodes the sequence comprising amino acids 29-159 of a human CD79b polypeptide, in one embodiment it encodes the sequence comprising amino acids 29-184 of a human CD79b polypeptide. In some embodiments, the chimeric CD79b polypeptide comprises a human Ig V-like domain; in some embodiments, the chimeric CD79b polypeptide also comprises a human stalk region; in some embodiment, the chimeric CD79b polypeptide also comprises a human transmembrane domain; and in some embodiments, the chimeric CD79b polypeptide further comprises a rodent (e.g., mouse) cytoplasmic domain. In some embodiments, the mouse comprises a chimeric CD79b gene comprising a human region portion described herein and a sequence encoding a human or rodent (e.g., mouse) CD79b signal peptide; in one embodiment, the sequence encoding the signal peptide is a mouse CD79b sequence encoding amino acids 1-25 of the mouse CD79b.

GenBank accession nos. NP_001774.1, NM_001783.3, NP_067612.1 and NM_021601.3, and UniProt ID P11912 provide representative source sequences of a human CD79A gene and human CD79A polypeptide from which a desired human portion may be obtained. GenBank accession nos. NP 000617.1, NM_000626.2, NP_001035022.1, NM_001039933.1, NP_067613.1 and NM_021602.2, and UniProt ID P40259 provide representative source sequences of a human CD79B gene and human CD79B polypeptide from which a desired human portion may be obtained.

In some embodiments, the mice provided herein further comprise one or more human CD79A and CD79B genes as described in U.S. Patent Application Publication Nos. 2011-0093963 A1 and 2009-0053210 A1; International Patent Application Publication No. WO 2008/027986; and European Patent No. 2 064 325 B1, each of which is hereby incorporated by reference. In some certain embodiments, the mice provided herein comprise a humanized CD79a gene that comprises an endogenous CD79a portion and a human CD79a portion, and a humanized CD79b gene that comprises an endogenous CD79b portion and a human CD79b portion, wherein the human CD79a portion encodes substantially all of the extracellular domain of a human CD79a polypeptide (e.g., amino acids corresponding to residues 33-143 of a human CD79a polypeptide) and the human CD79b portion encodes substantially all of the extracellular domain of a human CD79b polypeptide (e.g., amino acids corresponding to residues 29-159 of a human CD79b polypeptide). In some embodiments, the mice provided herein comprise a humanized CD79a gene that comprises an endogenous CD79a portion and a human CD79a portion, and a humanized CD79b gene that comprises an endogenous CD79b portion and a human CD79b portion, wherein the human CD79a portion encodes the sequence comprising amino acids 33-116 (e.g., the sequence comprising amino acids 33-119, the sequence comprising amino acids 33-143, or the sequence comprising amino acids 33-165 of a human CD79a polypeptide), and wherein the human CD79b portion encodes the sequence comprising amino acids 29-135 (e.g., the sequence comprising amino acids 29-159, or the sequence comprising amino acids 29-184 of a human CD79a polypeptide) In some embodiments, endogenous CD79a and CD79b portions each encode at least the intracellular domain of endogenous CD79a and CD79b polypeptides, respectively; in some certain embodiments the transmembrane and intracellular domains of endogenous CD79a and CD79b polypeptides, respectively.

Humanized β-2-Microglobulin

In some embodiments, the mice and ES cells genetically modified to comprise in their genome a humanized or human FcαR1 locus further comprise a locus encoding humanized β-2-microglobulin (β2M) polypeptide. β2M is a polypeptide that lacks a transmembrane region and that associates with the FcRn and MHC class I molecules.

In some embodiments, the β2M locus comprises a nucleic acid sequence encoding a human β2M polypeptide. In some embodiments, the nucleic acid sequence encoding the human β2M polypeptide is positioned at an endogenous mouse β2M locus. In certain embodiments, the nucleic acid sequence encoding the β2M polypeptide replaces all or part of an endogenous mouse β2M gene. In some embodiments, the mouse does not express a mouse β2M, or does not express a functional mouse β2M polypeptide. In some embodiments, the β2M gene locus comprises non-human regulatory elements (e.g., non-human promoters and/or enhancers). In some embodiments, the non-human regulatory elements are rodent regulatory elements (e.g., rat or mouse promoters or enhancers).

Humanized β2M polypeptides, loci encoding humanized β2M polypeptides and mice expressing humanized β2M polypeptides are described in U.S. Pat. Pub. Nos. 2013/0111617 and 2013/0185819, each of which is incorporated by reference herein. Thus, as described in U.S. Pat. Pub. Nos. 2013/0111617 and 2013/0185819, in some embodiments, mice comprise a humanized β2M gene, wherein the gene comprises exons 2, 3, and 4 of the human β2M gene, and in some embodiments, the humanized β2M gene comprises exon 1 of the non-human (e.g., mouse) β2M gene. In some embodiments, the mouse is heterozygous for the genetically modified β2M locus. In some embodiments, the mouse is homozygous for the genetically modified β2M locus.

Genetically Modified Mice and ES Cells

In certain aspects, provided herein are genetically modified mice and ES cells comprising one or more of the humanized loci disclosed herein as well as genetically modified mouse ES cells useful in the making of such mice.

In certain aspects, provided herein are genetically modified mice and mouse ES cells comprising in their germline and/or genome a humanized or human FcαR1 locus. For example, in some embodiments, the mouse or ES cell comprises in its germline and/or genome an FcαR locus provided herein. In some embodiments, the mouse or ES cell further comprises an IgH locus provided herein. In some embodiments, the mouse or ES cell further comprises an Igκ and/or an Igλ locus provided herein. In some embodiments, the mouse or ES cell comprises in their germline and/or genome a CD79a and/or a CD79b locus provided herein. In some embodiments, the mouse or ES cell comprises in their germline and/or genome an FcRn locus provided herein. In some embodiments, the mouse or ES cell comprises in their germline and/or genome a β2M locus provided herein. In some embodiments, the mouse or ES cell comprises in their germline and/or genome an FcεR1α locus provided herein. In some embodiments, the mouse or ES cell comprises in their germline and/or genome an FcγR1α locus provided herein. In some embodiments, the mouse or ES cell comprises in their germline and/or genome an FcγR2a locus provided herein. In some embodiments, the mouse or ES cell comprises in their germline and/or genome an FcγR2b locus provided herein. In some embodiments, the mouse or ES cell comprises in their germline and/or genome an FcγR3a locus provided herein. In some embodiments, the mouse or ES cell comprises in their germline and/or genome an FcγR3b locus provided herein. In some embodiments, the mouse or ES cell comprises in their germline and/or genome an FcγR2c locus provided herein. In some embodiments, the mouse or ES cell is heterozygous for one or more of the loci, e.g., genetically engineered loci, provided herein. In some embodiments, the mouse or ES cell is homozygous for one or more of the loci, e.g., genetically engineered loci, provided herein.

In some embodiments, the mouse is a mouse of a C57BL strain. In some embodiments, the C57BL strain is selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a mouse of a 129 strain. In some embodiments, the 129 strain is selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. In some embodiments, the genetically modified mouse is a mix of a 129 strain and a C57BL strain. In some embodiments, the mouse is a mix of 129 strains and/or a mix of C57BL/6 strains. In some embodiments, the 129 strain of the mix is a 129S6 (129/SvEvTac) strain. In some embodiments, the mouse is a BALB strain (e.g., BALB/c). In some embodiments, the mouse is a mix of a BALB strain and another strain (e.g., a C57BL strain and/or a 129 strain). In some embodiments, the mice provided herein can be a mouse derived from any combination of the aforementioned strains.

The genetically modified mice and ES cells can be generated using any appropriate method known in the art. For example, such genetically modified mouse ES cells can be generated using VELOCIGENE® technology, which is described in U.S. Pat. Nos. 6,586,251, 6,596,541, 7,105,348, and Valenzuela et al. (2003) "High-throughput engineering of the mouse genome coupled with high-resolution expression analysis" *Nat. Biotech.* 21(6): 652-659, each of which is hereby incorporated by reference. Modifications can also be made using a genome targeted nuclease system, such as a CRISPR/Cas system, a transcription activator-like effector nuclease (TALEN) system or a zinc finger nuclease (ZFN) system. In some embodiments, modifications are made using a CRISPR/Cas system, as described, for example, in U.S. patent application Ser. Nos. 14/314,866, 14/515,503, 14/747,461 and 14/731,914, each of which is incorporated by reference. Exemplary methods of making such genetically modified mice and ES cells are also provided herein in Example 1.

ES cells described herein can then be used to generate a mouse using methods known in the art. For example, the mouse ES cells described herein can be used to generate genetically modified mice using the VELOCIMOUSE® method, as described in U.S. Pat. No. 7,294,754 and Poueymirou et al., *Nature Biotech* 25:91-99 (2007), each of which is hereby incorporated by reference. Resulting mice can be bread to homozygosity.

Methods of Testing Human Fcα-Containing Therapeutics

In certain aspects provided herein are methods of testing a therapeutic protein comprising a human Fcα domain (e.g., a human antibody or an Fcα fusion protein) comprising administering the therapeutic protein to a mouse provided herein. In some embodiments, provided herein are animal models for performing such methods.

In some embodiments, the administered human antibody or Fc fusion protein has an isotype and/or allotype that matches the isotype and/or allotype of Fc domain encoded by a human $C_H$ in the genetically modified IgH locus of the mouse provided herein. For example, in some embodiments, the agent is a human IgA1 antibody, and the mouse comprises a genetically modified IgH locus that comprises a $C_H$ gene segment encoding human IgA1 $C_H1$, hinge, $C_H2$ and $C_H3$ domains. In some embodiments, the agent is a human IgA2 antibody, and the mouse comprises a genetically modified IgH locus that comprises a $C_H$ gene segment encoding human IgA2 $C_H1$, hinge, $C_H2$ and $C_H3$ domains. In some embodiments, the agent is an antibody (e.g., an IgA1 or IgA2 antibody) that comprises a human heavy chain variable domain.

In some embodiments, the method comprises measuring one or more pharmacokinetic properties of the administered therapeutic protein. In some embodiments, the animal model used to determine the pharmacokinetic properties of the administered human antibody or fusion protein is a genetically modified mouse provided herein comprising a human FcαR locus.

In some embodiments, the one or more pharmacokinetic parameters include, but are not limited to, area under the plasma concentration versus time (AUC), in vivo recovery (IVR), clearance rate (CL), mean residence time (MRT), agent half-life (t½), and volume of distribution at steady state (Vss). In general, the pharmacokinetic properties of the administered therapeutic agent is determined by administering a selected dose of the therapeutic agent (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more) and then determining how the plasma concentration of the therapeutic agent changes over time (e.g., 0 hr, 6 hr, 1 day, 2 days, 3 days, 4 days, 5 days, 6 days, 7 days, 8 days, 9 days, 10 days, 11 days, or up to 30 or more days).

In some embodiments, the methods further comprise measuring the therapeutic efficacy of the administered therapeutic protein (e.g., the ability of an administered dose of the therapeutic protein to reduce or eliminate one or more disease symptoms in the animal model). In some embodiments, the animal model is a cancer model and disease symptoms can include, for example, tumor size, tumor metastasis, and/or animal survival. In some embodiments, the animal model is an autoimmune or inflammation model, and the disease symptoms can include, for example, levels of cytokine expression, proliferation of immune cells, tissue damage, and/or animal survival. In some embodiments, the animal model is an infectious disease model, and the disease symptoms can include, for example, levels of the infectious agent, tissue damage, and/or animal survival.

In some embodiments, the methods further comprise measuring the safety and dosing of the administered therapeutic protein (e.g., the extent to which an administered dose of the therapeutic protein produces one or more adverse effects in the animal model). Adverse effects include, but are not limited to, allergic reactions, alopecia, anaphylaxis, anemia, lack of appetite, loss of balance, bleeding, blood clots, difficulty breathing, bronchitis, bruising, low white blood cell count, low red blood cell count, low platelet count, cardiotoxicity, conjunctivitis, constipation, coughing, dehydration, diarrhea, electrolyte imbalance, loss of fertility, fever, hair loss, heart failure, infection, injection site reactions, iron deficiency, kidney failure, leukopenia, liver dysfunction, pneumonia, rapid heartbeat, rectal bleeding, seizures, weight loss, and weight gain. In some embodiments, provided herein is a method of measuring allergic reactions induced by a therapeutic agent using passive cutaneous anaphylaxis (PCA) and/or passive systemic anaphylaxis (PSA) models.

In some embodiments, the method further comprises measuring the extent to which the therapeutic protein induces one or more FcαR mediated responses in the mouse (e.g., the extent to which the therapeutic protein induces antibody-dependent cell-mediated cytotoxicity (ADCC)). For example, in certain embodiments provided herein is a method of screening a therapeutic agent comprising a human Fcα region of a human antibody comprising: (a) administering an agent comprising an Fcα region of a human antibody to a mouse provided herein, wherein the agent binds to a target cell in the mouse; (b) measuring antibody-dependent cell-mediated cytotoxicity (ADCC) of natural killer (NK) cells against the target cell; and (c) comparing the amount of ADCC in step (b) to a control, wherein increased target cell killing indicates the agent has increased ability to mediate ADCC.

In some embodiments, the method further comprises measuring the extent to which administration of the therapeutic protein induces an anti-human Fcα immune response in the mouse.

In some embodiments, the antibodies tested in the methods provided herein have human light chain variable domains. In some embodiments, the light chain variable domains are λ light chain variable domains. In some embodiments, the light chain variable domains are κ light chain variable domains. In some embodiments, the antibodies have human light chain constant domains. In some embodiments, the light chain constant domains are λ light chain constant domains. In some embodiments, the light chain constant domains are κ light chain constant domains. The sequences of human light chain constant domains are known in the art (see e.g., Kabat, E. A., et al. (1991) Sequences of Proteins of Immunological Interest, Fifth Edition, U.S. Department of Health and Human Services, NIH Publication No. 91-3242 and the IMGT database available at www.imgt.org).

In some embodiments, the therapeutic agent is administered to a mouse provided herein as part of a pharmaceutical composition e.g., a pharmaceutical composition, containing a human IgA antibody or Fc fusion protein formulated together with a pharmaceutically acceptable carrier.

The pharmaceutical compositions provided herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous or epidural injection as, for example, a sterile solution or suspension, or sustained-release formulation.

Pharmaceutical compositions suitable for parenteral administration comprise a human IgA antibody or Fc fusion protein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some embodiments, the compositions comprise a human antibody or Fc fusion protein in a concentration resulting in a w/v appropriate for a desired dose. The antibody may be present in the composition at a concentration of at least 1 mg/mL, at least 5 mg/mL, at least 10 mg/mL, at least 15 mg/mL, at least 20 mg/mL, at least 25 mg/mL, at least 30 mg/mL, at least 35 mg/mL, at least 40 mg/mL, at least 45 mg/mL, at least 50 mg/mL, at least 55 mg/mL, at least 60 mg/mL, at least 65 mg/mL, at least 70 mg/mL, at least 75 mg/mL, at least 80 mg/mL, at least 85 mg/mL, at least 90 mg/mL, at least 95 mg/mL, at least 100 mg/mL, at least 105 mg/mL, at least 110 mg/mL, at least 115 mg/mL, at least 120 mg/mL, at least 125 mg/mL, at least 130 mg/mL, at least 135 mg/mL, at least 140 mg/mL, at least 150 mg/mL, at least 200 mg/mL, at least 250 mg/mL, or at least 300 mg/mL.

In some embodiments, compositions are prepared by mixing a human IgA antibody or Fc fusion protein with optional physiologically acceptable carriers, excipients or stabilizers, including, but not limited to buffering agents, saccharides, salts, surfactants, solubilizers, polyols, diluents, binders, stabilizers, salts, lipophilic solvents, amino acids, chelators, preservatives, or the like (Goodman and Gilman's The Pharmacological Basis of Therapeutics, 12th edition, L. Brunton, et al. and Remington's Pharmaceutical Sciences, 16th edition, Osol, A. Ed. (1999)), in the form of lyophilized compositions or aqueous solutions at a desired final concentration. Acceptable carriers, excipients, or stabilizers are nontoxic to recipients at the dosages and concentrations employed, and include buffers such as histidine, phosphate, citrate, glycine, acetate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrolidone; amino acids such as glycine, glutamine, asparagine, histidine, arginine, or lysine; monosaccharides, disaccharides, and other carbohydrates including trehalose, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, polysorbate 80, PLURONICS® or polyethylene glycol (PEG).

In some embodiments, the buffering agent is histidine, citrate, phosphate, glycine, or acetate. The saccharide excipient may be trehalose, sucrose, mannitol, maltose or raffinose. The surfactant may be polysorbate 20, polysorbate 40, polysorbate 80, or Pluronic F68. The salt may be NaCl, KCl, MgCl2, or CaCl2).

In some embodiments, the composition comprises a buffering or pH adjusting agent to provide improved pH control. Such a composition may have a pH of between about 3.0 and about 9.0, between about 4.0 and about 8.0, between about 5.0 and about 8.0, between about 5.0 and about 7.0, between about 5.0 and about 6.5, between about 5.5 and about 8.0, between about 5.5 and about 7.0, or between about 5.5 and about 6.5. In a further embodiment, such a composition has a pH of about 3.0, about 3.5, about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.5, about 8.0, about 8.5, or about 9.0. In some embodiments, a composition has a pH of about 6.0. One of skill in the art understands that the pH of a composition generally should not be equal to the isoelectric point of a human antibody or Fc fusion protein to be used in the composition. Typically, the buffering agent is a salt prepared from an organic or inorganic acid or base. Representative buffering agents include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In addition, amino acid components can also function in a buffering capacity. Representative amino acid components which may be utilized in the composition as buffering agents include, but are not limited to, glycine and histidine. In some embodiments, the buffering agent is chosen from histidine, citrate, phosphate, glycine, and acetate. In some embodiments, the buffering agent is histidine. In another specific embodiment, the buffering agent is citrate. In yet another specific embodiment, the buffering agent is glycine. The purity of the buffering agent should be at least 98%, or at least 99%, or at least 99.5%. As used herein, the term "purity" in the context of histidine and glycine refers to chemical purity of histidine or glycine as understood in the art, e.g., as described in The Merck Index, 13th ed., O'Neil et al. ed. (Merck & Co., 2001).

In some embodiments, the composition comprises histidine as a buffering agent. In some embodiments, the histidine is present in the composition at a concentration of at least about 1 mM, at least about 5 mM, at least about 10 mM, at least about 20 mM, at least about 30 mM, at least about 40 mM, at least about 50 mM, at least about 75 mM, at least about 100 mM, at least about 150 mM, or at least about 200 mM histidine. In another embodiment, a composition comprises between about 1 mM and about 200 mM, between about 1 mM and about 150 mM, between about 1 mM and about 100 mM, between about 1 mM and about 75 mM, between about 10 mM and about 200 mM, between about 10 mM and about 150 mM, between about 10 mM and about 100 mM, between about 10 mM and about 75 mM, between about 10 mM and about 50 mM, between about 10 mM and about 40 mM, between about 10 mM and about 30 mM, between about 20 mM and about 75 mM, between about 20 mM and about 50 mM, between about 20 mM and about 40 mM, or between about 20 mM and about 30 mM histidine. In a further embodiment, the composition comprises about 1 mM, about 5 mM, about 10 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 150 mM, or about 200 mM histidine. In some embodiments, a composition may comprise about 10 mM, about 25 mM, or no histidine.

In some embodiments, the composition comprises a carbohydrate excipient. Carbohydrate excipients can act, e.g., as viscosity enhancing agents, stabilizers, bulking agents, solubilizing agents, and/or the like. Carbohydrate excipients are generally present at between about 1% to about 99% by weight or volume, e.g., between about 0.1% to about 20%, between about 0.1% to about 15%, between about 0.1% to about 5%, between about 1% to about 20%, between about 5% to about 15%, between about 8% to about 10%, between about 10% and about 15%, between about 15% and about 20%, between 0.1% to 20%, between 5% to 15%, between 8% to 10%, between 10% and 15%, between 15% and 20%, between about 0.1% to about 5%, between about 5% to about 10%, or between about 15% to about 20%. In still other specific embodiments, the carbohydrate excipient is present at 1%, or at 1.5%, or at 2%, or at 2.5%, or at 3%, or at 4%, or at 5%, or at 10%, or at 15%, or at 20%.

In some embodiments, the composition comprises a carbohydrate excipient. Carbohydrate excipients suitable for use in the compositions include, but are not limited to, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and the like. In some embodiments, the carbohydrate excipients for use in the compositions provided herein are chosen from sucrose, trehalose, lactose, mannitol, and raffinose. In some embodiments, the carbohydrate excipient is trehalose. In another specific embodiment, the carbohydrate excipient is mannitol. In yet another specific embodiment, the carbohydrate excipient is sucrose. In still another specific embodiment, the carbohydrate excipient is raffinose. The purity of the carbohydrate excipient should be at least 98%, or at least 99%, or at least 99.5%.

In some embodiments, the composition comprises trehalose. In some embodiments, a composition comprises at least about 1%, at least about 2%, at least about 4%, at least about 8%, at least about 20%, at least about 30%, or at least about 40% trehalose. In another embodiment, a composition comprises between about 1% and about 40%, between about 1% and about 30%, between about 1% and about 20%, between about 2% and about 40%, between about 2% and about 30%, between about 2% and about 20%, between about 4% and about 40%, between about 4% and about 30%, or between about 4% and about 20% trehalose. In a further embodiment, a composition comprises about 1%, about 2%, about 4%, about 6%, about 8%, about 15%, about 20%, about 30%, or about 40% trehalose. In some embodiments, a composition comprises about 4%, about 6% or about 15% trehalose.

In some embodiments, the composition comprises an excipient. In some embodiments, a composition comprises at least one excipient chosen from: sugar, salt, surfactant, amino acid, polyol, chelating agent, emulsifier and preservative. In some embodiments, a composition comprises a salt, e.g., a salt selected from: NaCl, KCl, CaCl$_2$), and MgCl2. In some embodiments, the composition comprises NaCl.

In some embodiments, the composition comprises an amino acid, e.g., lysine, arginine, glycine, histidine or an amino acid salt. The composition may comprise at least about 1 mM, at least about 10 mM, at least about 25 mM, at least about 50 mM, at least about 100 mM, at least about 150 mM, at least about 200 mM, at least about 250 mM, at least about 300 mM, at least about 350 mM, or at least about 400 mM of an amino acid. In another embodiment, the composition may comprise between about 1 mM and about 100 mM, between about 10 mM and about 150 mM, between about 25 mM and about 250 mM, between about 25 mM and about 300 mM, between about 25 mM and about 350 mM, between about 25 mM and about 400 mM, between about 50 mM and about 250 mM, between about 50 mM and about 300 mM, between about 50 mM and about 350 mM, between about 50 mM and about 400 mM, between about 100 mM and about 250 mM, between about 100 mM and about 300 mM, between about 100 mM and about 400 mM, between about 150 mM and about 250 mM, between about 150 mM and about 300 mM, or between about 150 mM and about 400 mM of an amino acid. In a further embodiment, a composition comprises about 1 mM, 1.6 mM, 25 mM, about 50 mM, about 100 mM, about 150 mM, about 200 mM, about 250 mM, about 300 mM, about 350 mM, or about 400 mM of an amino acid.

In some embodiments, the composition comprises a surfactant. The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. Pharmaceutically acceptable surfactants like polysorbates (e.g., polysorbates 20 or 80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA® series (Mona Industries, Inc., Paterson, N.J.), polyethyl glycol, polypropyl glycol, and copolymers of ethylene and propylene glycol (e.g., PLURONICS® PF68, etc.), can optionally be added to the compositions to reduce aggregation. In some embodiments, a composition comprises Polysorbate 20, Polysorbate 40, Polysorbate 60, or Polysorbate 80. Surfactants are particularly useful if a pump or plastic container is used to administer the composition. The presence of a pharmaceutically acceptable surfactant mitigates the propensity for the protein to aggregate. The compositions may comprise a polysorbate which is at a concentration ranging from between about 0.0010% to about 10%, or about 0.0010% to about 0.10%, or about 0.010% to about 0.10%. In other specific embodiments, the compositions comprise a polysorbate which is at a concentration of 0.001%, or 0.002%, or 0.003%, or 0.004%, or 0.005%, or 0.006%, or 0.007%, or 0.008%, or 0.009%, or 0.01%, or 0.015%, or 0.02%.

In some embodiments, the composition comprises other excipients and/or additives including, but not limited to, diluents, binders, stabilizers, lipophilic solvents, preservatives, adjuvants, or the like. Pharmaceutically acceptable excipients and/or additives may be used in the compositions provided herein. Commonly used excipients/additives, such as pharmaceutically acceptable chelators (for example, but not limited to, EDTA, DTPA or EGTA) can optionally be added to the compositions to reduce aggregation. These additives are particularly useful if a pump or plastic container is used to administer the composition.

In some embodiments, the composition comprises a preservative. Preservatives, such as phenol, m-cresol, p-cresol, o-cresol, chlorocresol, benzyl alcohol, phenylmercuric nitrite, phenoxyethanol, formaldehyde, chlorobutanol, magnesium chloride (for example, but not limited to, hexahydrate), alkylparaben (methyl, ethyl, propyl, butyl and the like), benzalkonium chloride, benzethonium chloride, sodium dehydroacetate and thimerosal, or mixtures thereof can optionally be added to the compositions at any suitable concentration such as between about 0.001% to about 5%, or any range or value therein. The concentration of preservative used in the compositions is a concentration sufficient to yield a microbial effect. Such concentrations are dependent on the preservative selected and are readily determined by the skilled artisan.

In some embodiments, the composition is isotonic with human blood, wherein the compositions have essentially the same osmotic pressure as human blood. Such isotonic compositions will generally have an osmotic pressure from about 250 mOSm to about 350 mOSm. Isotonicity can be measured by, for example, using a vapor pressure or ice-freezing type osmometer. Tonicity of a composition is adjusted by the use of tonicity modifiers. "Tonicity modifiers" are those pharmaceutically acceptable inert substances that can be added to the composition to provide an isotonity of the composition. Tonicity modifiers suitable for the compositions provided herein include, but are not limited to, saccharides, salts and amino acids.

In some embodiments, the composition is a pyrogen-free composition which is substantially free of endotoxins and/or related pyrogenic substances. Endotoxins include toxins that are confined inside a microorganism and are released only when the microorganisms are broken down or die. Pyrogenic substances also include fever-inducing, thermostable substances from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with proteins of interest (e.g., antibodies), even trace amounts of harmful and dangerous endotoxin must be removed. In some embodiments, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg.

When used for in vivo administration, the composition described herein should be sterile. The composition may be sterilized by various sterilization methods, including sterile filtration, radiation, etc. In some embodiments, composition is filter-sterilized with a presterilized 0.22-micron filter. Sterile compositions for injection can be formulated according to conventional pharmaceutical practice as described in "Remington: The Science & Practice of Pharmacy", 21st ed., Lippincott Williams & Wilkins, (2005). Compositions comprising proteins of interest (e.g., antibodies) such as those disclosed herein, ordinarily will be stored in lyophilized form or in solution. It is contemplated that sterile compositions comprising proteins of interest (e.g., antibody) are placed into a container having a sterile access port, for example, an intravenous solution bag or vial having an adapter that allows retrieval of the composition, such as a stopper pierceable by a hypodermic injection needle. In some embodiments, a composition is provided as a pre-filled syringe.

In some embodiments, the composition is a lyophilized formulation. The term "lyophilized" or "freeze-dried" includes a state of a substance that has been subjected to a drying procedure such as lyophilization, where at least 50% of moisture has been removed.

Regardless of the route of administration selected, agents provided herein, which may be used in a suitable hydrated form, and/or the pharmaceutical compositions of the provided herein, are formulated into pharmaceutically-acceptable dosage forms by conventional methods known to those of skill in the art.

In the methods provided herein the human antibody, Fc fusion protein and/or pharmaceutical compositions may be delivered by any suitable route of administration, including orally, nasally, as by, for example, a spray, rectally, intravaginally, parenterally, intracisternally and topically, as by powders, ointments or drops, including buccally and sublingually. In some embodiments, the pharmaceutical compositions are delivered generally (e.g., via oral or parenteral administration).

In some embodiments, actual dosage levels of the active ingredients in the pharmaceutical compositions described herein may be varied so as to determine an amount of the active ingredient which is effective to achieve the desired therapeutic response in the animal model, composition, and mode of administration, without being toxic in the animal model.

For example, in certain embodiments, mice described herein are used to determine the pharmacokinetic profiles of one or more human antibody candidates. In various embodiments, one or more mice as described herein and one or more control or reference mice are each exposed to one or more human antibody candidates at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Blood is isolated from mice (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered candidate therapeutic antibodies or Fc fusion polypeptides using samples obtained from mice as described herein including, but not limited to, total IgA, anti-therapeutic antibody response, agglutination, etc.

In various embodiments, mice as described herein are used to measure the therapeutic effect of blocking or modulating the activity of a polypeptide of interest and the effect on gene expression as a result of cellular changes or, in the context of a receptor polypeptide, the density of a receptor polypeptide on the surface of cells in the mice. In various embodiments, a mouse as described herein or cells isolated therefrom are exposed to a candidate therapeutic that binds a polypeptide of interest and, after a subsequent period of time, analyzed for effects on specific cellular processes that are associated with said polypeptide of interest, for example, ligand-receptor interactions or signal transduction.

Mice as described herein provide an improved in vivo system for development and selection of human IgA antibodies or Fc fusion polypeptides for use in oncology and/or infectious diseases. In various embodiments, mice as described herein and control mice (e.g., having a genetic modification that is different than as described herein or no genetic modification, i.e., wild-type) may be implanted with a tumor (or tumor cells) or infected with a virus (e.g., influenza, HIV, HCV, HPV, etc.). Following implantation or infection, mice may be administered a candidate therapeutic. The tumor or virus may be allowed sufficient time to be established in one or more locations within the mice prior to administration of a candidate therapeutic. Alternatively and/or additionally, the immune response may be monitored in such mice so as to characterize and select potential human antibodies that may be developed as a therapeutic.

Methods of Making Genetically Modified Mice and ES Cells

In certain aspects, provided herein are methods of making mice and ES cells that comprise one or more of the genetically modified loci provided here. The exemplary methods of making genetically modified mice and ES cells provided herein are described in the description, examples, and/or figures herein. For example, in some embodiments, provided herein are methods of making mice and ES cells that comprise an FcαR locus provided herein. In some embodiments, the FcαR locus is inserted into mouse chromosome 7 between the Pira6 gene and the Ncr1 gene. In some embodiments, the FcαR locus is inserted into mouse chromosome 7 between nucleotide residues 4,303,905-4,312,280 (GRCm38 assembly).

In some embodiments, provided herein are methods of making mice and ES cells that further comprise a humanized CD79a locus provided herein and/or a humanized CD79b locus provided herein. In some embodiments, provided herein are methods of making mice and ES cells that further comprise a human or humanized FcRn locus provided herein and/or a human or humanized β2M locus provided herein. In some embodiments, provided herein are methods of making mice and ES cells that further comprise a human or humanized FcεR1α locus provided herein. In certain embodiments, provided herein are methods of making mice and ES cells that further comprise a human or humanized FcγR1α locus provided herein. In some embodiments, provided herein are methods of making mice and ES cells that further comprise a human or humanized FcγR2a locus provided herein, a human or humanized FcγR2b locus provided herein, a human or humanized FcγR2c locus provided herein, a human or humanized FcγR3a locus provided herein, and/or a human or humanized FcγR3b locus provided herein. In some embodiments, provided herein are methods of making mice and ES cells that further comprise a human or humanized heavy and/or light chain locus provided herein. The exemplary methods of making genetically modified mice and ES cells provided herein are described in the description, examples, and/or figures herein.

Kits

Provided herein a pack or kit comprising one or more containers filled with at least one mouse, mouse cell, DNA fragment and/or targeting vector as described in the description, examples, and/or figures herein. Kits may be used in any applicable method (e.g., a research method). Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, (c) a contract that governs the transfer of materials and/or biological products (e.g., a mouse or mouse cell as described herein) between two or more entities and combinations thereof.

Exemplary Embodiments

According to exemplary embodiment 1, provided herein is a mouse comprising in its genome an Fc alpha receptor (FcαR) locus positioned in the mouse leukocyte receptor complex (LRC), wherein the FcαR locus comprises a nucleic acid sequence encoding a FcαR polypeptide comprising a human extracellular domain and a human or rodent cytoplasmic domain.

According to exemplary embodiment 2, provided herein is the mouse of embodiment 1, wherein the FcαR locus is positioned in an intergenic region between the gene loci for the Tthy1 protein and the Rdh13 protein.

According to exemplary embodiment 3, provided herein is the mouse of embodiment 1 or 2, wherein the FcαR locus is positioned in an intergenic region between the gene loci for the Lilra5 protein and the Gp6 protein.

According to exemplary embodiment 4, provided herein is the mouse of any one of embodiments 1-3, wherein the FcαR locus is positioned in an intergenic region between the gene loci for the Pira6 protein and the Ncr1 protein, such as between coding nucleic acid sequences for the Pira6 protein and the Ncr1 protein.

According to exemplary embodiment 5, provided herein is the mouse of embodiment 4, wherein the intergenic region is the 54 kb region between the Pira6 and Ncr1 loci.

According to exemplary embodiment 6, provided herein is the mouse of any one of embodiments 1-5, wherein the FcαR locus is positioned between coordinates 4,303,905-4,312,280 on mouse chromosome 7 (+strand, GRCm38 assembly).

According to exemplary embodiment 7, provided herein is the mouse of any one of embodiments 1-6, wherein the FcαR locus comprises a nucleic acid sequence encoding a human FcαR polypeptide.

According to exemplary embodiment 8, provided herein is the mouse of any one of embodiments 1-7, wherein the FcαR locus comprises human exons 1-5 of the human Fc alpha receptor gene.

According to exemplary embodiment 9, provided herein is the mouse of any one of embodiments 1-6, wherein the FcαR locus comprises a non-coding portion of non-mouse rodent FcαR exon 1, a coding portion of human FcαR exons 1 and 2, human FcαR exons 3 and 4, and non-mouse rodent FcαR exon 5.

According to exemplary embodiment 10, provided herein is the mouse of embodiment 7 or 8, wherein the human or humanized FcαR receptor locus comprises a genomic sequence found between coordinates 54,862,297 and 54,906,185 on human chromosome 19 (+strand, GRCh38 assembly).

According to exemplary embodiment 11a, provided herein is the mouse of embodiment 7 or 8, wherein the FcαR locus further comprises a nucleic acid sequence present in a human KIR3DL2 gene. Further, according to exemplary embodiment 11b, provided herein the mouse of embodiment 7, 8, or 11a, wherein the FcαR locus further comprises a nucleic acid sequence present in the 5'UTR of a human NCR1 gene.

According to exemplary embodiment 12, provided herein is the mouse of any one of embodiments 1-11, wherein the mouse expresses the FcαR polypeptide on mouse neutrophils, monocytes, macrophages, eosinophils, and plasmacytoid dendritic cells.

According to exemplary embodiment 13, provided herein is the mouse of any one of embodiments 1-12, wherein the mouse is heterozygous for the FcαR locus.

According to exemplary embodiment 14, provided herein is the mouse of any one of embodiments 1-12, wherein the mouse is homozygous for the FcαR locus.

According to exemplary embodiment 15, provided herein is the mouse of any one of embodiments 1-14, further comprising in its genome a human or humanized Fc gamma receptor (FcγR) locus, a human or humanized IgH locus, a human or humanized Igκ locus, a human or humanized Igλ locus, a human or humanized FcRn locus, a human or humanized β2M locus, and/or a human or humanized FcεR1α locus.

According to exemplary embodiment 16, provided herein is the mouse of embodiment 15, wherein the mouse comprises in its genome a human or humanized FcγR locus comprising a nucleic acid sequence encoding a human or humanized FcγR.

According to exemplary embodiment 17, provided herein is the mouse of embodiment 16, wherein the human or humanized FcγR locus comprises a nucleic acid sequence encoding one or more low affinity FcγR selected from Fc gamma receptor 2a (FcγR2a), Fc gamma receptor 2b (FcγR2b), Fc gamma receptor 3a (FcγR3a), Fc gamma receptor 3b (FcγR3b), and/or Fc gamma receptor 2c (FcγR2c).

According to exemplary embodiment 18, provided herein is the mouse of embodiment 16, wherein the human or humanized FcγR locus comprises a nucleic acid sequence encoding one or more FcγR selected from a human or humanized Fc gamma receptor 1 alpha (FcγR1α), Fc gamma receptor 2a (FcγR2a), Fc gamma receptor 2b (FcγR2b), Fc gamma receptor 3a (FcγR3a), Fc gamma receptor 3b (FcγR3b), and/or Fc gamma receptor 2c (FcγR2c).

According to exemplary embodiment 19, provided herein is the mouse of any one of embodiments 16-18, wherein the human or humanized FcγR comprises a human extracellular domain.

According to exemplary embodiment 20, provided herein is the mouse of any one of embodiments 16-19, wherein the human or humanized FcγR comprises a mouse transmembrane domain.

According to exemplary embodiment 21, provided herein is the mouse of any one of embodiments 16-19, wherein the human or humanized FcγR comprises a human transmembrane domain.

According to exemplary embodiment 22, provided herein is the mouse of any one of embodiments 16-21, wherein the human or humanized FcγR comprises a mouse cytoplasmic domain.

According to exemplary embodiment 23, provided herein is the mouse of any one of embodiments 16-21, wherein the human or humanized FcγR comprises a human cytoplasmic domain.

According to exemplary embodiment 24, provided herein is the mouse of any one of embodiment 16-23, wherein the human or humanized FcγR locus is positioned at an endogenous mouse FcγR locus.

According to exemplary embodiment 25, provided herein is the mouse of embodiment 24, wherein the nucleic acid sequence encoding the human or humanized FcγR replaces all or part of an endogenous mouse FcγR gene.

According to exemplary embodiment 26, provided herein is the mouse of embodiment 25, wherein the nucleic acid sequence encoding the human or humanized FcγR comprises a nucleic acid sequence encoding a human FcγR extracellular domain that replaces an endogenous nucleic acid sequence encoding a mouse FcγR extracellular domain.

According to exemplary embodiment 27, provided herein is the mouse of any one of embodiments 15-26, wherein the mouse does not express a mouse FcγR.

According to exemplary embodiment 28, provided herein is the mouse of any one of embodiments 15-27, wherein the mouse is heterozygous for the human or humanized FcγR locus, the human or humanized IgH locus, the human or humanized Igκ locus, the human or humanized Igλ locus, the human or humanized FcRn locus, the human or humanized β2M locus, and/or the human or humanized FcεR1α locus.

According to exemplary embodiment 29, provided herein is the mouse of any one of embodiments 15-27, wherein the mouse is homozygous for the human or humanized FcγR locus, the human or humanized IgH locus, the human or humanized Igκ locus, the human or humanized Igλ locus, the human or humanized FcRn locus, the human or humanized β2M locus, and/or the human or humanized FcεR1α locus.

According to exemplary embodiment 30, provided herein is a mouse embryonic stem cell (ES cell) comprising in its genome an Fc alpha receptor (FcαR) locus positioned in the leukocyte receptor complex (LRC) of the mouse genome, wherein the FcαR locus comprises a nucleic acid sequence encoding a FcαR polypeptide comprising a human extracellular domain and a human or rodent cytoplasmic domain.

According to exemplary embodiment 31, provided herein is the mouse ES cell of embodiment 30, wherein the FcαR locus is positioned in an intergenic region between the gene loci for the Tthy1 protein and the Rdh13 protein.

According to exemplary embodiment 32, provided herein is the mouse ES cell of embodiment 31 or 32, wherein the FcαR locus is positioned in an intergenic region between the gene loci for the Lilra5 protein and the Gp6 protein.

According to exemplary embodiment 33, provided herein is the mouse ES cell of any one of embodiments 30-32, wherein the Fc alpha receptor (FcαR) locus is positioned in an intergenic region between the gene loci for the Pira6 protein and the Ncr1 protein, such as between the coding nucleic acid sequences for the Pira6 protein and the Ncr1 protein.

According to exemplary embodiment 34, provided herein is the mouse ES cell of embodiment 33 wherein the intergenic region is the 54 kb region between the Pira6 and Ncr1 loci.

According to exemplary embodiment 35, provided herein is the mouse ES cell of any one of embodiments 30-34 wherein the FcαR locus is positioned between coordinates 4,303,905-4,312,280 on mouse chromosome 7 (+strand, GRCm38 assembly).

According to exemplary embodiment 36, provided herein is the mouse ES cell of any one of embodiments 30-35, wherein the FcαR locus comprises a nucleic acid sequence encoding a human FcαR polypeptide.

According to exemplary embodiment 37, provided herein is the mouse ES cell of any one of embodiments 30-36, wherein the FcαR locus comprises human exons 1-5 of the human Fc alpha receptor gene.

According to exemplary embodiment 38, provided herein is the mouse ES cell of any one of embodiments 30-35, wherein the FcαR locus comprises a non-coding portion of non-mouse rodent FcαR exon 1, a coding portion of human FcαR exons 1 and 2, human FcαR exons 3 and 4, and non-mouse rodent FcαR exon 5.

According to exemplary embodiment 39, provided herein is the mouse ES cell of embodiment 36 or 37, wherein the human or humanized FcαR receptor locus comprises a genomic sequence found between coordinates 54,862,297 and 54,906,185 on human chromosome 19 (+strand, GRCh38 assembly).

According to exemplary embodiment 40a, provided herein is the mouse ES cell of embodiment 36 or 37, wherein the FcαR locus further comprises a nucleic acid sequence present in a human KIR3DL2 gene. Further, according to exemplary embodiment 40b, provided herein the mouse ES cell of embodiment 36, 37, or 40a, wherein the FcαR locus further comprises a nucleic acid sequence present in the 5'UTR of a human NCR1 gene.

According to exemplary embodiment 41, provided herein is the mouse ES cell of any one of embodiments 30-40, wherein the ES cell is heterozygous for the FcαR locus.

According to exemplary embodiment 42, provided herein is the mouse ES cell of any one of embodiments 30-40, wherein the ES cell is homozygous for the FcαR locus.

According to exemplary embodiment 43, provided herein is the mouse ES cell of any one of embodiments 30-42, further comprising in its genome a human or humanized Fc gamma receptor (FcγR) locus, a human or humanized IgH locus, a human or humanized Igκ locus, a human or humanized Igλ locus, a human or humanized FcRn locus, a human or humanized β2M locus, and/or a human or humanized FcεR1α locus.

According to exemplary embodiment 44, provided herein is the mouse ES cell of embodiment 43, wherein the mouse ES cell comprises in its genome a human or humanized FcγR locus comprising a nucleic acid sequence encoding a human or humanized FcγR.

According to exemplary embodiment 45, provided herein is the mouse ES cell of embodiment 44, wherein the human or humanized FcγR locus comprises a nucleic acid sequence encoding one or more low affinity FcγR selected from Fc gamma receptor 2a (FcγR2a), Fc gamma receptor 2b (FcγR2b), Fc gamma receptor 3a (FcγR3a), Fc gamma receptor 3b (FcγR3b), and/or Fc gamma receptor 2c (FcγR2c).

According to exemplary embodiment 46, provided herein is the mouse ES cell of embodiment 44, wherein the human or humanized FcγR locus comprises a nucleic acid sequence encoding one or more FcγR selected from a human or humanized Fc gamma receptor 1 alpha (FcγR1α), Fc gamma receptor 2a (FcγR2a), Fc gamma receptor 2b (FcγR2b), Fc gamma receptor 3a (FcγR3a), Fc gamma receptor 3b (FcγR3b), and/or Fc gamma receptor 2c (FcγR2c).

According to exemplary embodiment 47, provided herein is the mouse ES cell of any one of embodiments 44-46, wherein the human or humanized FcγR comprises a human extracellular domain.

According to exemplary embodiment 48, provided herein is the mouse ES cell of any one of embodiments 44-47, wherein the human or humanized FcγR comprises a mouse transmembrane domain.

According to exemplary embodiment 49, provided herein is the mouse ES cell of any one of embodiments 44-47, wherein the human or humanized FcγR comprises a human transmembrane domain.

According to exemplary embodiment 50, provided herein is the mouse ES cell of any one of embodiments 44-49, wherein the human or humanized FcγR comprises a mouse cytoplasmic domain.

According to exemplary embodiment 51, provided herein is the mouse ES cell of any one of embodiments 44-49, wherein the human or humanized FcγR comprises a human cytoplasmic domain.

According to exemplary embodiment 52, provided herein is the mouse ES cell of any one of embodiments 44-51, wherein the human or humanized FcγR locus is positioned at an endogenous mouse FcγR locus.

According to exemplary embodiment 53, provided herein is the mouse ES cell of embodiment 52, wherein the nucleic acid sequence encoding the human or humanized FcγR replaces all or part of an endogenous mouse FcγR gene.

According to exemplary embodiment 54, provided herein is the mouse ES cell of embodiment 53, wherein the nucleic acid sequence encoding the human or humanized FcγR comprises a nucleic acid sequence encoding a human FcγR extracellular domain that replaces an endogenous nucleic acid sequence encoding a mouse FcγR extracellular domain.

According to exemplary embodiment 55, provided herein is the mouse ES cell of any one of embodiments 43-54, wherein the mouse is heterozygous for the human or humanized FcγR locus, the human or humanized IgH locus, the human or humanized Igκ locus, the human or humanized Igλ locus, the human or humanized FcRn locus, the human or humanized β2M locus, and/or the human or humanized FcεR1α locus.

According to exemplary embodiment 56, provided herein is the mouse ES cell of any one of embodiments 43-54, wherein the mouse is homozygous for the human or humanized FcγR locus, the human or humanized IgH locus, the human or humanized Igκ locus, the human or humanized Igλ locus, the human or humanized FcRn locus, the human or humanized β2M locus, and/or the human or humanized FcεR1α locus.

According to exemplary embodiment 57, provided herein is a method of testing a human IgA antibody or an Fcα fusion polypeptide comprising administering the IgA antibody or Fcα fusion polypeptide to a mouse of any one of embodiments 1 to 29.

According to exemplary embodiment 58, provided herein is the method of embodiment 57 further comprising measuring one or more pharmacokinetic properties of the administered human IgA antibody or Fcα fusion polypeptide.

According to exemplary embodiment 59, provided herein is the method of embodiment 58, wherein the one or more pharmacokinetic properties are selected from one or more of area under the plasma concentration versus time (AUC), in vivo recovery (IVR), clearance rate (CL), mean residence time (MRT), agent half-life (t½), and/or volume of distribution at steady state (Vss).

According to exemplary embodiment 60, provided herein is the method of any one of embodiments 57-59 further comprising measuring the therapeutic efficacy of the administered human antibody or Fcα fusion polypeptide.

According to exemplary embodiment 61, provided herein is the method of any one of embodiments 57-60 further comprising administering a plurality of doses of the human antibody or Fcα fusion polypeptide and determining a therapeutic efficacy of each dose of the human antibody or Fcα fusion polypeptide.

According to exemplary embodiment 62, provided herein is the method of any one of embodiments 57-61 further comprising administering a plurality of doses of the human antibody or Fcα fusion polypeptide and determining the safety of each dose of the human antibody or Fcα fusion polypeptide.

According to exemplary embodiment 63, provided herein is the method of any one of embodiments 57-62 further comprising administering a plurality of doses of the human antibody or Fcα fusion polypeptide and determining the tolerability of each dose of the human antibody or Fcα fusion polypeptide.

According to exemplary embodiment 64, provided herein is the method of any one of embodiments 57-63 further comprising measuring one or more Fc receptor mediated responses in the mouse.

According to exemplary embodiment 65, provided herein is the method of embodiment 64, wherein the one or more Fc receptor mediated response is an antibody-dependent cell-mediated cytotoxicity (ADCC) response.

According to exemplary embodiment 66, provided herein is the method of any one of embodiments 57-65, wherein the human antibody binds to a target cell in the mouse, and further comprising measuring antibody-dependent cell-mediated cytotoxicity (ADCC) of natural killer (NK) cells against the target cell and comparing the amount of ADCC to a control, wherein increased target cell killing indicates the agent has increased ability to mediate ADCC.

According to exemplary embodiment 67, provided herein is the method of any one of embodiments 57-66, further comprising measuring the immune response generated by the mouse against the human antibody.

According to exemplary embodiment 68, provided herein is a method of modifying a mouse genome, the method comprising: inserting an Fc alpha receptor (FcαR) locus into the leukocyte receptor complex (LRC) of a mouse genome, thereby modifying the mouse genome, wherein the FcαR locus comprises a nucleic acid sequence encoding an FcαR polypeptide comprising a human extracellular domain and a human or rodent cytoplasmic domain.

According to exemplary embodiment 69, provided herein is the method of embodiment 68, wherein the FcαR locus comprises a nucleic acid sequence encoding a human or humanized FcαR polypeptide.

According to exemplary embodiment 70, provided herein is the method of embodiment 68 or 69, wherein the FcαR locus is positioned in an intergenic region between the gene loci for the Tthy1 protein and the Rdh13 protein.

According to exemplary embodiment 71, provided herein is the method of any one of embodiments 68-70, wherein the FcαR locus is positioned in an intergenic region between the gene loci for the Lilra5 protein and the Gp6 protein.

According to exemplary embodiment 72, provided herein is the method of any one of embodiments 68-71, wherein the FcαR locus is positioned in an intergenic region between the gene loci for the Pira6 protein and the Ncr1 protein, such as between the coding nucleic acid sequences for the Pira6 protein and the Ncr1 protein.

According to exemplary embodiment 73, provided herein is the method of embodiment 72, wherein the intergenic region is the 54 kb region between the Pira6 and Ncr1 loci.

According to exemplary embodiment 74, provided herein is the method of any one of embodiments 68-73, wherein the FcαR locus is between coordinates 4,303,905-4,312,280 on mouse chromosome 7 (+strand, GRCm38 assembly).

According to exemplary embodiment 75, provided herein is a method of making a mouse comprising an Fc alpha receptor (FcαR) locus, the method comprising: generating a mouse ES cell of any one of embodiments 30-56; and generating a mouse from said ES cell.

EXAMPLES

Example 1.1: Genetic Engineering of Mice Comprising Human or Humanized FcαR

Figure 1B:
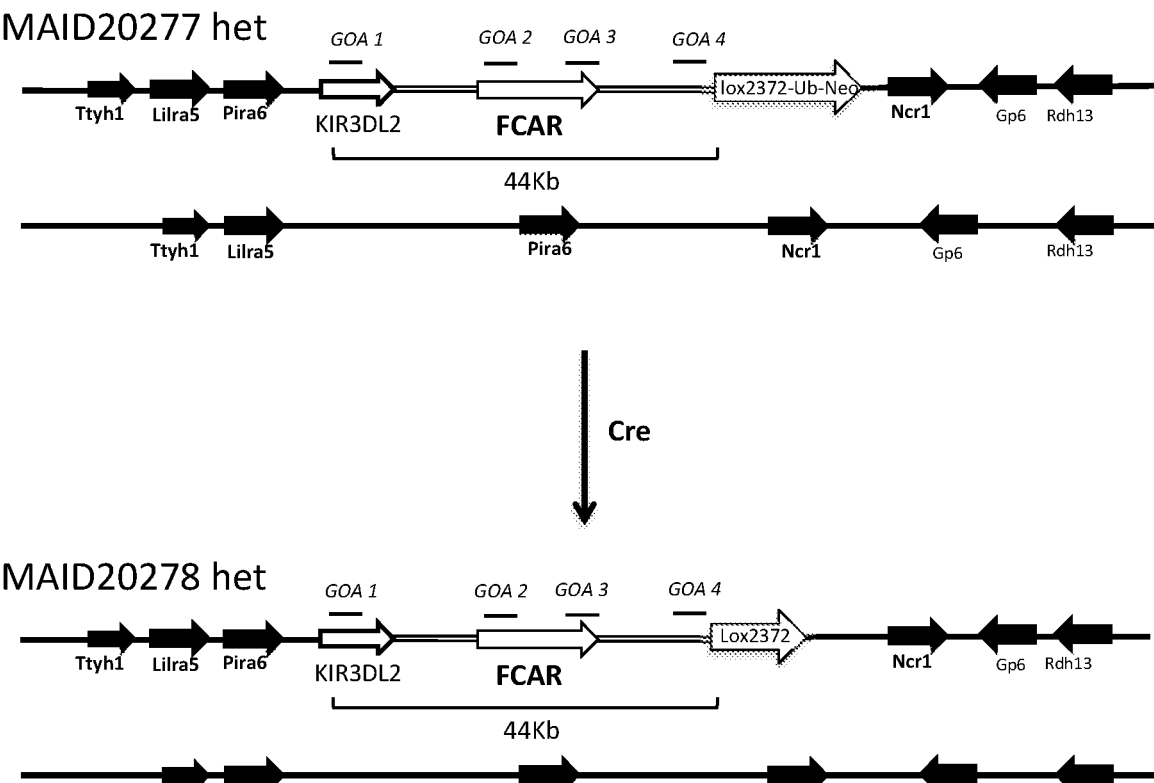
FIG. 1B is a diagram (not to scale) showing the treatment of ES cells heterozygous for the insertion of the MAID20277 cassette in a mouse genome with a CRE recombinase which causes the deletion of the selective marker, thereby producing an ES cell heterozygous for the MAID20278 cassette. The names and locations of the primers and probes used in a modification of allele (MOA) assay (described in the Examples) are indicated as short lines above the diagram.

Targeting vectors comprising a nucleic acid sequence encoding a human FcαR (MAID20277 and MAID20278) cassettes were generated. MAID20277 and MAID20278 were identical except that MAID20277 retained a selection marker (i.e., neomycin resistance). Briefly, a Human FCAR gene was introduced into the mouse genome using VELOCIGENE® technology (see, e.g., U.S. Pat. No. 6,586, 251 and Valenzuela et al. (2003) *Nat. Biotech.* 21(6): 652-659, the contents of both are incorporated herein by reference in their entirety). A 44 kb genomic sequence of human FCAR, including promoter, was inserted in the mouse LRC locus located between mouse Pira6 and Ncr1 genes on mouse chromosome 7, between coordinates chr7:4,303,905-4,312,280 (+strand; GRCm38 assembly) (FIGS. 1A and 1B).

More specifically, mouse homology arms were made by PCR amplification using BAC clone RP23-458i16 as the template and are indicated in Table 1.

TABLE 1

| Homology Arm | 5' primer | 3' primer | Coordinates (GRCm38 assembly) |
|---|---|---|---|
| 5'; 5044 bp | GGCTTCAAACTCAGACCTGCAT (SEQ ID NO: 1) | CACAGAGAGGGGAGTGCTGAA (SEQ ID NO: 2) | chr7: 4,298,861-4,303,904 |
| 3'; 5595 bp | TATGAATGCAGGTAAGGGGGA (SEQ ID NO: 3) | ACAGTTGAGCAAGCGTCCTT (SEQ ID NO: 4) | chr7: 4,312,281-4,317,875 |

The mouse homology arms were assembled into a construct containing, from 5' to 3': the 5' arm, a spectinomycin-resistance cassette flanked by I-CeuI and PI-SceI homing endonuclease sites, the 3' arm, and a chloramphenicol-resistance cassette (Construct A). In a later step of genetic engineering, the spectinomycin-resistance cassette in Construct A was replaced by a human FCAR-containing insert.

The human insert containing the entire FCAR gene and flanking sequences was made by two sequential bacterial homologous recombination (BHR) modifications of BAC clone CTD-3161p22. In the first BHR step, a spectinomycin resistance cassette and I-CeuI site were inserted at the 5' end of the human BAC. In the second BHR step, ~44 kb sequence, containing the NCR1 gene was deleted from the 3' end of the human BAC and replaced with a neomycin-resistance cassette flanked by mutant lox sites (lox2372-Ub-neo-lox2372) and a 3' PI-SceI site. This construct (Construct B) now contained, from 5' to 3': a spectinomycin-resistance cassette, an I-CeuI site, 44,887 bp of human genomic sequence (GRCh38 coordinates chr19:54,862,297-54,906, 185), a lox2372-Ub-neo-lox2372 cassette, and a PI-SceI site. The human sequence included the last ~5 kb of the KIR3DL2 gene (starting in intron 6), the entire FCAR gene (~17 kb), and the 5' UTR of the NCR1 gene.

Figure 3:
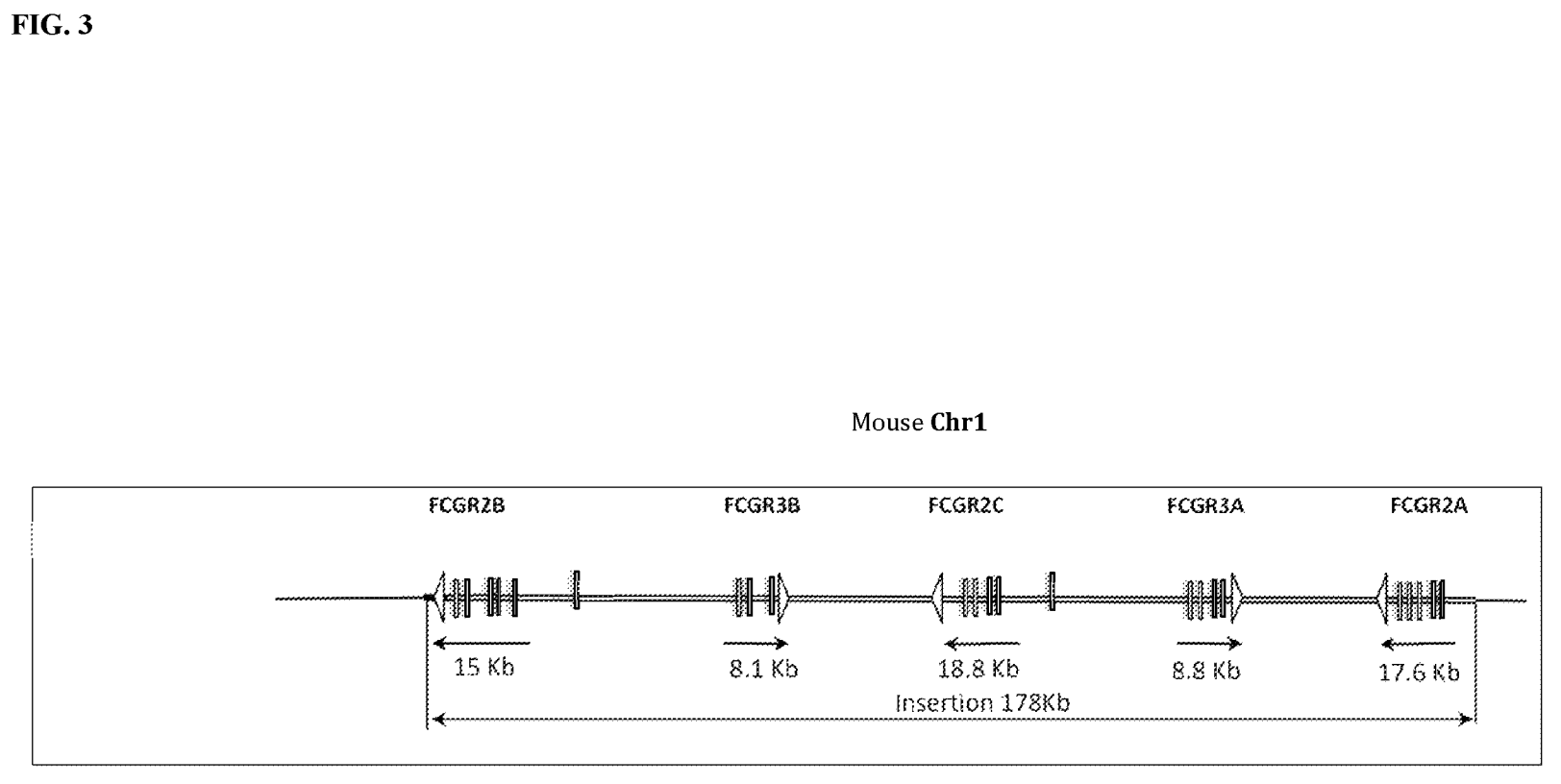

To make the final targeting vector (designated MAID20277), Constructs A and B were both digested with I-CeuI and PI-SceI restriction enzymes and ligated together. The final targeting vector contained, from 5' to 3': the 5' mouse homology arm, an I-CeuI site, the 44,887 bp human genomic insert including the FCAR gene, the lox2372-Ub-Neo-lox2372 cassette, a PI-SceI site, the 3' mouse homology arm, and a chloramphenicol-resistance cassette; final clone The MAID20277 targeting vector was electroporated into mouse embryonic stem (ES) cells comprising human low affinity Fcγ receptors. The genetic modification of low affinity Fcγ receptor locus is described in U.S. Pat. No. 8,658,154, and depicted schematically in FIG. 3. Targeted homologous recombination resulted in deletion of ~8.4 kb of mouse sequence (GRCm38 coordinates chr7:4,303,905-4, 312,280) and insertion of ~44 kb of human sequence including the FCAR gene. Successful integration was confirmed by a modification of allele (MOA) assay as described, e.g., in Valenzuela et al, supra. Primers (forward (F) and reverse (R) primers) and probes used for the MOA assay for detecting presence of human FCAR sequences and the loss of mouse LRC sequences are depicted in Table 3 below, and their locations are designated in FIG. 1A. The antibody resistance cassette was subsequently removed by transient expression of CRE recombinase in the ES cell clone, FIG. 1B.

TABLE 3

Figure 2:
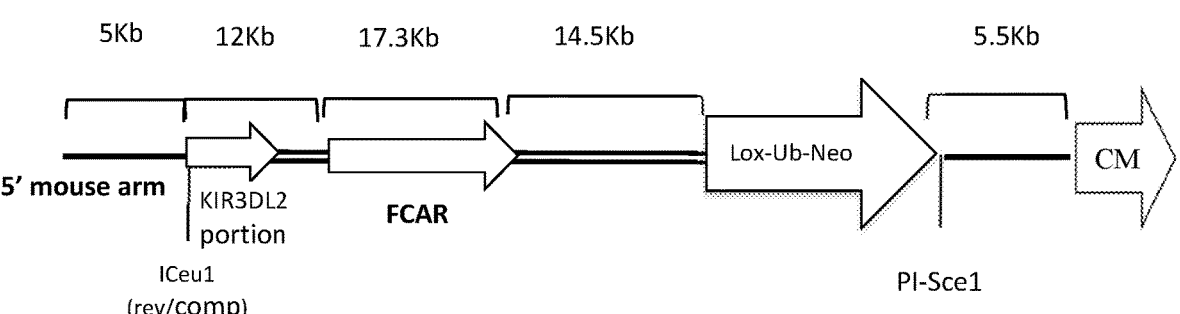
FIG. 2 is a diagram (not to scale) of a targeting vector comprising a sequence homologous to the mouse genome ("5' mouse homology arm"), an I-CeuI site, the 44,887 bp human genomic insert including the FCAR gene, the lox2372-Ub-Neo-lox2372 cassette, a PI-SceI site, a second sequence homologous to the mouse genome, and a chloramphenicol (denoted "CM")-resistance cassette.

| Description (probe and F and R primers) | Sequence | Loss of Allele (LOA) or Gain of Allele (GOA) | SEQ ID NO |
|---|---|---|---|
| GOA 1 Probe | ACCCAGAAGGGCCCTCCAAGC | GOA | 5 |
| F | GGTGTCTGCCCATGAAATGAG | | 6 |
| R | GCAGGCTCTTGGTCCATTACAG | | 7 |
| | | | |
| GOA 2 Probe | AGGCACAGGAAGGTAAGTGTCC | GOA | 8 |
| F | CTGTCTGGGCCAGAGGATTC | | 9 |
| R | GCTCCCAAGAGGGTCTAAAGG | | 10 |
| | | | |
| GOA 3 probe | TGTCTCCAGACTCCATCCACCAA | GOA | 11 |
| F | CAACCACCAACCATTCATCTCCTT | | 12 |
| R | ACGGCCATGCGGATCAAGT | | 13 |
| | | | |
| GOA 4 Probe | TGTCAGAGGGACCACGGCCTTT | GOA | 14 |
| F | TGCTGGCTAGACCACAGATG | | 15 |
| R | CACGTTGACTGCTTTCATCAGAA | | 16 |
| | | | |
| mLOA 1 probe | TCTATATGAAGGCAAGCTGGTCAAGTCA | LOA | 17 |
| F | CTGGGCTGGTGGTCCTAA | | 18 |
| R | CAGCTTACTGGCTTGTTTCTCA | | 19 |
| | | | |
| mLOA 2 probe | TTGACACAAAGTATCTGAGTGGTGGAA | LOA | 20 |
| F | GGACCTGTACTGGCTAGATTCATG | | 21 |
| R | GCTTGCCTACAGTCCAGTCTTG | | 22 | was selected based on CM/kanamycin resistance (FIG. 2). Various junctions in the final clone are depicted in Table 2.

TABLE 2

| Junction | Sequence |
|---|---|
| Mouse 5' arm/ I-CeuI/ human sequence within intron 6 of the KIR3DL2 gene | CTACCCATGCTCTACCCTAGTACCCTTTCTTCAG CACTCCCCTCTCTGTGTCGCTACCTTAGGACCGT TATAGTTAGAGTCAAGAGGGTTGTGGATGTAGAA ACTGTAAAGCACATTCACTGTGTAT (SEQ ID NO: 23) |
| human/ AgeI/ 5' lox2372 | GGCCCGCCCGGCTCAGTCCCACTGCTCAGCACT AGGCCGGCAGAATCTGACCGGTA*TAACTTCGTAT AAGGTATCCTATACGAAGTTAT* (SEQ ID NO: 24) |
| 3' lox2372/ PI-SceI/ mouse 3' arm | *ATAACTTCGTATAAGGTATCCTATACGAAGTTAT* CTCGAGATCTATGTCGGGTGCGGAGAAAGAGGTA ATGAAATGGCATATGAATGCAGGTAAGGGGGAAA CCTCACAGAATATCCAGAATTCTGTTAT (SEQ ID NO: 25) |

Positively targeted ES cells (also comprising genes encoding human low affinity Fcγ receptors, set forth above) were used as donor ES cells and microinjected into a pre-morula (8-cell) stage mouse embryo by the VELOCI-MOUSE® method (see, e.g., U.S. Pat. Nos. 7,576,259; 7,659,442; 7,294,754; and US 2008-0078000 A1, the contents of each are incorporated herein by reference in their entirety). The mouse embryo comprising the donor ES cells was incubated in vitro and then implanted into a surrogate mother to produce an FO mouse fully derived from the donor ES cells. Mice bearing a human FCAR gene (and genes encoding human low affinity Fcγ receptors) were identified by genotyping using the MOA assay described above. Mice heterozygous for the human FCAR gene were bred to homozygosity.

Alternatively to the strategy described above, the targeting vector is electroporated into wild-type ES cells (comprising an endogenous low affinity Fcγ receptor), and mice are generated using VELOCIMOUSE® method. Mice comprising human FcαR are bred to mice comprising human low affinity FcγRs (having locus described in FIG. 3). Mice comprising human FcαR (and, optionally, human low affinity FcγRs) may also be bred to mice comprising human or humanized high affinity FcγR, FcεR, FcRn, β2M; and mice comprising humanized Ig heavy and/or light chain loci using techniques well known in the art.

Example 1.2: Phenotype Analysis of Genetically Engineering of Mice Comprising Human or Humanized FcαR Mice described in Example 1.1 above, comprising human FCAR and low affinity FCGR genes were analyzed for FcαR expression. All mice were housed and bred in the specific pathogen-free conditions. Mice were sacrificed, and spleens and blood were harvested. Blood was collected into BD microtainer tubes with EDTA (Cat #365973). Red blood cells from spleen and blood preparations were lysed with ACK lysis buffer (ThermoFisher, Cat. #A1049201), followed by washing with complete RPMI medium.

Both spleen and blood cells were incubated with Live Dead Aqua (ThermoFisher) for exclusion of non-viable cells. Prior to staining, cells were incubated with anti-mouse CD16/32 (2.4G2; BD) on ice for 10 minutes. Cells were then stained with fluorochrome conjugated anti-human CD89 (BioLegend, Clone No. A59) and the following anti-mouse antibodies; CD45 (BioLegend, Clone No. 30-F11), B220 (BioLegend, Clone No. RA3-6B2), CD11c (BioLegend, Clone No. N418), Ly6G (BioLegend, Clone No. 1A8), Ly6C (BioLegend, Clone No. HK1.4), SiglecF (BD Biosciences Clone No. E50-2440), NKp46 (BioLegend, Clone No. 29A1.4), CD11b (BioLegend, Clone No. M1/70), F4/80 (BD Biosciences Clone No. T45-2342), and NK1.1 (BioLegend, Clone No. PK136) for 30 min on ice.

Lymphocyte and myeloid cell populations were identified by flow cytometry on the BD Symphony A3 instrument (BD Biosciences). First, viable single cells were gated on CD45+. The following subsets were then identified: B cells (B220+), cDCs (CD11c++), pDCs (CD11cint, Ly6C+B220+), PMN Ly6G+Ly6C+), eosinophils (Ly6G−, SiglecF+CD11b+), macrophages/monocytes (Ly6G−, SiglecF−, F4/80+ CD11b+), and NK cells (Ly6G−, SiglecF−, F4/80−CD11b−, NK1.1+). Expression of CD89 (FcαR) was determined on each cell type.

Figure 4A:
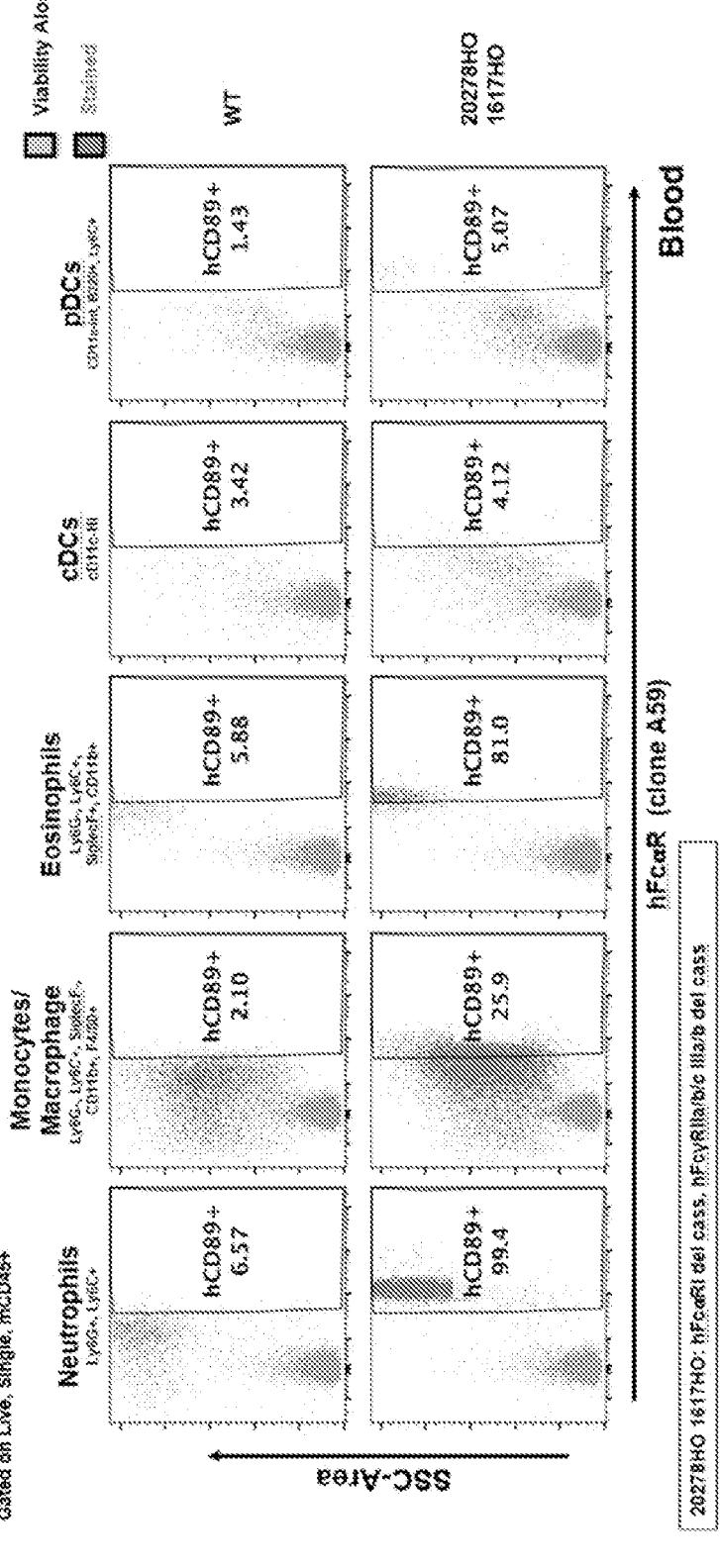
FIG. 4A includes flow cytometry plots that detect the expression of FcαR in cells in a blood sample obtained from mice genetically engineered with the MAID20278 cassette.
Figure 4B:
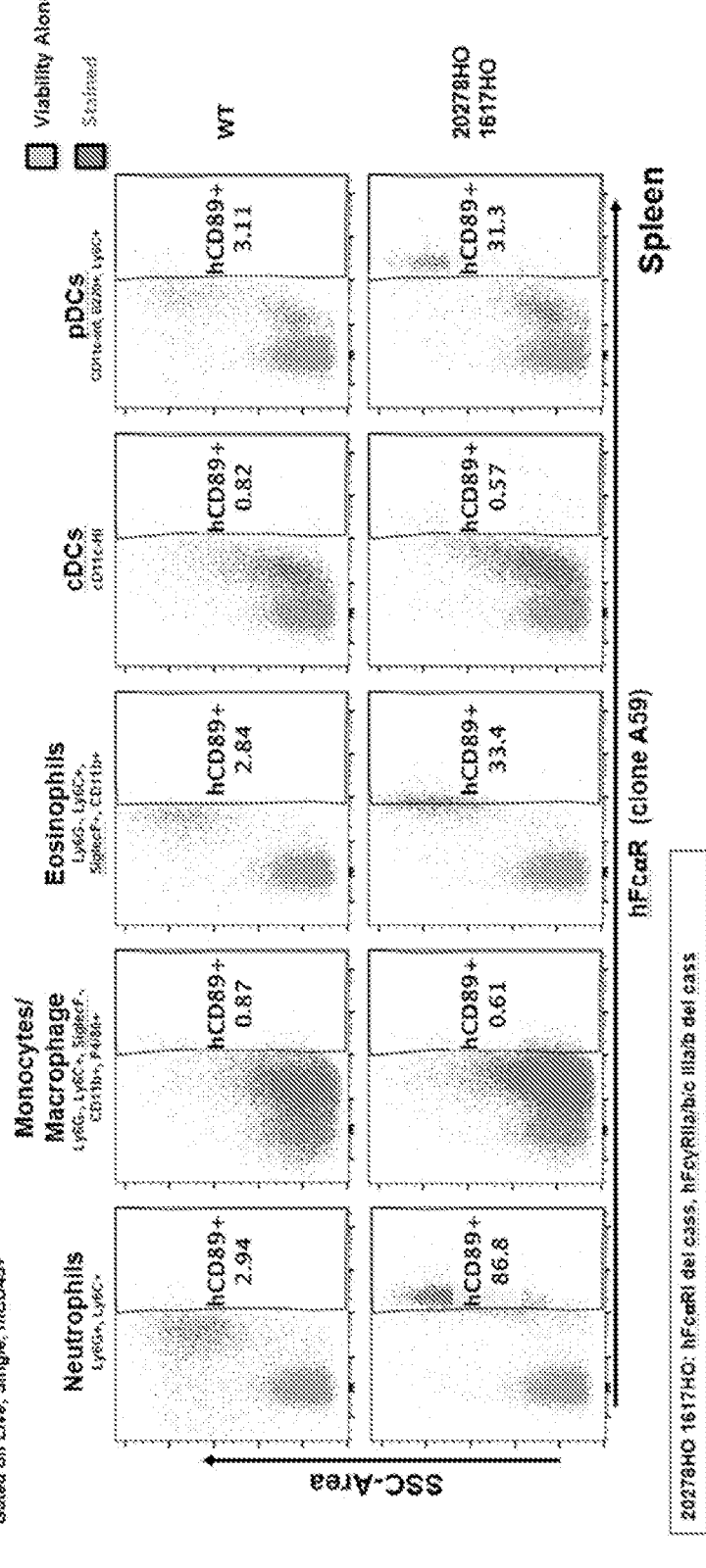
FIG. 4B includes flow cytometry plots that detect the expression of FcαR in splenic cells obtained from mice genetically engineered with the MAID20278 cassette.

The mice genetically engineered with the MAID20278 cassette exhibited a gain of hFcαR on splenic and blood neutrophils, eosinophils, some blood monocytes/macrophages, and splenic plasmacytoid dendritic cells. No hFcαR expression was observed in splenic monocytes or macrophages (FIGS. 4A-4B).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. A mouse comprising in its genome an Fc alpha receptor (FcαR) locus positioned in the mouse leukocyte receptor complex (LRC), wherein the FcαR locus comprises a nucleic acid sequence encoding a FcαR polypeptide comprising a human extracellular domain and a human or rodent cytoplasmic domain, and further comprising in its genome a human or humanized Fc gamma receptor (FcγR) locus, a human or humanized IgH locus, a human or humanized Igκ locus, a human or humanized Igλ locus, a human or humanized FcRn locus, a human or humanized β2M locus, and/or a human or humanized FcεR1α locus.

2. The mouse of claim 1, wherein the FcαR locus is positioned in an intergenic region between the gene loci for the Pira6 protein and the Ncr1 protein.

3. The mouse of claim 1, wherein the FcαR locus is positioned between coordinates 4,303,905-4,312,280 on mouse chromosome 7 (+strand, GRCm38 assembly).

4. The mouse of claim 1, wherein the nucleic acid sequence encodes a fully human FcαR polypeptide.

5. The mouse of claim 1, wherein the FcαR locus comprises human exons 1-5 of the human Fc alpha receptor gene.

6. The mouse of claim 5, wherein the FcαR receptor locus comprises a genomic sequence found between coordinates 54,862,297 and 54,906,185 on human chromosome 19 (+strand, GRCh38 assembly).

7. The mouse of claim 5, wherein the FcαR locus further comprises a nucleic acid sequence present in a human KIR3DL2 gene and/or a nucleic acid sequence present in the 5'UTR of the human NCR1 gene.

8. The mouse of claim 1, wherein the FcαR locus comprises a non-coding portion of non-mouse rodent FcαR exon 1, a coding portion of human FcαR exons 1 and 2, human FcαR exons 3 and 4, and non-mouse rodent FcαR exon 5.

9. The mouse of claim 1, wherein the mouse expresses the FcαR polypeptide on mouse neutrophils, monocytes, macrophages, eosinophils, and dendritic cells.

10. The mouse of claim 1, wherein the mouse is homozygous for the FcαR locus.

11. The mouse of claim 1, wherein the FcαR polypeptide comprises a human or rodent transmembrane domain.

12. A mouse comprising in its genome an Fc alpha receptor (FcαR) locus positioned in the mouse leukocyte receptor complex (LRC), wherein the FcαR locus comprises a nucleic acid sequence encoding a FcαR polypeptide comprising a human extracellular domain, a human transmembrane domain, and a human cytoplasmic domain, wherein the FcαR locus comprises human exons 1-5 of the human Fc alpha receptor gene, and wherein the FcαR locus further comprises a nucleic acid sequence present in the 5'UTR of the human NCR1 gene.

13. The mouse of claim 12, wherein the FcαR locus further comprises a nucleic acid sequence present in a human KIR3DL2 gene.

14. The mouse of claim 12, wherein the FcαR locus is positioned in an intergenic region between the gene loci for the Pira6 protein and the Ncr1 protein.

15. The mouse of claim 12, wherein the FcαR locus is positioned between coordinates 4,303,905-4,312,280 on mouse chromosome 7 (+strand, GRCm38 assembly).

16. The mouse of claim 12, wherein the FcαR receptor locus comprises a genomic sequence found between coordinates 54,862,297 and 54,906,185 on human chromosome 19 (+strand, GRCh38 assembly).

17. The mouse of claim 12, wherein the mouse expresses the FcαR polypeptide on mouse neutrophils, monocytes, macrophages, eosinophils, and dendritic cells.

18. The mouse of claim 12, wherein the mouse is homozygous for the FcαR locus.

19. The mouse of claim 12, further comprising in its genome a human or humanized Fc gamma receptor (FcγR) locus, a human or humanized IgH locus, a human or humanized Igκ locus, a human or humanized Igλ locus, a human or humanized FcRn locus, a human or humanized β2M locus, and/or a human or humanized FcεR1α locus.

20. A mouse comprising in its genome an Fc alpha receptor (FcαR) locus positioned in the mouse leukocyte receptor complex (LRC), wherein the FcαR locus comprises a nucleic acid sequence encoding a FcαR polypeptide comprising a human extracellular domain, a rodent transmembrane domain, and a rodent cytoplasmic domain, wherein the FcαR locus comprises a non-coding portion of non-mouse rodent FcαR exon 1, a coding portion of human FcαR exons 1 and 2, human FcαR exons 3 and 4, and non-mouse rodent FcαR exon 5.

21. The mouse of claim 20, wherein the FcαR locus is positioned in an intergenic region between the gene loci for the Pira6 protein and the Ncr1 protein.

22. The mouse of claim 20, wherein the FcαR locus is positioned between coordinates 4,303,905-4,312,280 on mouse chromosome 7 (+strand, GRCm38 assembly).

23. The mouse of claim 20, wherein the mouse expresses the FcαR polypeptide on mouse neutrophils, monocytes, macrophages, eosinophils, and dendritic cells.

24. The mouse of claim 20, wherein the mouse is homozygous for the FcαR locus.

25. The mouse of claim 20, further comprising in its genome a human or humanized Fc gamma receptor (FcγR) locus, a human or humanized IgH locus, a human or humanized Igκ locus, a human or humanized Igλ locus, a human or humanized FcRn locus, a human or humanized β2M locus, and/or a human or humanized FcεR1α locus.

* * * * *

SEQUENCE LISTING

```
<160> NUMBER OF SEQ ID NOS: 25

<210> SEQ ID NO 1
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
ggcttcaaac tcagacctgc at                                              22

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
cacagagagg ggagtgctga a                                               21

<210> SEQ ID NO 3
<211> LENGTH: 21
<212> TYPE: DNA
<213> ORGANISM: Artificial Sequence
<220> FEATURE:
<221> NAME/KEY: source
```

-continued

```
<223> OTHER INFORMATION: /note="Description of Artificial Sequence:
      Synthetic primer"

<400> SEQUENCE: 3
tatgaatgca ggtaaggggg a                                        21

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
acagttgagc aagcgtcctt                                          20

<210> SEQ ID NO 5
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 5
acccagaagg gccctccaag c                                        21

<210> SEQ ID NO 6
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
ggtgtctgcc catgaaatga g                                        21

<210> SEQ ID NO 7
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
gcaggctctt ggtccattac ag                                       22

<210> SEQ ID NO 8
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 8
aggcacagga aggtaagtgt cc                                       22

<210> SEQ ID NO 9
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
ctgtctgggc cagaggattc                                               20

<210> SEQ ID NO 10
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
gctcccaaga gggtctaaag g                                             21

<210> SEQ ID NO 11
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 11
tgtctccaga ctccatccac caa                                           23

<210> SEQ ID NO 12
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
caaccaccaa ccattcatct cctt                                          24

<210> SEQ ID NO 13
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
acggccatgc ggatcaagt                                                19

<210> SEQ ID NO 14
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 14
```

-continued

--- tgtcagaggg accacggcct tt                                                        22

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
tgctggctag accacagatg                                                           20

<210> SEQ ID NO 16
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
cacgttgact gctttcatca gaa                                                       23

<210> SEQ ID NO 17
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 17
tctatatgaa ggcaagctgg tcaagtca                                                  28

<210> SEQ ID NO 18
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
ctgggctggt ggtcctaa                                                             18

<210> SEQ ID NO 19
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
cagcttactg gcttgtttct ca                                                        22

<210> SEQ ID NO 20
<211> LENGTH: 27
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic probe"

<400> SEQUENCE: 20
ttgacacaaa gtatctgagt ggtggaa                                          27

<210> SEQ ID NO 21
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
ggacctgtac tggctagatt catg                                             24

<210> SEQ ID NO 22
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
gcttgcctac agtccagtct tg                                               22

<210> SEQ ID NO 23
<211> LENGTH: 127
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
ctacccatgc tctaccctag taccctttct tcagcactcc cctctctgtg tcgctacctt      60
aggaccgtta tagttagagt caagagggtt gtggatgtag aaactgtaaa gcacattcac     120
tgtgtat                                                               127

<210> SEQ ID NO 24
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
ggcccgcccg gctcagtccc cactgctcag cactaggccg gcagaatctg accggtataa      60
cttcgtataa ggtatcctat acgaagttat                                       90

<210> SEQ ID NO 25
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

-continued

```
<400> SEQUENCE: 25
ataacttcgt ataaggtatc ctatacgaag ttatctcgag atctatgtcg ggtgcggaga      60
aagaggtaat gaaatggcat atgaatgcag gtaaggggga aacctcacag aatatccaga     120
attctgttat                                                            130
```